US007279317B2

(12) United States Patent
Deshaies et al.

(10) Patent No.: US 7,279,317 B2
(45) Date of Patent: Oct. 9, 2007

(54) MODULATION OF COP9 SIGNALSOME ISOPEPTIDASE ACTIVITY

(75) Inventors: Raymond J. Deshaies, Claremont, CA (US); Gregory Cope, Pasadena, CA (US); Rati Verma, Pasadena, CA (US); Xavier I. Ambroggio, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 10/340,578

(22) Filed: Jan. 9, 2003

(65) Prior Publication Data
US 2003/0153097 A1 Aug. 14, 2003

Related U.S. Application Data

(63) Continuation-in-part of application No. 10/047,253, filed on Jan. 14, 2002, and a continuation-in-part of application No. 10/046,961, filed on Jan. 14, 2002, now Pat. No. 6,846,663.

(60) Provisional application No. 60/355,334, filed on Feb. 6, 2002, provisional application No. 60/322,030, filed on Sep. 14, 2001, provisional application No. 60/322,322, filed on Sep. 14, 2001, provisional application No. 60/261,314, filed on Jan. 12, 2001.

(51) Int. Cl.
| C12N 9/48 | (2006.01) |
| C12N 9/00 | (2006.01) |
| C12Q 1/00 | (2006.01) |
| C12Q 1/68 | (2006.01) |
| C12Q 1/37 | (2006.01) |
| C07H 21/04 | (2006.01) |
| A01N 25/00 | (2006.01) |

(52) U.S. Cl. .................. 435/212; 435/183; 435/4; 435/6; 435/24; 514/789; 536/23.2; 536/23.7; 536/23.5

(58) Field of Classification Search ................ 435/183, 435/212, 440, 4, 6, 24, 69.1, 18, 25, 252.3, 435/320.1, 71.1, 789; 530/350; 514/789; 536/23.2, 23.7, 23.5
See application file for complete search history.

(56) References Cited

U.S. PATENT DOCUMENTS 5,976,796 A 11/1999 Szalay et al. .................. 435/6

(Continued)

FOREIGN PATENT DOCUMENTS

WO 00/29436 A1 5/2000

OTHER PUBLICATIONS

Zhou et al. The fission yeast COP9/signalosome is involved in cullin modification by ubiquitin-related Ned8p. BMC Biochemistry (2001) 2:7.*

(Continued)

*Primary Examiner*—P. Achutamurthy
*Assistant Examiner*—Yong D. Pak
(74) *Attorney, Agent, or Firm*—DLA Piper US LLP

(57) ABSTRACT

Methods for identifying agents that can increase or decrease the isopeptidase activity of a COP9 signalsome (CSN) are provided, as are agent identified using such screening assays. In addition, methods of ameliorating a pathologic condition such as a cancer or an autoimmune disease in a subject by modulating the CSN isopeptidase activity are provided, as are medicaments useful for treating a subject having such a condition.

22 Claims, 5 Drawing Sheets

```
AMSH1    THNEFTITHVIVP--KQSAGFDYCDMENVEELFNVQDQHD--LLTLGWIHTHPTQTAFLS
AMSH2    THNEFTITHVIVP--KQSAGFDYCDMENVEELFNVQDQHD--LLTLGWIHTHPTQTAFLS
AMSH     MRNEFTITHVLIP--KQSAGSDYCNTENEEELFLIQDQQG--LITLGWIHTHPTQTAFLS
Rpn11    TVRVIDVFAMFQS--GTGVSVEAVDFVFQAKMLDMLKQTGRPEMVVGWYHSHPGFGCWLS
Jab1     TMIIMDSFALPVEGTETRVNAQAAAYEYMAAYIENAKQVGRLENAIGWYHSHPGYGCWLS
           :      :    ..   :         :  . *  .   . :**  *:*    .:**

AMSH1    SVDLHTHCSYQLMLPEAIAIVCSPKHKDTG-----IFRLTNAGMLEVSACKKKGFH---PH
AMSH2    SVDLHTHCSYQLMLPEAIAIVCSPKHKDTG-----IFRLTNAGMLEVSACKKKGFH---PH
AMSH     SVDLHTHCSYQMMLPESVAIVCSPKFQETG-----FFKLTDHGLEEISSCRQKGFH---PH
Rpn11    GVDINTQQSFEALSERAVAVVVDPIQSVKGKVVIDAFRLINANMMVLGHEFRQTTSHLGH
Jab1     GIDVSTQMLNQQFQEPFVAVVIDPTRTISAG----KVNLGAFRTYPKGYKPFDEGPSEYQ
          .:*: *:  :  :  :*:*.*     ..       ..*   .    .          :

AMSH1    TKEFRLFSICKHV--LVKDIKI---------IVLDLR----------------------
AMSH2    TKEFRLFSIQKFLSGIISGTAL----------EMEPLKIGYGFNGFPLLGISRSSSPSEQ
AMSH     SKDPPLFCSCSHVT--VVDRAV----------TITDLR----------------------
Rpn11    LNKPSIQALIHGLNRHYYSITINYRKNELEQKMLLNLHKKSHMEGLTLQDYSEHCKHNES
Jab1     TIPLNKIEDFGVHCKQYYALEVSYFKSSLDRKLLELLWNKYWVNTLSSSSLLTNADYTTG
                     :           :      *

AMSH1    --------------------------------------------------------------
AMSH2    L-------------------------------------------------------------
AMSH     --------------------------------------------------------------
Rpn11    VVKEMLELAKNVNKAVEEEDKMTPEQLAIKNVGKQDFKRHLEEHVDVLMTSNIVQCLAAM
Jab1     QVFDLSEKLEQSEAQLGRGSFMLG--LETHDRKSEDKLAKATRDSCKTTIEAIHGLMSQV

AMSH1    ------------
AMSH2    ------------
AMSH     ------------
Rpn11    LDTVVFK-----
Jab1     IKDKLFNQINIS
```

U.S. PATENT DOCUMENTS 6,165,731 A    12/2000    Deshaies et al. ............. 435/7.1

OTHER PUBLICATIONS

Cenciarelli et al., "Identification of a family of human F-box proteins", *Curr. Biol.*, 9(20):1177-1179; S1-S3 (Oct. 1999).

Chamovitz et al., "JAB1/CSN5 and the COP9 Signalsome: A Complex Situation", *EMBO Reports*, 2(2):96-101 (Feb. 2001).

Ciechanover et al., "Ubiquitin-Mediated Proteolysis: Biological Regulation Via Destruction", *BioEssays*, 22(5):442-451 (May 2000).

Cope et al., "Role of predicted metalloprotease motif of Jab1/Csn5 in cleavage of Nedd8 from Cul1", *Science*, 298(5593):608-611 (Oct. 2002).

Deshaies, "SCF and Cullin/RING H2-Based Ubiquitin Ligases", *Annu. Rev. Cell Dev. Biol.*, 15:435-467, Annual Review (1999).

Dive et al., "Phosphinic peptide inhibitors as tools in the study of the function of zinc metallopeptidases", *Biochem. Soc. Trans.*, 28(4):455-460 (2000).

Eytan et al., "Ubiquitin C-terminal hydrolase activity associated with the 26 S protease complex", *J. Biol. Chem.*, 268(7):4668-4674 (Mar. 1993).

Garber, "Cancer research. Taking garbage in, tossing cancer out?", *Science*, 295(5555):612-613 (Jan. 2002).

Glickman et al., "The Regulatory Particle of the *Saccharomyces cerevisiae* Proteasome", *Molecular and Cellular Biology*, 18(6):3149-3162 (Jun. 1998).

Groll et al., "The Eukaryotic 20S Proteaome: A Potential Target for Drug Development", In DFG-Schwerpunkt, Strktur, Funktion and Regulation des 20S/26S Ubiquitin-Proteasomesystems Kolloquium, May 23-25, 2001, Program Abstract, accessed on Internet Jun. 20, 2002 at www.dfg-sp-ubiquitin.de.

Hicke, "A new ticket for entry into building vesicles-ubiquitin", *Cell*, 106(5):527-530 (Sep. 2001).

Kawakami et al., "NEDD8 recruits E2-ubiquitin to SCF E3 ligase", *EMBO J.*, 20(15):4003-4012 (Aug. 2001).

Lyapina et al., "Promotion of NEDD8-CUL1 Conjugate Cleavage By COP9 Signalsome", *Science*, 292(5520):1382-1385 (May 2001).

Meiners et al., "Role of the Ubiquitin-Protease Pathway In Vascular Restenosis—Proteasome Inhibition As A New Therapeutic Approach", In DFG-Schwerpunkt, Strktur, Funktion and Regulation des 20S/26S Ubiquitin-Proteasomesystems Kolloquium, May 23-25, 2001, Program Abstract, accessed on Internet Jun. 20, 2002 at www.dfg-sp-ubiquitin.de.

Osaka et al., "Covalent modifier NEDD8 is essential for SCF ubiquitin-ligase in fission yeast", *EMBO J.*, 19(13):3475-3484 (Jul. 2000).

Reiss et al., "Specificity of Binding of $NH_2$-terminal Residue of Proteins to Ubiquitin-Protein Ligase", *J. Biol. Chem.*, 263(6):2693-2698 (Feb. 1988).

Schwechheimer et al., "Interactions of the COP9 signalsome with the E3 ubiquitin ligase SCFTIRI in mediating auxin response", *Science*, 292(5520):1379-1382 (May 2001).

Verma et al., "A proteasome howdunit: the case of the missing signal", *Cell*, 101(4):341-344 (May 2000).

Verma et al., "Proteasomal proteomics: identification of nucleotide-sensitive proteasome-interacting proteins by mass spectrometric analysis of affinity-purified proteasomes", *Mol. Biol. Cell*, 11(10):3425-3439 (Oct. 2000).

Wei et al., "The COP9 Complex Is Conserved Between Plants and Mammals and Is Related to the 26S Proteasome Regulatory Complex", *Current Biology*, 8(16):919-922; S1-S2 (Jul. 1998).

Winston et al., "A family of mammalian F-box proteins", *Curr. Biol.*, 9(20):1180-1182 (Oct. 1999).

Zhang et al., "Solid-Phase Synthesis and Chemical Ligation of Transmembrane Segments of Rhodopsin", Peptides: The Wave of the Future, Proceedings of the 2nd International and 17th American Peptide Symposium, Jun. 9-14, 2001, Leble and Houghten, ed., American Peptide Society (2001).

Verma et al., "Role of Rpn11 Metalloprotease in Deubiquitination and Degradation by the 26S Proteasome", *Science*, Oct. 2002., 298(5593):611-15.

* cited by examiner

```
AMSH1    THNEFTITHVIVP--KQSAGPDYCDMENVEELFNVQDQHD--LLTLGWIHTHPTQTAFLS
AMSH2    THNEFTITHVIVP--KQSAGPDYCDMENVEELFNVQDQHD--LLTLGWIHTHPTQTAFLS
AMSH     MRNEFTITHVLIP--KQSAGSDYCNTENEEELFLIQDQQG--LITLGWIHTHPTQTAFLS
Rpn11    TVRVIDVFAMFQS--GTGVSVEAVDPVFQAKMLDMLKQTGRPEMVVGWYHSHPGFGCWLS
Jab1     TMIIMDSFALPVEGTETRVNAQAAAYEYMAAYIENAKQVGRLENAIGWYHSHPGYGCWLS
           :       :       .. :          :    .*.    .:** *:** .:**

AMSH1    SVDLHTHCSYQLMLPEAIAIVCSPKHKDTG-----IFRLTNAGMLEVSACKKKGFH--PH
AMSH2    SVDLHTHCSYQLMLPEAIAIVCSPKHKDTG-----IFRLTNAGMLEVSACKKKGFH--PH
AMSH     SVDLHTHCSYQMMLPESVAIVCSPKFQETG-----FFKLTDHGLEEISSCRQKGFH--PH
Rpn11    GVDINTQQSFEALSERAVAVVVDPIQSVKGKVVIDAFRLINANMMVLGHEPRQTTSNLGH
Jab1     GIDVSTQMLNQQFQEPFVAVVIDPTRTISAG----KVNLGAFRTYPKGYKPPDEGPSEYQ
         .:*: *:   : :    :*:* .*          ..*      .    .         :

AMSH1    TKEPRLFSICKHV--LVKDIKI----------IVLDLR----------------------
AMSH2    TKEPRLFSIQKFLSGIISGTAL----------EMEPLKIGYGPNGFPLLGISRSSSPSEQ
AMSH     SKDPPLFCSCSHVT--VVDRAV----------TITDLR----------------------
Rpn11    LNKPSIQALIHGLNRHYYSITINYRKNELEQKMLLNLHKKSWMEGLTLQDYSEHCKHNES
Jab1     TIPLNKIEDFGVHCKQYYALEVSYFKSSLDRKLLELLWNKYWVNTLSSSSLLTNADYTTG
                                             :               :   *

AMSH1    ------------------------------------------------------------
AMSH2    L-----------------------------------------------------------
AMSH     ------------------------------------------------------------
Rpn11    VVKEMLELAKNYNKAVEEEDKMTPEQLAIKNVGKQDPKRHLEEHVDVLMTSNIVQCLAAM
Jab1     QVFDLSEKLEQSEAQLGRGSFMLG--LETHDRKSEDKLAKATRDSCKTTIEAIHGLMSQV

AMSH1    -------------
AMSH2    --------------
AMSH     -------------
Rpn11    LDTVVFK-----
Jab1     IKDKLFNQINIS
```

FIGURE 1

```
AMSH1    --------------MPDHTDVSLSPEERVRALSKLGCNITISEDITPRR  35
AMSH2    MDQPFTVNSLKKLAAMPDHTDVSLSPEERVRALSKLGCNITISEDITPRR  50
AMSH     --------------MSDHGDVSLPPEDRVRALSQLGSAVEVNEDIPPRR   35
                       *.** ****.**;******;**.  ; :.***.***

AMSH1    YFRSGVEMERMASVYLEEGNLENAFVLYNKFITLFVEKLPNHRDYQQCAV  85
AMSH2    YFRSGVEMERMASVYLEEGNLENAFVLYNKFITLFVEKLPNHRDYQQCAV  100
AMSH     YFRSGVEIIRMASIYSEEGNIEHAFILYNKYITLFIEKLPKHRDYKSAVI  85
         *******; ****;* ****;*;**;****;****;****;****;....;

AMSH1    PEKQDIMKKLKEIAFPRTDELKNDLLKKYNVEYQEYLQSKNKYKAEILKK  135
AMSH2    PEKQDIMKKLKEIAFPRTDELKNDLLKKYNVEYQEYLQSKNKYKAEILKK  150
AMSH     PEKKDTVKKLKEIAFPKAEELKAELLKRYTKEYTEYNEEKKKEAEELARN  135
         ***;* ;**********;;;*** ;***;*. ** ** ;.*;*    *; ::

AMSH1    LEHQRLIEAERKRIAQMRQQQLESEQFLFFEDQLKKQELARGQMRSQQTS  185
AMSH2    LEHQRLIEAERKRIAQMRQQQLESEQFLFFEDQLKKQELARGQMRSQQTS  200
AMSH     MAIQQELEKEKQRVAQQKQQQLEQEQFHAFEEMIRNQELEKERLKIVQEF  185
         : *;.;* *;;*;** ;*****.*** **; ;;;***  :  ;;;   *

AMSH1    G-LSEQIDGSALSCFS--THQNNSLLNVFADQPNKSDATNYASHSPPVNR  232
AMSH2    G-LSEQIDGSALSCFS--THQNNSLLNVFADQPNKSDATNYASHSPPVNR  247
AMSH     GKVDPGLGGPLVPDLEKPSLDVFPTLTVSSIQPSDCHTTVRPAKPPVVDR  235
         * :. :.*. !. !.  ; : .*.* : **....;* .::.* *;*

AMSH1    ALTPAATLSAVQNLVVEGLRCVVLPEDLCHKFLQLAESNTVRGIETCGIL  282
AMSH2    ALTPAATLSAVQNLVVEGLRCVVLPEDLCHKFLQLAESNTVRGIETCGIL  297
AMSH     SLKPGALSNSESIPTIDGLRHVVVPGRLCPQFLQLASANTARGVETCGIL  285
         :*.*.*  .: .   .:;;***  **;*  **  ;*****.;**.**;******

AMSH1    CGKLTHNEFTITHVIVPKQSAGPDYCDMENVEELFNVQDQHDLLTLGWIH  332
AMSH2    CGKLTHNEFTITHVIVPKQSAGPDYCDMENVEELFNVQDQHDLLTLGWIH  347
AMSH     CGKLMRNEFTITHVLIPKQSAGSDYCNTENEEELFLIQDQQGLITLGWIH  335
         **** ;*******;;******.***; ** ****  ;***;.*;******

AMSH1    THPTQTAFLSSVDLHTHCSYQLMLPEAIAIVCSPKHKDTGIFRLTNAGML  382
AMSH2    THPTQTAFLSSVDLHTHCSYQLMLPEAIAIVCSPKHKDTGIFRLTNAGML  397
AMSH     THPTQTAFLSSVDLHTHCSYQMMLPESVAIVCSPKFQETGFFKLTDHGLE  385
         *;* ***********;************;****;;********.;;**;*;**; *;

AMSH1    EVSACKKKGFHPHTKEPRLFSICKHV--LVKDIKIIVLDLR---------  421
AMSH2    EVSACKKKGFHPHTKEPRLFSIQKFLSGIISGTALEMEPLKIGYGPNGFP  447
AMSH     EISSCRQKGFHPHSKDPPLFCSCSHVT--VVDRAVTITDLR---------  424
         *;*;*;;******;*;* **.  ..;   : .  :  :   *;

AMSH1    ----------------
AMSH2    LLGISRSSSPSEQL  461
AMSH     ----------------
```

FIGURE 2

```
COP9_su5_Hs    VGRLENAIGWYHSHPGYGCWLSGIDVSTQMLNQQFQEPFVA--VVIDPTRTISAGKVNLG
COP9_su5_Dm    VGRMEHAVGWYHSHPGYGCWLSGINVSTQMLNQTYQEPFVA--IVVDPVRTVSAGKVCLG
COP9_su5_At    AGRLENVVGWYHSHPGYGCWLSGIDVSTQRLNQQHQEPFLA--VVIDPTRTVSAGKVEIG
COP9_su5_Ce    EGRKEKVVGWYHSHPGYGCWLSGIDVSTQTLNQKFQEPWVA--IVIDPLRTMSAGKVDIG
AF2198_Arcfu   LPIGMKVFGTVHSHPSPSCRPSEEDLSLFTRFGKYHIIVCY--PYDENSWKCYNRKGEEV
PH0451_Pyrho   MPHDESIKGTFHSHPSPFPYPSEGDLMFFSKFGGIHIIAAF--PYDEDSVKAFDSEGREV
TVN1035_Thevo  KPIDFSLVGSVHSHPSGITKPSDEDLRMFSLTGKIHIIVGY--PYNLKDYSAYDRSGNKV
MTH971_Metth   LPPFTGAVGSVHSHPGPVNLPSAADLHFFSKNGLFHLIIAH--PYTMETVAAYTRNGDPV
aq_1691_Aquae  ISKGMEIVGVYHSHPDHPDRPSQFDLQRAFPDLSYIIFSVQ--KGKVASYRSWELKGDKF
RV1334_Myctu   EDADEVPVVIYHSHTATEAYPSRTDVKLATEPDAHYVLVSTRDPHRHELRSYRIVDGAVT
RadC_Ecoli     IKINASALILAHNHPSGCAEPSKADKLITERIIKSCQFMDL--RVLDHIVIGRGEYVSFA
               ''''''''''''''''''''''''''HSHP'''''''S  ''D
```

FIGURE 3

```
COP9_su5_Hs   VGRLENAIGWYHSHPGYGCWLSGIDVSTQMLNQQFQEPFVA--VVIDPTRTISAGKVNLG
COP9_su5_Dm   VGRMEHAVGWYHSHPGYGCWLSGINVSTQMLNQTYQEPFVA--IVVDPVRTVSAGKVCLG
COP9_su5_At   AGRLENVVGWYHSHPGYGCWLSGIDVSTQRLNQQHQEPFLA--VVIDPTRTVSAGKVEIG
COP9_su5_Ce   EGRKEKVVGWYHSHPGYGCWLSGIDVSTQTLNQKFQEPWVA--IVIDPLRTMSAGKVDIG
Pad1_Dm       TGRPEMVVGWYHSHPGFGCWLSGVDINTQQSFEALSERAVA--VVVDPIQSVKG-KVVID
Pad1_Hs       TGRPEMVVGWYHSHPGFGCWLSGVDINTQQSFEALSERAVA--VVVDPIQSVKG-KVVID
Sks1_Dd       TGRDEIVIGWYHSHPGFGCWLSSVDVNTQQSFEQLQSRAVA--VVVDPLQSVRG-KVVID
Pad1_Sc       TGRDQMVVGWYHSHPGFGCWLSSVDVNTQKSFEQLNSRAVA--VVVDPIQSVKG-KVVID
              ''''''''''''''''''''''''''''HSHP'''''S 'D
```

MODULATION OF COP9 SIGNALSOME ISOPEPTIDASE ACTIVITY

This application claims the benefit of priority under 35 U.S.C. 119(e) to U.S. Ser. No. 60/355,334, filed Feb. 6, 2002, and is a continuation-in-part of U.S. Ser. No. 10/047,253, filed Jan. 14, 2002, and U.S. Ser. No. 10/046,961, filed Jan. 14, 2002, now U.S. Pat. No. 6,846,663 each of which claims the benefit of priority under 35 U.S.C. § 119(e) to U.S. Ser. No. 60/261,314, filed Jan. 12, 2001, U.S. Ser. No. 60/322,322, filed Sep. 14, 2001, and U.S. Ser. No. 60/322,030, filed Sep. 14, 2001, the entire content of each of which is incorporated herein by reference.

BACKGROUND OF THE INVENTION

1. Field of the Invention

This invention relates generally to the protein degradation pathways, and more specifically to compositions and methods for modulating the isopeptidase activity of the COP9 signalsome and, therefore, ubiquitin dependent protein degradation.

2. Background Information

The function of a protein is regulated via various means in a cell. One way to regulate protein function is via conjugation and deconjugation of a modifier protein to a target protein, e.g., neddylation and deneddylation or ubiquitination and deubiquitination.

The major route for protein degradation in the nucleus and cytoplasm of eukaryotic cells is via the ubiquitin/26S proteasome pathway. The 26S proteasome comprises two major subparticles: the 20S proteasome and the 19S regulatory particle. The 20S proteasome is a cylindrical structure with an internal cavity that contains the peptidase active sites. Substrates of the proteasome are inserted into the cylinder, where they are susceptible to digestion by the peptidase active sites of the 20S proteasome. Entry into the 20S proteasome cylinder is governed by the 19S regulatory particle, which caps the ends of the 20S cylinder.

The 19S regulatory particle binds ubiquitinated substrates and translocates them into the inner cavity of the 20S cylinder, where they are degraded. The 19S regulatory particle can be further subdivided into two multiprotein complexes: the base and the lid. The base comprises a set of six ATPases that are thought to unfold substrates and translocate them into the 20S proteasome. The lid is comprised of a set of eight proteins of unknown function. Biochemical data indicate that the presence of the lid renders the proteasome selective for degrading ubiquitinated proteins, but the basis for this selectivity is not known.

The lid subcomplex of the 26S proteasome is evolutionarily related to the COP9-signalsome (CSN) complex, but the significance of this similarity has remained unknown. There are reports that 26S proteasome preparations contain a variety of associated ubiquitin isopeptidase activities (Eytan et al., J. Biol. Chem. 268:4668-74, 1993; Verma et al., Mol. Biol. Cell 11:3425, 2000), but it has not been demonstrated that an ubiquitinated substrate can be completely deubiquitinated by purified 26S proteasome to yield unmodified substrate. The failure to detect such a reaction product may be due to a tight coupling between the deubiquitination of a substrate and its subsequent degradation within the internal cavity of the 20S proteasome.

Proteins that are destined for degradation by the ubiquitin/26S pathway are marked by the attachment of a polyubiquitin chain to the side chains of lysine residues on the target protein. The ubiquitinated protein is recognized by the 26S proteasome by a mechanism that remains poorly understood. Subsequently the ubiquitinated protein is disengaged from any tightly bound partners, unfolded, and translocated into the central cavity of the 20S complex, where it is exhaustively degraded by the proteolytic active sites that are present in this inner cavity.

Despite many years of intensive study of this system, it remains unclear what happens to the substrate-bound polyubiquitin chains that target the substrate for degradation. It appears that ubiquitin is not degraded by the proteasome but, in fact, is recycled. However it remains unclear if the ubiquitin chains enter the inner cavity of the proteasome and emerge unscathed, or are cleaved from the substrate protein prior to or during its translocation into the inner cavity of the 20S. In prior work (Eytan et al., supra, 1993), it was demonstrated that there is an isopeptidase activity or activities associated with the intact 26S proteasome that is able to release free ubiquitin monomers from ubiquitinated substrates that are degraded by the 26S proteasome. It was demonstrated that this activity is sensitive to the metal ion chelator 1,10-phenanthroline, but the identity of a polypeptide that harbors this activity was not established, nor was it established that this activity is intrinsic to the 26S proteasome as opposed to being intrinsic to a protein that binds transiently to the 26S proteasome. This prior work also failed to disclose whether the ubiquitin isopeptidase activity is critical to the protein-degrading function of the 26S proteasome.

Nedd8 is an ubiquitin-like protein that is covalently linked via an isopeptide bond between its carboxy terminus and the epsilon amino group of lysine residues in target proteins (referred to as neddylation). The attachment of Nedd8 to target proteins requires the combined action of a Nedd8-activating enzyme composed of Ula1 and Uba3 subunits (analogous to ubiquitin-activating enzyme, E1), and Ubc12, which is homologous to the ubiquitin-conjugating enzymes (E2). There is no known requirement for an activity equivalent to the ubiquitin ligase (E3) component of ubiquitination pathways. The Nedd8 modification, like ubiquitination, is likely dynamic, although little is known about the nature of the enzymes that would cleave Nedd8 from its targets (i.e., deneddylate, also referred to as deneddylation or deneddylating activity).

A ubiquitin isopeptidase (USP21) can deneddylate Cul1-Nedd8 conjugates, and a second enzyme UCH-L3, can cleave Nedd8-containing fusion proteins at the C-terminus of Nedd8 to release mature Nedd8; Nedd8, like ubiquitin, is made as a precursor with additional C-terminal residues that must be removed before it can be conjugated to proteins. Despite the fact that both USP21 and UCH-L3 can metabolize Nedd8-based substrates, they also act on ubiquitin-based substrates, and it remains unclear whether their biochemical activity towards Nedd8 is relevant in the context of a cell.

In contrast to ubiquitin, the attachment of Nedd8 to proteins does not mark them for degradation. Rather, it appears that neddylation acts to modify protein function, much like phosphorylation. The cullins are the only proteins that have been found to be conjugated with Nedd8. The cullins are a family of six related proteins that bind a RING-H2 domain protein to form the catalytic core of multisubunit ubiquitin ligases. All cullins examined are modified by attachment of Nedd8, and neddylation of Cul1 potentiates the ubiquitin ligase of the SCF complex within which Cul1 resides. Thus, for Cul1-based ubiquitin ligases, neddylation serves as a positive regulator of activity. However, for other cullin-based ubiquitin ligases, the role, if any, of neddylation remains uncertain.

The COP9/signalsome ("CSN") was originally identified as a regulator of photomorphogenetic development in plants. In seedlings grown in the dark, CSN enables a putative ubiquitin ligase, COP1, to mediate rapid turnover of the transcriptional regulatory protein HY5 in the nucleus. In seedlings that have been exposed to light or in CSN mutants, COP1 redistributes from the nucleus to the cytoplasm, thereby stabilizing HY5 and allowing it to accumulate in the nucleus. HY5, in turn, activates the transcription of a broad palette of genes that mediate photomorphogenetic development. Although the general physiological role of CSN in photomorphogenesis has been defined, little is known about other potential physiological functions for CSN, and the biochemical function of CSN remains elusive. Based on the observation that the eight subunits of CSN share homology to subunits of the lid subcomplex of the 19S regulator of the 26S proteasome, it has been suggested that CSN may play a role in ubiquitin-dependent proteolysis. However, a similar pattern of homology is shared with subunits of the eukaryotic initiation factor-3 (eIF3) complex. Besides plants, CSN complexes have been discovered in human cells, *Drosophila*, and the fission yeast *Schizosaccharomyces pombe*. Surprisingly, the budding yeast *Saccharomyces cerevisiae* does not contain an apparent CSN complex, although it contains a gene homologous to the CSN5/JAB1 subunit of CSN complex, thus implicating CSN5 as a critical component of CSN.

Given the role of protein degradation in maintaining normal cell function, and the disruption of this pathway in association with various disorders such as cancer, an understanding of the components involved in regulating ubiquitination and protein degradation would allow the development of drugs that can modify protein degradation. Thus, a need exists to identify the active domain and site of peptidase activity, particularly isopeptidase activity of a protein involved in deconjugation of a modifier protein from a target protein, e.g., deneddylation or deubiquitination such that screening assays can be developed to identify drugs that can selectively modulate protein modification and degradation. The present invention satisfies this need and provides additional advantages.

SUMMARY OF THE INVENTION

The present invention is based on a determination that a mutation affecting the isopeptidase activity of a COP9 signalsome (CSN) synthetically enhances a mutation affecting the activity of an SCF ubiquitin ligase. Accordingly, the present invention relates to an isolated polypeptide comprising a mutant of a JAMM domain, which has an amino acid sequence of HXHXXXXXXXXXXD (SEQ ID NO:1), wherein H is histidine, D is aspartate, and X is any amino acid, and wherein, in the mutant, at least one of the H residues is substituted with any amino acid residue other than H, the D residue is substituted with an amino acid residue other than D, or a combination thereof. Such a polypeptide comprising the mutant JAMM domain, or a protein comprising such a polypeptide, can have increased isopeptidase activity or can have reduced (or no) isopeptidase activity as compared to a polypeptide comprising the normal (i.e., unmutated) JAMM domain.

The JAMM domain can be a JAMM domain of any polypeptide, particularly a polypeptide of a CSN complex, for example, a JAMM domain generally represented by an amino acid sequence of GW(Y/I)H(S/T)HPXXXXXX-SXXD (SEQ ID NO. 2), wherein G is glycine, W is tryptophan, Y is tyrosine, I is isoleucine, H is histidine, S is serine, T is threonine, P is proline, D is aspartate, X is any amino acid, Y/I is either Y or I, and S/T is either S or T. Such JAMM domains are exemplified by

VGRLENAIGWYHSHPGYGCWLSGIDVSTQ (SEQ ID NO:5),

VGRMEHAVGWYHSHPGYGCWLSGIDVSTQ (SEQ ID NO: 6),

AGRLENVVGWYHSHPGYGCWLSGIDVSTQ (SEQ ID NO:7),

EGRKEKVVGWYHSHPGYGCWLSGIDVSTQ (SEQ ID NO:8), or

KGAKLNVVGWFHSHPGYDCWLSNIDIQTQ (SEQ ID NO:9), and mutant JAMM domains are represented by KGAKLNVVGWFASHPGYDCWLSNIDIQTQ (SEQ ID NO:10), KGAKLNVVGWFHSAPGYDCWLSNIDIQTQ (SEQ ID NO:11), or

KGAKLNVVGWFHSHPGYACWLSNINIQTQ (SEQ ID NO:12).

The present invention also relates to an isolated polypeptide comprising a mutant JAMM domain, which has an amino acid sequence of H(S/T)HXXXXXXXSXXD (SEQ ID NO:65), wherein S is serine, (S/T) is serine or threonine, and X is any amino acid, and wherein, in the mutant JAMM domain, at least one of the H residues is substituted with an amino acid residue other than H; the D residue is substituted with an amino acid residue other than D; the S residue is substituted with an amino acid residue other than S; the T residue, when present, is substituted with an amino acid residue other than T, or a combination thereof. Such a polypeptide comprising the mutant JAMM domain can have reduced (or no) isopeptidase activity as compared to a polypeptide comprising the normal (i.e., not mutated) JAMM domain, or can have increased isopeptidase activity as compared to a polypeptide comprising the normal JAMM domain.

The present invention also relates to an isolated JAMM domain consisting essentially of a JAMM domain having an amino acid sequence of EXHyXHyHy(X)$_n$HXHXXXXXXXXXXD (SEQ ID NO:13), wherein E is glutamic acid, Hy is a hydrophobic amino acid residue, X is any amino acid, and (X)$_n$ indicates about 40 to 83 amino acid residues. Also provided is a fusion protein, comprising such an isolated JAMM domain (SEQ ID NO:13) operatively linked to a heterologous polypeptide, and an isolated polynucleotide encoding such a JAMM domain. In addition, the present invention relates to an isolated polypeptide comprising a mutant JAMM domain, which has an amino acid sequence of EXHyXHyHy(X)$_n$HXHXXXXXXXXXXD (SEQ ID NO:13), wherein, in the mutant JAMM domain, at least one of the H residues is substituted with an amino acid residue other than H; the D residue is substituted with an amino acid residue other than D; the E residue is substituted with an amino acid residue other than E; or a combination thereof. The JAMM domain of such a polypeptide can have, for example, an amino acid sequence of EXHyXHyHy(X)$_n$H(S/T)HXXXXXXXSXXD (SEQ ID NO:14), wherein the S residue is substituted with an amino acid residue other than S; and/or the T residue, when present, is substituted with an amino acid residue other than T. Examples of polypeptide having such JAMM domains includes those having an amino acid sequence as set forth in any of SEQ ID NOS:15 to 64.

The present invention also relates to a polynucleotide encoding a polypeptide comprising a mutant JAMM domain. The polynucleotide can be a deoxyribonucleic acid molecule (DNA), a ribonucleic acid molecule (RNA), or a hybrid thereof, and can be single stranded or double stranded. The polynucleotide can be contained in a vector, for example, an expression vector, and can be operatively linked to one or more expression control elements, including, for example, transcriptional or translational regulatory element. The polynucleotide, which can, but need not, be in a vector, can be exogenously introduced into a cell, which can be a prokaryotic or eukaryotic cell, and can be maintained in the cell transiently or stably, for example, integrated into the cell genome.

The present invention further relates to a method of identifying an inhibitor of an isopeptidase activity of a polypeptide by rational drug design, wherein the polypeptide comprises a JAMM domain. Such a method can be performed, for example, by designing a potential inhibitor for the polypeptide that will form a bond with the JAMM domain based upon the crystal structure co-ordinates of the polypeptide, synthesizing the potential inhibitor, and detecting inhibition of isopeptidase activity of the polypeptide by the potential inhibitor, thereby identifying the potential inhibitor as an inhibitor of the polypeptide. The isopeptidase activity can be, for example, deneddylation.

The polypeptide comprising the JAMM domain can be, for example, a component of a CSN, e.g., JAB1, or a component of a 26S proteasome, e.g., RPN11 (also known as POH1). As such, the JAMM domain can be a JAMM domain as exemplified herein (e.g., SEQ ID NOS:5-9) or otherwise known in the art. A potential inhibitor can be designed based, for example, on a likelihood that it will form a bond with a metal ion bound by the JAMM domain, and can be, for example, a peptide, a peptide derivative, a peptoid, a peptidomimetic, a polynucleotide, a polynucleotide derivative, or a small organic molecule. In addition, a potential inhibitor can be designed based on the ability to form a bond or otherwise interact with one or more amino acid residues involved in binding to the metal ion, for example, with at least one of the two histidine residues or with the aspartate (D) residue as set forth in the HXHXXXXXXXXXXD (SEQ ID NO:1) sequence of the JAMM domain; or with one or more amino acid residues involved in maintaining the structure of the metal ion coordinating site, for example, with the first serine residue (or the threonine residue, when present) as set forth in the EXHyXHyHy(X)$_n$H(S/T)HXXXXXXXXSXXD (SEQ ID NO:66), which interacts via its hydroxyl group side with the main chain amide of the upstream glutamic acid residue, or with the second serine residue as set forth in SEQ ID NO:66, which interacts with the main chain amide of the down stream aspartic acid residue; or with the glutamic acid residue as set forth in SEQ ID NO:66, which, as disclosed herein, when mutated results in loss of the isopeptidase activity of Csn5.

The present invention also relates to a method of identifying an agent that modulates an isopeptidase activity of a polypeptide comprising a JAMM domain. Such a method can be performed, for example, by contacting the polypeptide comprising the JAMM domain and a test agent under conditions suitable for isopeptidase activity, wherein said isopeptidase activity cleaves a modifier protein from a target protein, and detecting a change in isopeptidase activity by the polypeptide in the presence of the test agent as compared to the absence of the test agent, thereby identifying an agent that modulates isopeptidase activity of the polypeptide comprising the JAMM domain. According to a screening assay of the invention, the test agent can be identified as one that decreases deconjugation of the modifier protein from the target protein, thereby identifying the test agent as an agent that reduces or inhibits the isopeptidase activity of the polypeptide; or can be identified as a test agent that increases deconjugation of the modifier protein from the target protein, thereby identifying the test agent as an agent that increases the isopeptidase activity of the polypeptide. The isopeptidase activity can be one that cleaves a peptide bond between a carboxy terminus of the modifier protein and an epsilon amino group of a lysine residue of the target protein. For example, the modifier protein is Nedd8, UBL1, SMT3H2, SMT3H1, APG12, FAT10, Fau, UCRP, URM1, or UBL5, and the target protein can be a protein that contains a cullin domain (e.g., Cul1, Cul2, Cul3, Cul4A, Cul4B, or Cul5). A screening assay of the invention can further include contacting the test agent and a 26S proteasome complex comprising the polypeptide comprising the JAMM domain (e.g. RPN11/POH1), wherein detecting isopeptidase activity can be performed by detecting degradation of a protein by the 26S proteasome complex.

In one embodiment of such a method, the target protein comprises a SCF ubiquitin ligase, and a change in isopeptidase activity of the polypeptide is detected by detecting a change in the SCF ubiquitin ligase activity. In another embodiment, the polypeptide comprising the JAMM domain is a polypeptide of a CSN. The target protein or the modifier protein or both can comprise a detectable label, for example, a peroxidase, alkaline phosphatase, luciferase, fluorescent small molecule, fluorescent protein, or a ligand or substrate thereof, such that detecting the isopeptidase activity of the polypeptide can be performed by detecting the detectable label. A fluorescent protein useful as a detectable label can be a green fluorescent protein, yellow fluorescent protein, cyan fluorescent protein, dsRed, or a derivative thereof. In one embodiment, each of the target protein and the modifier protein comprises a detectable label of a fluorescence resonance energy transfer (FRET) pair, such that detecting the isopeptidase activity of the polypeptide can be performed by detecting a change in FRET.

A test agent screened according to a method of the invention can be any type of compound including, for example, a peptide, a peptide derivative (e.g., a peptide hydroxamate or a phosphinic peptide), a peptoid, a peptidomimetic, a polynucleotide, a polynucleotide derivative, or a small organic molecule. Furthermore, the test agent can be one of a library of test agents, for example, a combinatorial library, which can be a combinatorial library of random test agents, biased test agents, or variegated test agents. Exemplary libraries of test agents include a hydroxamate compound library, reverse hydroxamate compound library, carboxylate compound library, thiol compound library, a phosphinic peptide library, or phosphonate compound library.

A screening assay of the invention can be performed in vitro, for example, using purified components such as a purified polypeptide comprising the JAMM domain, or using a biological sample, or an extract of a biological sample, containing such a polypeptide, or can be performed in vivo. The methods are particularly adaptable to a high or ultra-high throughput format, thus facilitating screening of hundreds, thousands, or hundreds of thousands of test agent in parallel. Such high throughput format assays can be performed, for example, by contacting each of a plurality of polypeptides, each polypeptide comprising a JAMM domain, with a test agent, wherein polypeptides in the plurality are different from other polypeptides of the plurality; or by contacting each of number of same or different polypeptides comprising a JAMM domain with one or more of a plurality of test agents, wherein at least one polypeptide of the plurality of polypeptides is contacted with at least one test agent of the plurality of test agents. Accordingly, the present invention provides an agent that modulates the isopeptidase activity of a polypeptide comprising a JAMM domain, wherein the agent is identified according to a method of the invention.

The present invention further relates to a method of treating a condition by modulating protein degradation in a cell associated with the condition. Such a method can be performed, for example, by administering to a subject having or susceptible to the condition at least a first agent that modulates an isopeptidase activity of a polypeptide comprising a JAMM domain. The condition can be a cell proliferative disorder such as a neoplastic growth (e.g., a benign or malignant tumor), or psoriasis; an inflammatory condition, which can be an acute inflammatory disorder due to an infection or a chronic inflammatory disorder; an autoimmune disorder such as multiple sclerosis or rheumatoid arthritis; a condition associated with undesirable angiogenesis as occurs during tumor growth; a condition such as asthma, or ischemia and reperfusion injury; or any other condition in which it is desirable to modulate protein degradation. For example, the condition can be a protein storage disorder or other condition characterized by undesirable protein accumulation, wherein the method is performed by administering to a subject in need an agent that increases isopeptidase activity of a polypeptide comprising the JAMM domain, thereby increasing protein degradation in the cells, and ameliorating the condition.

In one embodiment, a method of the invention utilizes administration of an agent that reduces or inhibits the isopeptidase activity of the polypeptide comprising the JAMM domain, for example, a JAB1 polypeptide or other polypeptide, which can comprise a CSN complex. In another embodiment, the method can further include administering to the subject at least a second agent, which can be any agent that can provide a therapeutic benefit to the subject being treated, for example, a chemotherapeutic agent for a cancer patient, or a corticosteroid for a subject having an autoimmune disorder, or a nutrient and/or vitamin composition, or the like. In one aspect, the second agent is an agent that modulates a component of a protein degradation pathway comprising the polypeptide comprising the JAMM domain. Generally, a second agent that modulates a component of a protein degradation pathway modulates the component similarly to the first agent that modulates that isopeptidase activity of the polypeptide comprising the JAMM domain; i.e., where the first agent reduces or inhibits the isopeptidase activity, the second agent is selected such that it has reducing or inhibiting activity with respect to the other component of the protein degradation pathway. Where a second agent is selected such that it modulates a component of the protein degradation pathway, the component can be, for example, an E2 ubiquitin conjugating enzyme such as Cdc34 or a Ubc4/5 family member, or an E3 ubiquitin ligase such as Skp1, Cul1/Cdc53, an F-box protein, or a combination thereof (e.g., an SCF ubiquitin ligase).

As further disclosed herein, the JAB subunit, more specifically the JAMM domain, is responsible for the peptidase activity of a protein, e.g., the protein's ability of cleaving a peptide bond between the carboxy terminus of a modifier protein and a free amino group of a target protein. The present invention provides polypeptides and crystalline polypeptides containing the JAMM domain and methods of using such domain to treat conditions associated with peptidase activity, especially isopeptidase activity and methods to screen for agents that are capable of modulating its peptidase activity. The present invention also provides methods of using such domain to identify or design compounds that are candidates for modulators of the peptidase activity.

Accordingly, the present invention provides an isolated polypeptide containing a JAMM domain consisting essentially of an amino acid sequence of HXHXXXXXXXXXXD (SEQ ID NO:1), wherein H is histidine, D is aspartate, and X is any amino acid and wherein the JAMM domain is not adjacent to an amino acid sequence that is naturally adjacent to the domain. In another embodiment, the invention provides an isolated crystalline polypeptide containing a JAMM domain consisting essentially of an amino acid sequence of HXHXXXXXXXXXXD (SEQ ID NO:1), wherein H is histidine, D is aspartate, and X is any amino acid. In yet another embodiment, the present invention provides an isolated monoclonal antibody that specifically binds to an epitope within a JAMM domain of a polypeptide, wherein the JAMM domain consists essentially of an amino acid sequence of HXHXXXXXXXXXXD (SEQ ID NO:1), wherein H is histidine, D is aspartate, and X is any amino acid. In still another embodiment, the present invention provides an isolated JAMM domain consisting essentially of a JAMM domain having an amino acid sequence of EXHyXHyHy(X)$_n$HXHXXXXXXXXXXD (SEQ ID NO:13), wherein E is glutamic acid, Hy is a hydrophobic amino acid residue, X is any amino acid, and (X)$_n$ indicates about 40 to 83 amino acid residues, and wherein the JAMM domain is not adjacent to an amino acid sequence that can normally be found adjacent to the domain in a naturally occurring protein.

The present invention also provides a method of identifying an inhibitor of a polypeptide by rational drug design. The polypeptide comprises a JAMM domain consisting essentially of an amino acid sequence of HXHXXXXXXXXXXD (SEQ ID NO:1), wherein H is histidine, D is aspartate, and X is any amino acid. The method comprises designing a potential inhibitor for the polypeptide that will form a bond with the JAMM domain based upon the crystal structure co-ordinates of the polypeptide, synthesizing the inhibitor, and determining whether the potential inhibitor inhibits the activity of the polypeptide. In one aspect of this method, the potential inhibitor is designed based on the potential ability to form a bond with at least one of the histidine residues or with the aspartate residue, or with any combination of those residues, as set forth in the HXHXXXXXXXXXXD (SEQ ID NO:1) sequence of the JAMM domain. The JAMM domain of the polypeptide also can included an extended amino acid sequence, EXHyXHyHy(X)$_n$H(S/T)HXXXXXXXXSXXD (SEQ ID NO:13), wherein S is serine, T is threonine, E is glutamic acid, Hy is a hydrophobic amino acid residue, X is any amino acid, and (X)$_n$ indicates about 40 to 83 amino acid residues, in which case the potential inhibitor also can be designed based on the potential ability to form a bond with one or more of the specified histidine, aspartic acid, glutamic acid, serine, and threonine (when present) residues.

In another embodiment, the potential inhibitor is designed based on an ability to form a bond with a metal ion bound by the JAMM domain. For example, the hydroxamate class of compounds act to inhibit matrix metalloproteases, which contain a zinc ion, by chelating the bound zinc on the enzyme. Zinc generally forms bonds to four ligands in zinc finger and RING finger proteins, whereas metalloproteases, including proteins having a JAMM domain, contain only three proteinaceous ligands (i.e., in a JAMM domain, the H, H, and D residues; see, e.g., SEQ ID NO:1). The fourth coordination position binds the oxygen moiety of a water molecule, which, in a JAMM domain containing polypeptide, is activated by the glutamate residue (see SEQ ID NO:13), which hydrogen bonds to the hydrogen atoms of the water molecule, to initiate hydrolytic attack of the target peptide bond. Classical hydroxamate, carboxylate, thiol, and phosphinic inhibitors of metalloproteases bind to the enzyme and supply a fourth ligand for the enzyme-bound zinc, thus displacing the water molecule and inhibiting catalysis. As such, a potential inhibitor useful for purposes of the present invention is distinguishable from molecules that generally bind zinc atoms, including, for example, from chelating agents such as EDTA, which bind the metal ion and extract or otherwise sequester it from a protein.

In another embodiment, the invention provides a method of deconjugating a modifier protein from a target protein. The modifier protein is conjugated to the target protein via a peptide bond between the carboxy terminus of the modifier protein and a free amino group of the target protein. The method comprises contacting the target protein to a polypeptide comprising a JAMM domain consisting essentially of an amino acid sequence of HXHXXXXXXXXXXD (SEQ ID NO:1), wherein H is histidine, D is aspartate, and X is any amino acid. In yet another embodiment, the invention provides a method of screening for an agent that affects deconjugation of a modifier protein from a target protein. The modifier protein is conjugated to the target protein via a peptide bond between the carboxy terminus of the modifier protein and a free amino group of the target protein. The method comprises incubating in the presence and absence of a test agent, the target protein and a polypeptide comprising a JAMM domain consisting essentially of an amino acid sequence of HXHXXXXXXXXXXD (SEQ ID NO:1), wherein H is histidine, D is aspartate, and X is any amino acid and determining the effect of the test agent. An increase or decrease in the amount of the target protein not conjugated to the modifier protein caused by the test agent is indicative of an agent affecting deconjugation of the modifier protein from the target protein. Accordingly, an agent identified according to a method of the invention also is provided.

The present invention further provides a method of increasing conjugation of a modifier protein to a target protein. The modifier protein is conjugated to the target protein via a peptide bond between the carboxy terminus of the modifier protein and a free amino group of the target protein in a cell comprising inhibiting the activity of a polypeptide comprising a JAMM domain consisting essentially of an amino acid sequence of HXHXXXXXXXXXXD (SEQ ID NO:1), wherein H is histidine, D is aspartate, and X is any amino acid, thereby increasing the conjugation of the modifier protein to the target protein. In addition, the present invention provides a method of treating a condition of neoplastic growth, angiogenesis, infection, chronic inflammation, asthma, ischemia and reperfusion injury, multiple sclerosis, rheumatoid arthritis, or psoriasis. The method comprises administering an agent identified by the method of the present invention to a subject in need of such treatment.

BRIEF DESCRIPTION OF THE DRAWINGS

FIG. 1 shows the sequence alignment of human AMSH proteins (see FIG. 2; SEQ ID NOS:66 to 68) with human JAB1 (SEQ ID NO:3) and Rpn11 (SEQ ID NO:4). Conserved active site residues are boxed.

FIG. 2 shows the sequence alignment of AMSH (SEQ ID NO:66), AMSH1 (SEQ ID NO:67), and AMSH2 (SEQ ID NO:68). The critical conserved active site residues are boxed.

FIG. 3 shows that sequence alignment of COP9 subunit 5 (CSN5/JAB1) orthologs from different eukaryotic species (SEQ ID NOS:69 to 79) reveals conserved histidine, serine, and aspartate residues that are also found in a set of prokaryotic and archaebacterial proteins.

FIG. 4 shows the alignment of Rpn11 orthologs (Pad1; SEQ ID NOS:80 to 83) and CSN5/JAB1 orthologs from different species (SEQ ID NOS:69 to 72).

FIG. 5 provides an alignment of predicted JAMM domains (SEQ ID NOS:15 to 64). Selected sequences were aligned using T-Coffee (Notredame et al, *J. Mol. Biol.* 302:205, 2000, which is incorporated herein by reference) and modified manually to ensure correct superposition of the conserved motifs. Eukaryotic proteins are grouped to reflect orthologous relationships. Position of the aligned region in the sequence is shown by numbers; poorly conserved spacers are not shown and are designated by numbers. The consensus includes amino acid residues conserved in 80% of the aligned sequences; I indicates aliphatic residues (A, I, L, V; yellow shading), h indicates hydrophobic residues (F, Y, W, A, I, L, V, M; yellow shading), and s indicates small residues (G, A, C, S, D, N, V, P; blue letters). Predicted metal-chelating and catalytic residues are shown in yellow against a dark blue background. Secondary structure prediction was made using the PHD program with the multiple alignment submitted as the query (Rost et al., *Comput. Appl. Biosci.* 10:53, 1994, which is incorporated herein by reference); E indicates extended conformation (β-strand), and H indicates a-helix. Each protein is denoted by the GenBank identifier, followed by the gene name and abbreviated species name. Species abbreviations are as follows: Hsa, Homo sapiens; Dme, *Drosophila melanogaster*; Cel, *Caenorhabditis elegans*; Ath, *Arabidopsis thaliana*; S C, *Saccharomyces cerevisiae*; Afu, *Archaeoglobus fulgidus*; Pho, *Pyrococcus horikoshii*; Hsp, *Halobacterium* sp.; Aae, *Aquifex aeolicus*; Nsp, *Nostoc* sp.; Dra, *Deinococcus radiodurans*; Psa, *Pseudomonas aeruginosa*; Vch, *Vibrio cholerae*; Rso, *Ralstonia solanacearum*; Eco, *Escherichia coli*; Bsu, *Bacillus subtilis*; Mac, *Methanosarcina acetivorans* (see Cope et al., *Science* 298; 608611, 2002; Verma et al., *Science* 298: 611-615, each of which is incorporated herein by reference).

DETAILED DESCRIPTION OF THE INVENTION

The present invention is based on a determination that inhibition of the COP9 Signalosome (CSN) isopeptidase activity inhibits ubiquitin ligase activity, thus providing a means to modulate protein degradation in a cell. The CSN has a biological role in cleaving the ubiquitin-like protein Nedd8 from the cullin subunit of SCF (Skp-1/Cullin/F-protein) ubiquitin ligase. In particular, a metalloenzyme motif ("JAMM domain") in the JabI subunit of CSN underlies the Nedd8 conjugate cleavage activity of the CSN complex. As disclosed herein, specific inhibition of the isopeptidase activity of CSN reduces SCF ubiquitin ligase activity. As such, the present invention provides methods for identifying agents that can modulate the activity of the CSN isopeptidase, and further provides agents identified using such screening assays. Such agents, either alone or in combination with other agents (e.g., agents that modulate other components of ubiquitin dependent protein degradation pathways such as E2 ubiquitin conjugating enzyme activity or an F-box substrate binding activity), can be used to ameliorate cell proliferative disorders and autoimmune diseases by modulating SCF activity. Accordingly, medicaments are provided for treating cell proliferative disorders or autoimmune disease by modulating SCF activity in cells associated with the disorder, for example, cancer cells or plasma cells.

The present invention provides relates to an isolated polypeptide comprising a mutant of a JAMM domain, which has an amino acid sequence of HXHXXXXXXXXXXD (SEQ ID NO:1), wherein H is histidine, D is aspartate, and X is any amino acid, and wherein, in the mutant, at least one of the H residues is substituted with any amino acid residue other than H, the D residue is substituted with an amino acid residue other than D, or a combination thereof. Also provided is an isolated polypeptide comprising a mutant JAMM domain, which has an amino acid sequence of H(S/T)HXXXXXXXSXXD (SEQ ID NO:65), wherein S is serine, and (S/T) is serine or threonine, and wherein, in the mutant JAMM domain, at least one of the H residues is substituted with an amino acid residue other than H; the D residue is substituted with an amino acid residue other than D; the S residue is substituted with an amino acid residue other than S; the T residue, when present, is substituted with an amino acid residue other than T, or a combination thereof. In addition, an isolated JAMM domain consisting essentially of a JAMM domain having an amino acid sequence of EXHyXHyHy(X)$_n$HXHXXXXXXXXXXD (SEQ ID NO:13), wherein E is glutamic acid, Hy is a hydrophobic amino acid residue, X is any amino acid, and (X)$_n$ indicates about 40 to 83 amino acid residues, is provided, as is a mutant JAMM domain having an amino acid sequence of EXHyXHyHy(X)$_n$HXHXXXXXXXXXXD (SEQ ID NO:13), wherein, in the mutant JAMM domain, at least one of the H residues is substituted with an amino acid residue other than H; the D residue is substituted with an amino acid residue other than D; the E residue is substituted with an amino acid residue other than E; or a combination thereof.

The term "mutant", when used herein in reference to a JAMM domain, means that at least one amino acid residue of the JAMM domain has been manipulated artificially, i.e., by the hand of man. As such, for purposes of the present invention, a mutant JAMM domain, as well as a polypeptide containing a mutant JAMM domain, is a non-naturally occurring molecule, which can, but need not be based on a sequence of a naturally occurring polypeptide. Methods for making a mutant JAMM domain are disclosed herein or otherwise known in the art and include, for example, chemical synthesis of a peptide comprising a JAMM domain having an amino acid substitution with respect to the sequence of a JAMM domain in a naturally occurring polypeptide (e.g., a substitution of an alanine residue for a histidine residue such as an H residue as set forth in SEQ ID NO:1), or expression of a recombinant nucleic acid molecule encoding the JAMM domain, such a recombinant nucleic acid molecule being, for example, an isolated otherwise naturally occurring nucleic acid molecule modified by a method such as site directed mutagenesis, such that a mutant JAMM domain is encoded. As such, it will be recognized that various naturally occurring proteins such as proteins that contain a JAB domain as well as an amino acid sequence that is reminiscent of a JAMM domain, but differs, for example, in one, two or three of the H, H and D residues as set forth in SEQ ID NO:1, is not encompassed within the meaning of a "mutant" JAMM domain because such naturally occurring proteins are not manipulated by man to generate a mutant JAMM domain.

Protein degradation is regulated primarily by a pathway that involves ubiquitination of the target protein, thus 'marking' it for proteolysis. Ubiquitination occurs via a series of steps, wherein an ubiquitin activating enzyme (generally referred to a "E1") activates ubiquitin, which is transferred to a thiol group of an ubiquitin conjugating enzyme ("E2"), then further transferred to a lysine group of a substrate that is presented to the E2 by a specificity factor ("E3"). SCF is a heterotetrameric E3 ubiquitin ligase that includes Skp1, Cul1/Cdc53, F-box, and Hrt1/Roc1/Rbx1 subunits. SCF recruits both an E2 ubiquitin conjugating enzyme (Ube) and a substrate, and catalyzes the transfer of ubiquitin from the former to the latter (Deshaies, *Ann. Rev. Cell. Devel. Biol.* 15:435-467, 1999, which is incorporated herein by reference). Depending upon the specific cell type, the SCF ubiquitin conjugating enzyme can be either Cdc34 or a member of the Ubc4/5 family. Once a substrate is ubiquitinated, it is typically targeted for degradation by the proteosome (Verma and Deshaies, *Cell* 101:341-344, 2000); however, SCF also can potentially modulate the function of a substrate (positively or negatively) by other mechanisms independent of degradation (Hicke, *Cell* 106:527-530, 2001).

The F-box protein subunit of SCF includes a substrate-binding domain, which recruits substrate to SCF, and an F-box motif, which links the substrate-binding domain to the remainder of the SCF complex. Many different F-box proteins have been discovered, with the human genome alone encoding at least 40 of them (Cenciarelli et al., *Curr. Biol.* 9:1177-1179, 1999, Winston et al., *Curr. Biol.* 9:1180-1182, 1999). As such, human cells can contain as many as 40 distinct SCF complexes, each with a distinctive substrate specificity. Owing in part to this diversity of F-box proteins, SCF ubiquitin ligases can control a broad range of cellular processes, including, for example, regulation of the cytoskeleton, gene transcription, cell cycle progression, and innate immune response (Deshaies, supra, 1999). Accordingly, drugs that target either the shared components of SCF complexes or individual F-box proteins have potential application for the treatment of many different diseases. Indeed, it was recently suggested that the anti-cancer effects of the proteasome inhibitor PS-341 are mediated by stabilization of IκB, which is a substrate of the SCF complex comprised of the F-box protein β-TRCP (Garber, *Science* 295:612-613, 2002).

The mechanism of action of SCF and the regulation of its activity have not yet been completely defined. However, the covalent attachment of the ubiquitin-like protein Nedd8 to the Cul1 subunit of SCF plays an important regulatory role. The gene encoding Nedd8 in fission yeast is essential for growth, and mutation in fission yeast of Cul1 lysine 713, which is the site of attachment of Nedd8, is lethal (Osaka et al., *EMBO J.* 19:3475-3484, 2000)). Thus, the execution of at least one essential function of SCF in fission yeast requires that lysine 713 of Cul1 be modified by Nedd8. Although all members of the cullin family (Cul1-Cul5) can be modified with Nedd8 (Hori et al., *Oncogene* 189:6829-6834, 1999), the role of this modification in cullin function has been described only for Cul1. In vitro experiments with purified SCF complexes indicate that the attachment of Nedd8 to Cul1 stimulates the biochemical activity of SCF by promoting recruitment of ubiquitin-conjugating enzyme to the complex (Kawakami et al., *EMBO J.* 20:4003-4012, 2001).

In addition to the attachment of Nedd8 to SCF being important for SCF ubiquitin ligase activity, the removal of Nedd8 conjugates from SCF also can be important for SCF function. The possibility that cyclical addition and removal of Nedd8 is important for SCF function was suggested by the observation that cosuppression of the Csn5 subunit of CSN in Arabidopsis thaliana exacerbated the effects of mutations in the AXR1 gene, which encodes a subunit of the Nedd8 attachment enzyme, on the responsiveness of plants to the hormone auxin (Schwechheimer et al., Science 292: 1379-1382, 2001). However, the result is inconclusive for at least two reasons. First, it was not established that SCF is the major or only target of Csn5 and Axr1 in auxin signaling. As such, it is not clear why diminishing the activity of both Csn5 and Axr1 caused a synergistic defect in auxin responsiveness. Second, disruption of the Csn5 subunit compromises the integrity of the CSN complex. As CSN has been implicated in the regulation of inositol 1, 3, 4 triphosphate-5, 6 kinase (Wilson et al., J. Biol. Chem. 276:40998-41004, 2001) and an unknown protein kinase that phosphorylates p53 (Bech-Otschir et al., EMBO J. 20:1630-1639, 2001; Seeger et al., Curr. Biol. 11:R643-R646, 2001), in addition to its role in cleaving Nedd8 conjugates (Lyapina et al., Science 292:1382-1385, 2001, which is incorporated herein by reference), the observed genetic results may have arisen, for example, because altered activity of inositol 1, 3, 4 triphosphate-5, 6 kinase or the p53 kinase in Csn5-deficient plants compromised the activity of some protein that is involved in auxin signaling.

The present invention relates in general to active sites responsible for the peptidase activity, e.g., isopeptidase activity of a protein, and to screening assays for identifying agents that modulate the isopeptidase activity, such agents being useful for increasing or decreasing ubiquitin-mediated protein degradation. It is a discovery of the present invention that a polypeptide containing the JAB subunit, more specifically the JAMM domain has peptidase activity, e.g., cleavage of a peptide bond between the carboxy terminus of a modifier protein and a free amino group of a target protein. Polypeptides containing the JAB subunit, more specifically the JAMM domain can be used to treat conditions associated with the peptidase activity, screen for agents capable of modulating the peptidase activity, and identify or design compounds that are candidates for modulators of the peptidase activity.

According to the present invention, a modifier protein can be deconjugated, removed, or separated from a target protein by exposing or contacting the target protein to a polypeptide containing a subunit characterized as JAB subunit or a domain characterized as JAMM domain. The modifier protein is usually associated with a target protein via a peptide bond between the carboxy terminus of the modifier protein and a free amino group of the target protein. A free amino group generally includes, without limitation, an amino group of the amino terminus of a polypeptide or the epsilon amino group of lysine residues of a polypeptide.

According to the present invention, the JAB subunit may be the JAB1 subunit of COP9/signalsome (CSN) (see FIG. 1; SEQ ID NO:3) or the Rpn11 subunit of 26S proteasome (FIG. 1; SEQ ID NO:4). A polypeptide subunit can be characterized as JAB subunit if it has the sequence characteristics of the JAB1 or Rpn11 subunit. Normally a polypeptide subunit is deemed to have the sequence characteristics of the JAB1 or Rpn11 subunit if it contains the JAMM domain or is a homolog or ortholog of JAB1 or Rpn11 subunit. For example, FIG. 3 shows various orthologs of JAB1 from different species while FIG. 4 shows various orthologs of Rpn11 and JAB1 including an alignment of orthologs of Rpn11 and JAB1 from different species.

Polypeptides containing a subunit characterized as JAB subunit can be any known or to be discovered polypeptides, proteins, or complexes thereof. For example, the polypeptides may be a polypeptide complex of CSN containing JAB1 subunit, 26S proteasome containing Rpn11, AMSH, AMSH1, AMSH2, or C6-1A. CSN has previously been identified as a regulator of photomorphogenetic development in plants. 26S proteasome is involved in various activities, e.g., ubiquitin/26S proteasome pathway while AMSH, AMSH1, and AMSH2 are involved in cytokine signaling, TGF-β signaling, and survival of hippocampal neurons. C6-1A has been observed to be fused to the T cell receptor alpha chain gene by a chromosomal translocation in a patient with T-cell leukemia.

According to one embodiment of the invention, the deconjugation, removal, or separation of a modifier protein from a target protein is achieved by exposing or contacting the target protein to a polypeptide containing a domain characterized as the JAMM domain. The JAMM domain of the present invention includes any domain containing the amino acid sequence of HXHXXXXXXXXXXD (SEQ ID NO:1), with H being histidine, D being aspartate, and X being any amino acid. In one embodiment, the JAMM domain is any domain having an amino acid sequence of GW(Y/I)H(S/T)HPXXXXXXSXXD (SEQ ID NO:2), with G being glycine, W being tryptophan, Y being tyrosine, I being isoleucine, P being proline, S being serine, T being threonine, Y/I being either Y or I, and S/T being either S or T. In another embodiment, the JAMM domain is any domain having an amino acid sequence of $EXHyXHyHy(X)_nHX$-$HXXXXXXXXXXD$ (SEQ ID NO:13), wherein E is glutamic acid, Hy is a hydrophobic amino acid residue, and $(X)_n$ indicates about 40 to 83 amino acid residues.

In one aspect, the JAMM domain is from a human protein and has the amino acid sequence of SEQ ID NO:1. In yet another embodiment, the JAMM domain includes any domain having the same peptidase activity, e.g., isopeptidase activity of a domain containing the amino acid sequence of SEQ ID NO:1 or SEQ ID NO:2. In still another embodiment, the JAMM domain contains a metalloenzyme, e.g., metalloprotease active site and provides peptidase activity, e.g., isopeptidase activity.

One feature of the present invention provides isolated polypeptides containing a domain characterized as the JAMM domain. For example, the present invention provides an isolated polypeptide containing the JAMM domain which is not surrounded by or adjacent to any amino acid sequences that are naturally adjacent to such JAMM domain. Another feature of the present invention provides isolated crystalline polypeptides containing the JAMM domain. The crystalline polypeptides can be made by any suitable means known to one skilled in the art. For example, polypeptides containing the JAMM domain can be crystallized by equilibrating saturated solutions of the polypeptides with salts, volatile organic compounds, and other organic compounds at various controlled temperatures. Yet another feature of the present invention provides isolated monoclonal antibodies that specifically bind to an epitope within the JAMM domain. Such monoclonal antibodies can be prepared by any means known to one skilled in the art. For example, whole or partial amino acid sequences of the JAMM domain can be used as an antigen to obtain monoclonal antibodies. In one embodiment, the amino acid sequence used as antigen contains the histidine or aspartate in SEQ ID NO:1 or SEQ ID NO:2.

Polypeptides containing the JAMM domain include all known or to be discovered polypeptides, proteins, or complexes thereof. For example, Table 1 shows various polypeptides, proteins, or fragments thereof from different species that contain the JAMM domain.

TABLE 1

JAMM-Domain-Containing Proteins From Model Organisms*

Bacteria

Most bacteria encode one and some 2-4 paralogs of the DNA repair protein RadC, which is a distinct version of the JAMM domain.
In addition:
Aquifex aeolicus [aquificales] taxid 63363
gi|15606783|ref|NP_214163.1| (NC_000918) hypothetical prot . . .
Mycobacterium tuberculosis H37Rv [high GC Gram+] taxid 83332
gi|15608474|ref|NP_215850.1| (NC_000962) hypothetical prot . . .
Synechocystis sp. PCC 6803 [cyanobacteria] taxid 1148
gi|16330214|ref|NP_440942.1| (NC_000911) unknown protein[ . . .
Deinococcus radiodurans [eubacteria] taxid 1299
gi|15805429|ref|NP_294125.1| (NC_001263) conserved hypothe . . .
Pseudomonas aeruginosa [g-proteobacteria] taxid 287
gi|15595836|ref|NP_249330.1| (NC_002516) conserved hypothe . . .
gi|15597298|ref|NP_250792.1| (NC_002516) hypothetical prot . . .
Coxiella burnetii [g-proteobacteria] taxid 777
gi|10956045|ref|NP_052867.1| (NC_002131) hypothetical prot . . .
gi|1070034|emb|CAA63684.1| (X93204) orf 112 [Coxiella burn . . .
gi|10956011|ref|NP_052361.1| (NC_002118) orf 169; similari . . .
Archaea Pyrococcus abyssi [euryarchaeotes] taxid 29292
gi|14520886|ref|NP_126361.1| (NC_000868) hypothetical prot . . .
gi|14521781|ref|NP_127257.1| (NC_000868) hypothetical prot . . .
Methanothermobacter thermautotrophicus [euryarchaeotes] taxid 145262
gi|15678989|ref|NP_276106.1| (NC_000916) unknown [Methanot . . .
Halobacterium sp. NRC-1 [euryarchaeotes] taxid 64091
gi|16554503|ref|NP_444227.1| (NC_002607) Uncharacterized c . . .
gi|15789943|ref|NP_279767.1| (NC_002607) Vng0778c [Halobac . . .
Archaeoglobus fulgidus [euryarchaeotes] taxid 2234
gi|11499780|ref|NP_071023.1| (NC_000917) conserved hypothe . . .
Aeropyrum pernix [crenarchaeotes] taxid 56636
gi|14600889|ref|NP_147414.1| (NC_000854) hypothetical prot . . .
Sulfolobus solfataricus [crenarchaeotes] taxid 2287
gi|15897071|ref|NP_341676.1| (NC_002754) Hypothetical prot . . .
Eukaryotes Saccharomyces cerevisiae (baker's yeast) [fungi] taxid 4932
gi|14318526|ref|NP_116659.1| (NC_001138) Suppressor of mut . . . Rpn11p
gi|6319985|ref|NP_010065.1| (NC_001136) Hypothetical ORF; . . . Rri1p
Schizosaccharomyces pombe (fission yeast) [fungi] taxid 4896
gi|3334476|sp|P41878|PAD1_SCHPO PROTEIN PAD1/SKS1 >gi|7493 . . .
gi|1281515|pir||T44427 hypothetical protein - fission yea . . .
gi|7492119|pir||T37756 jun activation domain binding prote . . .
gi|9588467|emb|CAC00558.1|(AL390814) similarity to human . . .
Arabidopsis thaliana (thale cress) [eudicots] taxid 3702
gi|15224003|ref|NP_177279.1| (NC_003070) c-Jun coactivator . . .
gi|15219970|ref|NP_173705.1| (NC_003070) putative JUN kina . . .
gi|15237785|ref|NP_197745.1| (NC_003076) 26S proteasome, n . . .
gi|15229710|ref|NP_187736.1| (NC_003074) 26S proteasome re . . .
gi|15239230|ref|NP_196197.1| (NC_003076) 26S proteasome re . . .
gi|15218589|ref|NP_172530.1| (NC_003070) hypothetical prot . . .
gi|15221964|ref|NP_175311.1| (NC_003070) hypothetical prot . . .
gi|15231308|ref|NP_187338.1| (NC_003074) unknown protein [. . .
gi|5902365|gb|AAD55467.1|AC009322_7 (AC009322) Putative sp . . .
gi|5091556|gb|AAD39585.1|AC007067_25 (AC007067) T10O24.25 . . .
gi|6573732|gb|AAF17652.1|AC009398_1 (AC009398) F20B24.2 [A . . .
gi|5220090|ref|NP_178138.1| (NC_003070) hypothetical prot . . .
gi|5902374|gb|AAD55476.1|AC009322_16 (AC009322) Hypothetic . . .
Drosophila melanogaster (fruit fly) [flies] taxid 7227
gi|17137694|ref|NP_477442.1| (NM_058094) CSN5-P1; Drosophi . . .
gi|4732109|gb|AAD28608.1|AF129083_1 (AF129083) COP9 signal . . .
gi|6434964|gb|AAF08394.1|AF145313_1 (AF145313) 26S proteas . . .
gi|7291779|gb|AAF47199.1| (AE003464) Mov34 gene product [D . . .
gi|7301945|gb|AAF57051.1| (AE003774) CG2224 gene product [. . .
gi|7303518|gb|AAF58573.1| (AE003823) CG8877 gene product [. . .
gi|7297828|gb|AAF53077.1| (AE003631) CG4751 gene product [. . .

TABLE 1-continued

JAMM-Domain-Containing Proteins From Model Organisms* gi|6752672|gb|AAF27818.1|AF195189_1 (AF195189) yippee inte . . .
Caenorhabditis elegans [nematodes] taxid 6239
gi|17538322|ref|NP_500841.1| (NM_068440) B0547.1.p [Caenor . . .
gi|17553290|ref|NP_498470.1| (NM_066069) F37A4.5.p [Caenor . . .
gi|17535703|ref|NP_494712.1| (NM_062311) K07D4.3.p [Caenor . . .
gi|17508685|ref|NP_491319.1| (NM_058918) R12E2.3.p [Caenor . . .
Homo sapiens (human) [mammals] taxid 9606
gi|12734403|ref|XP_011713.1| (XM_011713) COP9 (constitutiv . . .
gi|5031981|ref|NP_005796.1| (NM_005805) 26S proteasome-ass . . .
gi|7243127|dbj|BAA92611.1| (AB037794) KIAA1373 protein [Ho . . .
gi|5453545|ref|NP_006454.1| (NM_006463) associated molecul . . .
gi|16158201|ref|XP_055481.1| (XM_055481) KIAA1915 protein . . .
gi|1168719|sp|P46736|C61A_HUMAN C6.1A PROTEIN >gi|2135176| . . .
gi|4581082|gb|AAD24592.1|AC007292_2 (AC007292) R31167_1, p . . .
gi|7717235|gb|AAB30469.2| (S72931) T-cell receptor alpha c . . .
gi|14249610|ref|NP_116257.1| (NM_032868) hypothetical prot . . .

*Each protein is disclosed by accession numbers used in the protein and nucleic acid sequence databases (GenBank) maintained by the National Center for Biotechnology Information (NCBI; http://www.ncbi.nlm.nih.gov).

According to the present invention, a polypeptide containing the JAB subunit or JAMM domain can additionally include any other amino acid sequences. In one embodiment, a polypeptide containing the JAB subunit or JAMM domain has other amino acid sequences that do not interfere or inhibit the peptidase activity of the JAB subunit or JAMM domain. In another embodiment, a polypeptide containing the JAB subunit or JAMM domain has other amino acid sequences that enhance or facilitate the peptidase activity of the JAB subunit or JAMM domain.

In yet another embodiment, a polypeptide containing the JAB subunit or JAMM domain has other amino acid sequences that are associated with or determine the specificity of the peptidase activity of the JAB subunit or JAMM domain. In still another embodiment, a polypeptide containing the JAB subunit or JAMM domain has other amino acid sequences that inhibit or decrease the activity of the JAB subunit or JAMM domain, and such inhibition can be released by a signal, e.g., second messenger, covalent modification, calcium or phosphorylation.

The modifier protein of the present invention can be any protein that modifies the activity or function of a target protein. In one embodiment, the modifier protein modifies a target protein through conjugation and deconjugation to the target protein, e.g., formation and cleavage of a peptide bond between the carboxy terminus of the modifier protein and a free amino group of the target protein. For example, APG12 and URM1 modifies a target protein via forming an isopeptide bond between the carboxy terminus of APG12 or URM1 and a free amino group of the target protein. A free amino group of a target protein usually includes, without limitation, an amino group of the amino terminus or epsilon amino group of lysine residues of the target protein.

One major class of modifier proteins is ubiquitin. Proteins destined for degradation may be marked by the attachment of a multiubiquitin chain to the side chains of lysine residues of the protein. Another class of modifier proteins include ubiquitin-like proteins, e.g., NEDD8, UBL1/SUMO, SMT3H2, SMT3H1, FAT10, Fau, UCRP/ISG15, or UBL5. In one embodiment, the modifier protein of the present invention includes any protein containing two glycine amino acids at its carboxy terminus after being processed.

The target protein of the present invention can be any protein whose activity or function is modified by a modifier protein. In one embodiment, a target protein is a protein which forms a peptide bond with a modifier protein, e.g., a peptide bond between the carboxy terminus of the modifier protein and a free amino group of the target protein. In another embodiment, a target protein is specific to a class of modifier proteins.

For example, the target protein of the present invention may be cullin proteins such as Cul1, Cul2, Cul3, Cul4A, Cul4B, and Cul5, which are known to be the target proteins of Nedd8. In one embodiment, the target protein of the present invention includes any protein having ubiquitin ligase activity or is part of a protein complex having ubiquitin ligase activity. In another embodiment, the target protein of the present invention includes any protein to which ubiquitin conjugates for processing or degradation, e.g., p53, IκB, NF-κB, β-adrenergic receptor, cyclin E, $p27^{Kip1}$, etc.

According to one embodiment of the present invention, the target protein used in the screening assays provided by the present invention can be any protein that produces a detectable signal upon deconjugation, removal, or separation from its modifier protein. Such detectable signal can be any assayable signal including, without limitation, enzymatic, spectroscopic, fluorescent, or functional signals, or a signal produced upon specific molecular interaction. For example, the target protein can be an enzyme such as peroxidase, alkaline phosphatase, and luciferase. The target protein can also be a fluorescent protein obtained via protein modification or a naturally fluorescent protein including, without limitation green fluorescent protein, yellow fluorescent protein, cyan fluorescent protein, dsRed, and the derivatives thereof.

In one embodiment, the target protein of the present invention is used in the screening assays of the present invention with a 26S proteasome and may be any protein that can structurally fit or refold within the inner chamber of a 20S proteasome. Normally the inner chamber of a 20S proteasome can structurally accommodate any protein that is 70 kDa or less.

According to the present invention, a target protein is deconjugated, removed, or separated from its modifier protein by being exposed or contacted to a polypeptide having the JAB subunit or JAMM domain. Such exposure or contact may be in vivo via administering the polypeptide to a subject in need of such treatment or in vitro via incubating the polypeptide with the target protein. In one embodiment, an inhibitor of a polypeptide having the JAB subunit or JAMM domain can be used to increase the association of a modifier protein to a target protein in vitro or in vivo.

According to another aspect of the invention, a polypeptide having the JAB subunit or JAMM domain, or a protein comprising such a polypeptide (e.g., CSN, or a proteasome comprising an Rpn11 polypeptide) can be used for screening assays for agents that affect the deconjugation, removal, or separation of a modifier protein from a target protein. The screening assays provided by the present invention can be carried out by incubating in the presence and absence of a test agent, a target protein, e.g., conjugated with a modifier protein and a polypeptide containing the JAB subunit or JAMM domain, and determining the effect of the test agent. In one embodiment, the screening assays provide a means to identify an agent that modulates (i.e., increases or decreases) the isopeptidase activity of a polypeptide comprising a JAMM domain (e.g., deneddylation activity), or of a protein comprising such a polypeptide.

Generally, an increase or decrease in the amount of the target protein not conjugated to the modifier protein caused by the test agent is indicative of an agent capable of affecting deconjugation, removal, or separation of the modifier protein from the target protein. For example, a test agent decreasing the amount of the target protein not conjugated to the modifier protein is indicative of an agent decreasing the deconjugation of the modifier protein from the target protein.

In one embodiment, the polypeptide (protein) used in the screening assays provided by the present invention is a polypeptide complex of 26S proteasome while the modifier protein is ubiquitin. The polypeptide complex of 26S proteasome can be obtained by any suitable means available in the art. For example, 26S proteasome can be purified from eukaryotic cells or tissues, e.g., S. cerevisiae or human.

In another embodiment, the incubation in the presence and absence of a test agent, a target protein, and 26S proteasome of the screening assays provided by the present invention is carried out in the presence of a 20S inhibitor or an inhibitor of the degradation process associated with the deubiquitination process of the 26S proteasome pathway. Any 20S inhibitor or inhibitor of the degradation process can be used for the purpose of the present invention. For example, a 20S inhibitor can be MG132, lactacystin, epoxomycin, PS-349, PS-519, LLnL, or the derivatives thereof. In general, such inhibitor prevents or decreases the degradation of a target protein that is not conjugated to a modifier protein, e.g., ubiquitin.

In yet another embodiment, the incubation is conducted further in the presence of an energy source, e.g., ATP. In still another embodiment, the incubation is conducted further in the presence of an inhibitor of deubiquitination by a conventional ubiquitin isopeptidase, e.g., an ubiquitin isopeptidase other than those that associated with a JAB subunit such as 26S proteasome. One example of such inhibitor is ubiquitin aldehyde, e.g., at 2-5 μM.

The test agent used for the screening methods of the present invention can be any agent from any library of compounds or molecules. In one embodiment, the test agent is selected or derived from compounds likely to inhibit the activity of metalloproteinase, e.g., compounds having zinc-binding functionality. For example, the test agent can be any compounds having a hydroxamate moiety or a member of a hydroxamate compound library, reverse hydroxamate compound library, thiol compound library, carboxylate compound library, or phosphinic acid compound library.

A screening method of the invention conveniently can be adapted to high throughput analysis and, therefore, can be used to screen combinatorial libraries of test agents, which can be a library of random test agents, biased test agents, or variegated test agents (see, for example, U.S. Pat. No. 5,571,698, which is incorporated herein by reference), in order to identify those agents that can modulate an isopeptidase activity of a polypeptide comprising a JAMM domain and, therefore, ubiquitin-mediated protein degradation in a cell. Methods for preparing a combinatorial library of molecules that can be tested for a desired activity are well known in the art and include, for example, methods of making a phage display library of peptides, which can be constrained peptides (see, for example, U.S. Pat. No. 5,622,699; U.S. Pat. No. 5,206,347; Scott and Smith, *Science* 249:386-390, 1992; Markland et al., *Gene* 109:13-19, 1991; each of which is incorporated herein by reference); a peptide library (U.S. Pat. No. 5,264,563, which is incorporated herein by reference); a library of peptide derivative compounds such as a hydroxamate compound library, reverse hydroxamate compound library, a carboxylate compound library, thiol compound library, a phosphinic peptide library, or phosphonate compound library (see, for example, Dive et al., *Biochem. Soc. Trans.* 28:455-460, 2000; Ye and Marshall, *Peptides: The Wave of the Future* (Lebl and Houghten, ed.; American Peptide Society, 2001), each of which is incorporated herein by reference); a peptidomimetic library (Blondelle et al., *Trends Anal. Chem.* 14:83-92, 1995, which is incorporated herein by reference); incorporated herein by reference); a nucleic acid library (O'Connell et al., *Proc. Natl. Acad. Sci., USA* 93:5883-5887, 1996; Tuerk and Gold, *Science* 249:505-510, 1990; Gold et al., *Ann. Rev. Biochem.* 64:763-797, 1995; each of which is incorporated herein by reference); an oligosaccharide library (York et al., *Carb. Res.* 285:99-128, 1996; Liang et al., *Science* 274:1520-1522, 1996; Ding et al., *Adv. Expl. Med. Biol.* 376:261-269, 1995; each of which is incorporated herein by reference); a lipoprotein library (de Kruif et al., *FEBS Lett.* 399:232-236, 1996, which is incorporated herein by reference); a glycoprotein or glycolipid library (Karaoglu et al., *J. Cell Biol.* 130:567-577, 1995, which is incorporated herein by reference); or a chemical library containing, for example, drugs or other pharmaceutical agents (Gordon et al., *J. Med. Chem.* 37:1385-1401, 1994; Ecker and Crooke, *Bio Technology* 13:351-360, 1995; each of which is incorporated herein by reference).

Peptides and peptide derivatives can be useful as agents for modulating isopeptidase activity of a polypeptide comprising a JAMM domain, or as test agents to screen for such activity. Such peptides (or test agent peptides) can contain one or more D-amino acids and/or L-amino acids; and/or one or more amino acid analogs, for example, an amino acid that has been derivatized or otherwise modified at its reactive side chain. In addition, one or more peptide bonds in the peptide can be modified, and a reactive group at the amino terminus or the carboxy terminus or both can be modified. Peptides containing D-amino acids, or L-amino acid analogs, or the like, can have improved stability to a protease, an oxidizing agent or other reactive material the peptide may encounter in a biological environment, and, therefore, can be particularly useful in performing a method of modulating isopeptidase activity of a polypeptide comprising a JAMM domain as disclosed herein. Of course, the peptides can be modified to have decreased stability in a biological environment, if desired, such that the period of time the peptide is active in the environment is reduced.

Peptide derivatives comprising hydroxamate bonds or phosphinic bonds can be particularly useful for modulating isopeptidase activity of a polypeptide comprising a JAMM domain because the hydroxamate or phosphinic bonds of such peptide derivatives can coordinate with metal ions in polypeptides such as metalloproteases, thus inhibiting the activity of the metalloproteases (see, for example, Dive et al., supra, 2000; Ye and Marshall, supra, 2001). As such, hydroxamate and/or phosphinic peptide derivatives can be screened to identify those that similarly can reduce or inhibit isopeptidase activity of a polypeptide comprising a JAMM domain.

Test agents also can be antibodies that are raised against and specifically bind one or more epitopes of a polypeptide comprising a JAMM domain, particularly to an epitope associated with the isopeptidase activity of the polypeptide. As used herein, the term "antibody" is used in its broadest sense to include polyclonal and monoclonal antibodies, as well as antigen binding fragments of such antibodies. The term "binds specifically" or "specific binding activity" or the like, when used in reference to an antibody, means that an interaction of the antibody and a particular epitope has a dissociation constant of at least about $1 \times 10^{-6}$ M, generally at least about $1 \times 10^{-7}$ M, usually at least about $1 \times 10^{-8}$ M, and particularly at least about $\times 10^{-9}$ M or $1 \times 10^{-10}$ M or less. As such, Fab, F(ab')$_2$, Fd and Fv fragments of an antibody that retain specific binding activity are included within the definition of an antibody. In addition to specifically binding a particular epitope, an antibody agent can modulate the isopeptidase activity of a polypeptide comprising a JAMM domain, including increasing or decreasing such activity.

The term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains (see Huse et al., *Science* 246:1275-1281, 1989, which is incorporated herein by reference). These and other methods of making, for example, chimeric, humanized, CDR-grafted, single chain, and bifunctional antibodies are well known (Winter and Harris, *Immunol. Today* 14:243-246, 1993; Ward et al., *Nature* 341:544-546, 1989; Harlow and Lane, *Antibodies: A laboratory manual* (Cold Spring Harbor Laboratory Press, 1988); Hilyard et al., *Protein Engineering: A practical approach* (IRL Press 1992); Borrabeck, *Antibody Engineering*, 2d ed. (Oxford University Press 1995); each of which is incorporated herein by reference).

A panel of test agent antibodies conveniently can be obtained by immunizing an animal using a peptide portion of a polypeptide that has isopeptidase activity and comprises a JAMM domain, for example, a JAB1 polypeptide. Where such a peptide is non-immunogenic, it can be made immunogenic by coupling the hapten to a carrier molecule such as bovine serum albumin (BSA) or keyhole limpet hemocyanin (KLH), or by expressing the peptide portion as a fusion protein. Various other carrier molecules and methods for coupling a hapten to a carrier molecule are well known in the art (see, for example, by Harlow and Lane, supra, 1988). Methods for raising polyclonal antibodies, for example, in a rabbit, goat, mouse or other mammal, are well known in the art (see, for example, Green et al., "Production of Polyclonal Antisera," in *Immunochemical Protocols* (Manson, ed., Humana Press 1992), pages 1-5; Coligan et al., "Production of Polyclonal Antisera in Rabbits, Rats, Mice and Hamsters," in *Curr. Protocols Immunol.* (1992), section 2.4.1; each or which is incorporated herein by reference). In addition, monoclonal antibodies can be obtained using methods that are well known and routine in the art (see, for example, Kohler and Milstein, *Nature* 256:495, 1975, which is incorporated herein by reference; see, also, Harlow and Lane, supra, 1988). For example, spleen cells from a mouse immunized with a polypeptide comprising a JAMM domain, or an epitopic fragment thereof, can be fused to an appropriate myeloma cell line such as SP/02 myeloma cells to produce hybridoma cells. Cloned hybridoma cell lines can be screened using labeled antigen to identify clones that secrete monoclonal antibodies having the appropriate specificity, and hybridomas expressing antibodies having a desirable specificity and affinity can be isolated and utilized as a continuous source of the antibodies. A recombinant phage that expresses, for example, a single chain antibody that modulates the isopeptidase activity of a polypeptide comprising a JAMM domain also provides an antibody that can used for preparing standardized kits.

Monoclonal antibodies can be isolated and purified from hybridoma cultures by a variety of well established techniques, including, for example, affinity chromatography with Protein-A SEPHAROSE gel, size exclusion chromatography, and ion exchange chromatography (Coligan et al., supra, 1992, see sections 2.7.1-2.7.12 and sections 2.9.1-2.9.3; see, also, Barnes et al., "Purification of Immunoglobulin G (IgG)," in *Meth. Molec. Biol.* 10:79-104 (Humana Press 1992), which is incorporated herein by reference). Methods of in vitro and in vivo multiplication of monoclonal antibodies are well known in the art. Multiplication in vitro can be carried out in suitable culture media such as Dulbecco's Modified Eagle Medium or RPMI 1640 medium, optionally replenished by a mammalian serum such as fetal calf serum or trace elements and growth sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo can be carried out by injecting cell clones into mammals histocompatible with the parent cells, for example, syngeneic mice, to cause growth of antibody producing tumors. Optionally, the animals are primed with a hydrocarbon, especially oils such as pristane (tetramethylpentadecane) prior to injection. After one to three weeks, the desired monoclonal antibody is recovered from the body fluid of the animal.

As disclosed herein, therapeutic applications for agents, including antibody agents, identified according to a screening assay of the invention also are provided. Where the therapeutic procedure is for treating a human subject, the antibodies can be derived from a subhuman primate antibody (see, for example, Goldenberg et al., Intl. Publ. WO 91/11465, 1991; and Losman et al., *Intl. J. Cancer* 46:310, 1990, each of which is incorporated herein by reference). A therapeutically useful antibody for human treatment also can be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are known (see, for example, Orlandi et al., *Proc. Natl. Acad. Sci., USA* 86:3833, 1989, which is hereby incorporated in its entirety by reference). Techniques for producing humanized monoclonal antibodies also are known (see, for example, Jones et al., *Nature* 321:522, 1986; Riechmann et al., *Nature* 332:323, 1988; Verhoeyen et al., *Science* 239:1534, 1988; Carter et al., *Proc. Natl. Acad. Sci., USA* 89:4285, 1992; Sandhu, *Crit. Rev. Biotechnol.* 12:437, 1992; and Singer et al., *J. Immunol.* 150:2844, 1993; each of which is incorporated herein by reference). Alternatively, the antibodies can be derived from human antibody fragments isolated from a combinatorial immunoglobulin library (see, for example, Barbas et al., *METHODS: A Companion to Methods in Immunology* 2:119, 1991; Winter et al., *Ann. Rev. Immunol.* 12:433, 1994; each of which is incorporated herein by reference).

The antibodies also can be derived from human monoclonal antibodies, which, for example, can be obtained from transgenic mice that have been genetically modified to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are well known (see, for example, by Green et al., *Nature Genet.* 7:13, 1994; Lonberg et al., *Nature* 368:856, 1994; and Taylor et al., *Intl. Immunol.* 6:579, 1994; each of which is incorporated herein by reference), and commercial sources of human antibodies are available (Abgenix, Inc.; Fremont Calif.).

Polynucleotides also can be useful as agents that can modulate isopeptidase activity of a polypeptide comprising a JAMM domain because nucleic acid molecules having binding specificity for cellular targets, including cellular polypeptides, exist naturally, and because synthetic molecules having such specificity can be readily prepared and identified (see, for example, U.S. Pat. No. 5,750,342, which is incorporated herein by reference). The term "polynucleotide" is used broadly herein to mean a sequence of two or more deoxyribonucleotides or ribonucleotides that are linked together by a phosphodiester bond. As such, the term "polynucleotide" includes RNA and DNA, which can be a gene or a portion thereof, a cDNA, a synthetic polydeoxyribonucleic acid sequence, or the like, and can be single stranded or double stranded, as well as a DNA/RNA hybrid. A polynucleotide can be a naturally occurring nucleic acid molecule, which can be isolated from a cell, or a synthetic molecule, which can be prepared, for example, by methods of chemical synthesis or by enzymatic methods such as by the polymerase chain reaction (PCR).

A polynucleotide agent (or test agent) can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22:5220-5234, 1994; Jellinek et al., *Biochemistry* 34:11363-11372, 1995; Pagratis et al., *Nature Biotechnol.* 15:68-73, 1997, each of which is incorporated herein by reference).

The covalent bond linking the nucleotides of a polynucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., *Nucl. Acids Res.* 22:977-986, 1994; Ecker and Crooke, *Bio Technology* 13:351360, 1995, each of which is incorporated herein by reference). The incorporation of non-naturally occurring nucleotide analogs or bonds linking the nucleotides or analogs can be particularly useful where the polynucleotide is to be exposed to an environment that can contain a nucleolytic activity, including, for example, a tissue culture medium or upon administration to a living subject, since the modified polynucleotides can be less susceptible to degradation.

A polynucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995).

According to another aspect of the present invention, the JAMM domain can be used for rational drug design or as a guide for identifying agents that are capable of affecting the activity of the JAMM domain or any polypeptide containing the JAMM domain, e.g., identify inhibitors of the JAMM domain. In one embodiment, the structure coordinates or atomic coordinates of the JAMM domain or any polypeptide containing the JAMM domain are used to design a potential inhibitor that will form a covalent or non-covalent bond with one or more amino acids within the JAMM domain or metal ions bound by the JAMM domain. In another embodiment, the potential inhibitor is designed to form a covalent bond or non-covalent bond with histidine or aspartate of the JAMM domain. Such designed potential inhibitor can be synthesized by any suitable means and be tested for their ability to inhibit the activity, e.g., peptidase activity of the JAMM domain.

The structure or atomic coordinates of the JAMM domain or a polypeptide containing the JAMM domain refer to mathematical coordinates derived from mathematical equations related to the patterns obtained on diffraction of a monochromatic beam of X-rays by the atoms (scattering centers) of the JAMM domain or the polypeptide containing the JAMM domain in crystal form. The diffraction data normally are used to calculate an electron density map of the repeating unit of the crystal. The electron density maps are generally used to establish the positions of the individual atoms within the unit cell of the crystal.

Various methods can be used to obtain the structure or atomic coordinates of the JAMM domain or a polypeptide containing the JAMM domain. For example, three dimensional diffraction data for a polypeptide containing the JAMM domain can be collected at temperatures ranging from 100-274 K using an area detector and radiation from a rotating-anode X-ray generator and from the Stanford synchrotron. These data, along with data collected from a heavy atom derivative of the polypeptide, can be processed and the structure can be solved by methods which make use of the isomorphous differences between a derivative and native polypeptide and/or make use of the anomalous X-ray scattering from the heavy atom in the derivative. In one embodiment, the structure or atomic coordinates of one JAMM containing polypeptide can be solved by using the phases of another JAMM containing polypeptide structure or sections thereof that has already been previously determined. High resolution data sets can be solved by direct methods.

Based on the three dimensional crystal structure of a JAMM domain polypeptide from *Archaeglobulus fulgidis* (GenBank Acc. No. AF21980; see, also, Cope et al., supra, 2002). The structure confirmed that the two histidine residues and the aspartic acid residue as set forth in the HXHXXXXXXXXXXD (SEQ ID NO:1) sequence of the JAMM domain act to coordinate zinc metal ion binding to a polypeptide comprising the JAMM domain; the metal ion binding is required for isopeptidase activity. In addition, an extended structure having an amino acid sequence EXHyX-HyHy(X)$_n$H(S/T)HXXXXXXXXSXXD (SEQ ID NO:66), which comprises the JAMM domain (SEQ ID NO:1), was determined to contribute to the structure of the metal ion coordinating site. As disclosed herein, mutation of the upstream glutamic acid residue resulted in a loss of isopeptidase activity of Csn5, thus demonstrating that this residue is essential to the isopeptidase activity. With respect to the three dimensional structure of the isopeptidase, the glutamate residue binds to the hydrogen atoms of a water molecule, whose oxygen atom is bound to the zinc ion immobilized within the JAMM domain (see SEQ ID NO:66). The first serine residue (or the threonine residue, when present) as shown in SEQ ID NO:66 appears to interact via its hydroxyl group side with the main chain amide of the upstream glutamic acid residue. In addition, the second serine residue as set forth in SEQ ID NO:66 appears to interact with the main chain amide of the down stream aspartic acid residue; or with the glutamic acid residue as set forth in SEQ ID NO:66. As such, these results provide targets for rational design of potential inhibitors of isopeptidase activity, including, for example, designing small molecules, peptides, peptide derivatives, or other molecules that interact with one or more of the above-described histidine, aspartic acid, serine, threonine (when present), and glutamic acid residues (see, for example, SEQ ID NO:66).

According to another aspect of the present invention, any agent that is capable of inhibiting or decreasing the deconjugation, removal, or separation of a modifier protein from a target protein can be used therapeutically to treat various conditions associated with protein regulation, e.g., deubiquitination or deneddylation. For example, any agent identified by the screening methods of the present invention that is able to decrease the deconjugation of a modifier protein from a target protein, e.g., an inhibitor of the isopeptidase activity of 26S proteasome can be used therapeutically to treat a subject having a condition such as a neoplastic growth, infection, chronic inflammation, asthma, ischemia and reperfusion injury, multiple sclerosis, rheumatoid arthritis, or psoriasis; or to treat a subject in whom it is desired to modulate angiogenesis, including, for example, the angiogenesis associated with a condition such as tumor growth.

An agent useful for therapeutic treatment can be administered alone, in a composition with a suitable pharmaceutical carrier, or in combination with other therapeutic agents. A particularly effective combination of agents includes a first agent that modulates (i.e., increases or decreases) the isopeptidase activity of a polypeptide comprising a JAMM domain, e.g., a JAB domain of a CSN complex, and a second agent that similarly modulates (i.e., increases or decreases, respectively) a component of a protein degradation pathway that includes the polypeptide comprising the JAMM domain, particularly a component such as an E2 ubiquitin conjugating enzyme (e.g., Cdc34 or Ubc) or E3 ubiquitin ligase (e.g., SCF). Whereas previous data suggested that a CSN isopeptidase mutant likely would suppress the effect of an SCF mutant, as disclosed herein, the opposite effect occurs, i.e., inhibition of the CSN isopeptidase activity synthetically enhances an SCF mutant (see Example 4). As such, a particularly effective combination of agents for inhibiting protein degradation can include, for example, a first agent that reduces or inhibits the isopeptidase activity of a polypeptide comprising a JAMM domain and a second agent that reduces or inhibits the activity of an E3 ubiquitin ligase such as SCF. For example, a particularly effective combination of agents can include a first agent that reduces or inhibits the isopeptidase activity of a JAB domain of a CSN complex, and a second agent that reduces or inhibits F-box protein binding to the Skp1 domain of an E3 such as an SCF complex comprising the F-box protein and Skp1 domain, or a second agent that reduces or inhibits F-box protein binding to a substrate targeted for degradation, or a second agent that reduces or inhibits the interaction of Skp1 with Cul1; or a second agent that reduces or inhibits the charging of ubiquitin to a Ubc (E2) polypeptide that works together with SCF (e.g., UbcH5 or Cdc34), or otherwise inhibits the ability of the Ubc polypeptide to transfer ubiquitin to a substrate polypeptide bound to the F-box subunit of SCF.

An effective amount of an agent or combination of agents to be administered can be determined on a case-by-case basis. Factors to consider include, for example, age, body weight, stage of the condition, other disease conditions, duration of the treatment, and the response to the initial treatment. Typically, the agents are prepared as an injectable, either as a liquid solution or suspension. However, solid forms suitable for solution in, or suspension in, liquid vehicles prior to injection can also be prepared. The agent can also be formulated into an enteric-coated tablet or gel capsule according to known methods in the art.

The agents of the present invention may be administered in any way that is medically acceptable which may depend on the disease condition or injury being treated. Possible administration routes include injections, by parenteral routes such as intravascular, intravenous, intraepidural or others, as well as oral, nasal, ophthalmic, rectal, topical, or pulmonary, e.g., by inhalation. The agents may also be directly applied to tissue surfaces, e.g., during surgery. Sustained release administration is also specifically included in the invention, by such means as depot injections or erodible implants.

The following examples are intended to illustrate but not to limit the invention in any manner, shape, or form, either explicitly or implicitly. While they are typical of those that might be used, other procedures, methodologies, or techniques known to those skilled in the art may alternatively be used.

EXAMPLE 1

Deubiquitination by 26S Proteasome

To demonstrate that an isopeptidase activity associated with the 26S proteasome can deubiquitinate a target polypeptide in vitro, experiments were conducted to incubate multiubiquitinated Sic1 substrate (300 nM) for 0 or 5 min at 25° C. in the presence of purified 26S proteasome (100 nM), epoxomicin (100 μM), and ubiquitin aldehyde (5 μM).

Epoxomicin was included to uncouple the deubiquitination and degradation of a substrate by the 26S proteasome, since these two processes are normally tightly coupled. Epoxomicin forms a covalent adduct with the catalytically active N-terminal threonine residues of beta subunits of the 20S proteasome, thereby eliminating the proteolytic activity of this particle. At the end of the incubation, samples were supplemented with SDS-PAGE sample buffer, fractionated on an SDS-polyacrylamide gel, transferred to nitrocellulose, and immunoblotted with antibodies directed against Sic1. Filter-bound antibodies were decorated with goat-anti-rabbit antibody conjugated to horse radish peroxidase and visualized with ECL reagents.

This experiment demonstrated that inhibition of 20S peptidase activity is required to observe the production of deubiquitinated Sic1 by 26S proteasome. In the absence of epoxomicin, ubiquitinated Sic1 was completely degraded by the 26S proteasome. In the presence of epoxomicin, Sic1 was not degraded, but a majority of Sic1 was deubiquitinated such that the input substrate was converted from a heterogeneous smear of greater 220 kDa to a discrete species of about 50 kDa, which corresponds to Sic1 lacking any covalently attached ubiquitin molecules.

To test if this reaction is dependent upon ATP, multi-ubiquitinated Sic1 substrate (300 nM) and purified 26S proteasome (100 nM) were incubated in the presence or absence of epoxomicin (100 μM), glucose (30 mM) plus hexokinase (5 U/ml), apyrase (15 U/ml), and ubiquitin vinyl sulfone (Ub-PVS; 2.5 μM) as indicated.

This experiment revealed that ATP is required to observe the deubiquitination of target polypeptide by purified 26S proteasome. Specifically, in the presence of multi-ubiquitinated Sic1 substrate, 26S proteasome (which contains ATP), and epoxomicin, the input substrate was converted from a heterogeneous smear of >220 KD to a discrete species of ~40 KD, which corresponds to Sic1 lacking any covalently attached ubiquitin molecules. However, in the additional presence of apyrase or glucose plus hexokinase (both of which consume ATP), no deubiquitination of the multi-ubiquitinated Sic1 substrate was observed. This reaction was not sensitive to ubiquitin vinyl sulfone, which is an inhibitor of conventional ubiquitin isopeptidases.

These results demonstrate that the 26S proteasome recognizes a ubiquitinated substrate, and begins to translocate it into the internal cavity of the 20S proteasome, where it is degraded. As the substrate is being translocated into the 20S proteasome, the ubiquitin chains are removed by a previously unknown isopeptidase in the 26S proteasome. Under normal circumstances this isopeptidase activity is not detected because substrate degradation and removal of the ubiquitin chains occurs contemporaneously. However, in the presence of an inhibitor of the 20S peptidases, the substrate is completely deubiquitinated and translocated into the central cavity of the 20S proteasome, but is not degraded. As such, the deubiquitinated product was readily detectable.

Mass spectrometric analysis of affinity-purified yeast 26S proteasome that is active in deubiquitinating Sic1 revealed only a single deubiquitinating enzyme, Ubp6 (Verma et al., supra, 2000). However, 26S proteasome purified from a ubp6Δ mutant yeast strain and assayed as described above was fully competent to deubiquitinate multi-ubiquitinated Sic1 to yield Sic1 lacking any covalently attached ubiquitin molecules.

The above demonstrations enable an assay in which the substrate is observed to be converted from a ubiquitinated molecule to a deubiquitinated molecule. Such conversion can be monitored, for example, by detecting the removal of a multi-ubiquitin chain from a protein based on a change in an enzymatic, spectroscopic, fluorescent, or molecular interaction properties of the ubiquitinated protein. For example, a protein that emits light e.g., luciferase, will be made inactive due to the attachment of multi-ubiquitin chains.

The multi-ubiquitin chains will be attached by enzymatic, chemical, molecular genetic, or a combination of these methods. The cleavage of ubiquitin chains from the inactive luciferase substrate as it is being translocated into the inner cavity of the 20S proteasome in the presence of a 20S peptidase inhibitor will enable the luciferase to fold and thereby acquire the ability to emit light upon ATP hydrolysis.

The inner chamber of the 20S proteasome can accommodate a folded protein of approximately 70 kD. Therefore, any protein domain less than 70 kD whose enzymatic, spectroscopic, fluorescent, or molecular interaction properties can be reversibly altered by attachment of ubiquitin or a multi-ubiquitin chain can be used as a substrate to monitor ubiquitin isopeptidase activity of the 26S proteasome based on the methods that are disclosed herein.

Inhibition of the ability of the 26S proteasome to degrade proteins by blockage of ubiquitin isopeptidase activity would be useful for treating cancer, ischemia and reperfusion injury, and diseases characterized by excessive inflammation or autoimmune responses, including, for example, asthma, rheumatoid arthritis, psoriasis, and multiple sclerosis.

To test whether the deconjugation of ubiquitin from a substrate protein is required for its degradation, the degradation of an ubiquitin-proteasome pathway substrate was examined in cells deficient in Rpn11-associated metalloprotease activity. A set of four congenic strains was generated, including 1) MPR (wild type), 2) mpr1-1, 3) mpr1-1 harboring an integrated copy of RPN11 in which the codons for histidine 109 and 111 have been mutated to alanine (mpr1-1 leu2::LEU2-rpn11 AxA), and 4) mpr1-1 harboring an integrated copy of wild type RPN11 (mpr1-1 leu2::LEU2-RPN11). mpr1-1 is a temperature-sensitive allele of RPN11, and complementation tests demonstrated that wild type RPN11 but not rpn11 AxA complemented the temperature-sensitive growth defect of mpr1-1.

Each of these strains was transformed with a plasmid that encodes $Ub^{V76}Val-e^{\Delta K}-\beta Gal$, which is an unstable protein that is degraded via the ubiquitin-proteasome pathway. All strains were pulse-radiolabeled with $^{35}S$-Translabel® probe for 5 min at 37° C., then at time 0 a chase was initiated by addition of 10 mM cold methionine and 500 μg/ml cycloheximide. At 7, 14, and 22 min following the initiation of chase, aliquots of the culture were removed and processed for immunoprecipitation with antibodies directed against β-galactosidase. Immunoprecipitated proteins were fractionated by SDS-PAGE and visualized by autoradiography.

The results demonstrated that the normally unstable $Ub^{V76}Val-e^{\Delta K}-\beta Gal$ reporter was dramatically stabilized in mpr1-1 cells. Rapid turnover of the test protein in mpr1-1 cells was restored by an integrated copy of RPN11, but not rpn11 AxA. Thus, the metalloprotease active site of Rpn11 was required for rapid turnover of proteins by the ubiquitin-proteasome pathway in vivo.

This result was confirmed in vitro. Purified 26S proteasomes that lack critical metalloprotease active site residues of Rpn11 were unable to deubiquitinate and degrade ubiquitinated Sic1. 26S proteasomes were affinity-purified from *Saccharomyces cerevisiae* cells in which the PRE1 gene was modified to encode a Pre1 polypeptide tagged with a FLAG epitope (Verma et al., supra, 2000).

Wild type 26S proteasome was purified from a strain with the genotype pre1::PRE1-FLAG-HIS6 (URA3) his3-11 ade2-1 112 trp1-Δ2 can1-100, mpr1-1, leu2::LEU2-RPN11, and mutant 26S proteasome was purified from a strain with the genotype pre1::PRE1-FLAG-HIS6 (URA3) his3-11 ade2-1 112 trp1-Δ2 can1 -100 mpr1-1, leu2::LEU2-rpn11AXA.

Purified proteasomes were evaluated by immunoblotting with antibodies directed against *Schizosaccharomyces pombe* Pad1, which cross-reacted with Rpn11. Wild type and point mutant Rpn11 polypeptides were readily distinguished from Mpr1-1 polypeptide, because the latter is truncated due to a frameshift mutation. The immunoblot analysis revealed that both wild type and mutant proteasomes contained only full-length Rpn11 polypeptide, and none of the truncated Mpr1-1 polypeptide was detected. Thus, the results are directly attributable to the properties of the Rpn11 and Rpn11AxA proteins since no Mpr1-1 protein was present. Mass spectrometric analysis confirmed that the wild type and mutant proteasomes were of equal composition, and all subunits were present.

To evaluate their activity, wild type and Rpn11AxA mutant 26S proteasomes (100 nM) were incubated with ubiquitinated Sic1 (300 nM) plus ATP (2 mM) in the presence or absence of 00 μM epoxomicin for 0 or 5 min at 25° C. Reactions were terminated by the addition of SDS-PAGE sample buffer, fractionated by SDS-PAGE, transferred to nitrocellulose, and immunoblotted with antibodies directed against Sic1. Filter-bound antibodies were decorated with goat-anti-rabbit antibody conjugated to horse radish peroxidase and visualized with ECL reagents.

The results demonstrate that mutant proteasomes were unable to degrade multi-ubiquitinated Sic1 even in the absence of epoxomicin, and were unable to deubiquitinate multiubiquitinated Sic1 (i.e., to convert multiubiquitinated Sic1 from a heterogeneous smear of greater than about 220 kDa to a discrete species of about 40 kDa, which corresponds to Sic1 lacking any covalently attached ubiquitin molecules) in the presence of epoxomicin.

EXAMPLE 2

Deneddylation by COP9 Signalsome (CSN)

To identify a putative active site within the CSN complex that can mediate cleavage of Nedd8-cullin conjugates, all eight known subunits of the CSN were subjected to sequence analysis by computer. Detailed inspection revealed that the Jab1 subunit contains conserved histidine residues and a conserved aspartic acid that are reminiscent of zinc-coordinating residues in a metallo-β-lactamase. An alignment of these residues is presented in FIG. 3.

On the basis of this analysis, it was hypothesized that CSN represents the founding member of a novel class of metalloproteases. To test this hypothesis, the effect of a divalent cation chelator on the Nedd8 conjugate cleavage activity associated with CSN was examined. Mutant csn5Δ *S. pombe* cell extract that contained neddylated Pcu1 was incubated either alone (−) or following addition (+) of wild type lysate (which contained active CSN) supplemented with either methanol vehicle (MeOH), 1 mM 1,10-phenanthroline (O-PT), or 1 mM, 10 mM, or 20 mM EDTA.

Reactions were incubated 30 min at 30° C. and terminated by addition of SDS-PAGE sample buffer, fractionated by SDS-PAGE, transferred to nitrocellulose, and immunoblotted with antibodies directed against *S. pombe* Cul1. Filter-bound antibodies were decorated with goat-anti-rabbit antibody conjugated to horse radish peroxidase and visualized with ECL reagents (Lyapina et al., supra, 2001).

No inhibition was detected with 1 mM EDTA; less than 50% inhibition was observed with 10 mM EDTA; and almost complete inhibition occurred with 20 mM EDTA, wherein "inhibition" means that Nedd8 was not deconjugated from Cul1 upon addition of CSN and "no inhibition" means that Nedd8 was efficiently deconjugated from Cul1 upon addition of CSN. The status of Nedd8 conjugation to Cul1 was determined by the mobility of Cul1 on the SDS-polyacrylamide gel. Nedd8-conjugated Cul1 migrated more slowly than unmodified Cul.

Some metal-dependent enzymes are relatively insensitive to inhibition by EDTA, but are nevertheless potently inhibited by the chelator 1,10-phenanthroline, which, at 1 mM, completely inhibited the Nedd8 conjugate cleavage activity of CSN. These results indicate that CSN is a metalloprotease.

To further confirm the hypothesis that arose from the sequence analysis, the conserved histidine residues and aspartic acid in *S. pombe* csn5+ were individually mutated, and the ability of each point-mutated gene to complement the cullin deneddylation defect of a csn5Δ mutant was examined (Lyapina et al., supra, 2001; Zhou et al., *BMC Biochemistry* 2:7, 2001, which is incorporated herein by reference). Wild type *S. pombe* csn5+ and the indicated mutant derivatives were inserted into the *S. pombe* expression vector pREP41 and transfected into *S. pombe* csn5Δ cells.

Transformants were evaluated for modification state of Pcu1 by fractionating cell extracts on an SDS-polyacrylamide gel, transferring fractionated proteins to nitrocellulose, and immunoblotting with antibodies directed against *S. pombe* Cul1. Filter-bound antibodies were decorated with goat-anti-rabbit antibody conjugated to horse radish peroxidase and visualized with ECL reagents.

csn5Δ cells containing an empty vector accumulated Pcu1 exclusively in the Nedd8-modified form. This accumulation was reversed upon expression of wild type csn5+, but not the H118A, H120A, or D131 N mutants. Thus, the putative active site residues identified by computer analysis are absolutely required for CSN activity in deconjugating Nedd8 from Cul1 in vivo.

These results demonstrate that CSN is has metalloprotease activity. The active site of CSN resides, at least in part, in the Jab1/Csn5 subunit, and this active site is proposed to bind a metal ion which initiates hydrolytic attack of the isopeptide bonds cleaved by CSN. These findings enable the development of targeted screens for compounds that inhibit or enhance the catalytic activity of CSN, and also allow for the rationale design of compounds that modulate CSN activity based on knowledge of the mechanism of action of other metalloenzymes.

These results provide a basis for re-engineering the specificity of CSN, Jab1, or related proteins to generate isopeptidases having desired specificities. Such modified isopeptidase enzymes can be useful in a variety of applications involving the cleavage of protein cross-links or conjugates. In addition, the results provide a basis for designing compounds that can inhibit the prokaryotic homologs of Csn5/Jab1 and for developing screening assays useful for isolating compounds having such inhibitory activity, such inhibitors being useful, for example, as antibiotics.

The role of Cys box (Cys 145) in association with the ability of CSN to deconjugate Nedd8 from Cul1 was examined using an in vitro deconjugation assay as described above. The results demonstrated that a Jab1 mutant, in which the conserved cysteine of the Cys box (Cys 145) was mutated to alanine, had wild-type levels of Nedd8 conjugate cleavage activity.

EXAMPLE 3

AMSH, AMSH1, and AMSH2

As disclosed above, the existence of a metalloprotease active site motif, the JAMM domain (:Jab1-associated metalloenzyme motif"), has been identified. The Rpn11 subunit of the 26S proteosome and the Csn5 subunit of the COP9-signalsome (CSN) both contain a JAMM domain. Thus, direct evidence is provided that the JAMM domain of Csn5 is essential for the Nedd8 isopeptidase activity of CSN, and the JAMM domain of Rpn11 is essential for the ubiquitin isopeptidase activity of the 26S proteosome.

These results demonstrate that eukaryotic JAMM domain proteins contain isopeptidase activity that deconjugate modifier proteins from target proteins, wherein the carboxy terminus of the modifier protein is attached via a peptide bond to a free amino group of the target protein, including, but not restricted to the amino terminus and the epsilon amino group of lysine residues in the target protein.

In addition to Csn5 and Rpn11, several other proteins expressed in human cells contain an intact JAMM domain (see Table 1), including, for example, the AMSH proteins, which have been implicated in cytokine signaling, TGF-β signaling, and survival of hippocampal neurons (Ishii et al., *Mol. Cell Biol*. 24:8626-8637, 2001; Itoh et al., *EMBO J*. 15:4132-4142, 2001; Tanaka et al., *J. Biol. Chem*. 27:19129-35, 1999).

The present results indicate that the histidine 335, histidine 337, and aspartate 348 residues of AMSH (and the equivalent residues in AMSH1 and AMSH2, see FIG. 2) specify a metalloprotease active site. Furthermore, compounds that inhibit the active site specified by these residues likely can inhibit the ability of AMSH, AMSH1, and AMSH2 to deconjugate a modifier protein from a target protein, for example, a modifier protein such as NEDD8, UBL1, SMT3H2, SMT3H1, APG12, FAT10, Fau, UCRP/ISG15, URM1, or UBL5.

EXAMPLE 4

CSN Isopeptidase Activity is Required for SCF Ubiquitin Ligase Activity

To confirm that diminished deneddylation activity exacerbates the effect of diminished SCF activity, it needs to be established that specifically disrupting the deneddylation activity of CSN exacerbates the effect of a reduction in SCF activity, and to further demonstrate that such an effect occurs for multiple SCF subunits.

To determine whether diminished CSN-associated deneddylation activity can exacerbate the effect of diminished SCF ubiquitin ligase activity, genetic interaction studies were performed in budding yeast. Although it is not clear whether budding yeast cells contain the entire CSN complex as found in plant and animal cells, they at least contain an ortholog of the Csn5 subunit, which is the most highly conserved member of the complex and is the subunit that contains the active site residues that catalyze deneddylation of substrate. Mutant rri1Δ cells accumulate the budding yeast Cul1 orthologue Cdc53 exclusively in a Nedd8-modified form (Lyapina et al., supra, 2001), indicating that RRI1 function is essential for Cdc53 deneddylation. Likewise, the Csn5 subunit of CSN is required to maintain the proper neddylation state of Cul1 in fission yeast (Lyapina et al., 2001) and in *Arabidopsis thaliana* (Schwechheimer et al., 2001).

It was previously disclosed that Csn5 orthologues in *Drosophila melanogaster, Caenorhabditis elegans, S. pombe* and humans contain two conserved histidine residues and a conserved aspartate residue that together coordinate a metal ion and form the active site that catalyzes cleavage of the isopeptide bond that links Nedd8 to substrate proteins. As shown in Table 2, *S. cerevisiae* Rri1 contains the same conserved residues. Whereas wild-type RRI1 on a plasmid complemented the Cdc53 deneddylation defect of an rri1Δ mutant, RRI1 plasmids in which the conserved histidine or aspartate residues have been altered were unable to restore the normal neddylation status of Cdc53 (not shown). This result demonstrates that the JAMM domain residues are required for deneddylation activity of Rri1.

TABLE 2

Alignment of Csn5 Homologs

| Organism | Alignment | Acc. No. |
|---|---|---|
| Human | VGRLENAIGWYHSHPGYGCWLSGIDVSTQ | XP_034280 (5)* |
| Drosophila | VGRMEHAVGWYHSHPGYGCWLSGIDVSTQ | AAF55321 (6) |
| Arabidopsis | AGRLENVVGWYHSHPGYGCWLSGIDVSTQ | AAC36343 (7) |
| C. elegans | EGRKEKVVGWYHSHPGYGCWLSGIDVSTQ | AAB37991 (8) |
| S. cerevisiae | KGAKLNVVGWFHSHPGYDCWLSNIDIQTQ | NP_010065 (9) | bold print indicates conserved JAMM domain consensus sequence (see, also, SEQ ID NO:1)
*-SEQ ID NO:
S. cerevisiae Rri1.

Plasmids encoding GST-Rri1 fusion proteins, including wild type Rri1 and Rri1 mutants having a point mutation in histidine 179 (H179A), histidine 181 (H181A), or aspartate 192 (D192A), were transformed into SKP1myc9 rri1Δ yeast cells. Logarithmically growing cultures of transformed cells were lysed with glass beads, and the lysate was subjected to immunoprecipitation with anti-myc monoclonal antibody 9E10. Washed immunoprecipitates were fractionated by SDS-PAGE, transferred to nitrocellulose, and immunoblotted with anti-Cdc53 or anti-GST polyclonal antibodies. Essentially all of the Cdc53 in rri1Δ cells migrated as a Rub1-modified species (Rub1 is the S. cerevisiae ortholog of Nedd8). Re-introduction of wild type Rri1 expression promoted cleavage of Rub 1 from a fraction of the Cdc53 molecules. However, the H179A, H181A, and D192N mutants were unable to restore Rub1 cleavage activity. Screening with the anti-GST antibody confirmed that the wild type and mutant forms of GST-Rri1 were expressed.

The requirement of RRI1-associated Nedd8 isopeptidase activity to sustain SCF activity was examined in cells in which SCF function was compromised by mutation. The following nine strains were constructed: 1) rri1Δ; 2) cdc53-1; 3) cdc34-2; 4) cdc4-1; 5) skp1-12; 6) rri1Δ cdc53-1; 7) rri1Δ cdc34-2; 8) rri1Δ cdc4-1; and 9) rri1Δ skp1-12. The cdc53-1, cdc34-2, skp1-12, and cdc4-1 alleles are temperature-sensitive conditional lethal mutations. In S. cerevisiae, Cdc34 is the only Ubc (E2) reported to interact with SCF.

The strains were grown at an intermediate temperature (33° C.) that is normally permissive for the function of the temperature-sensitive gene products. Cells having the various genotypes were progressively diluted in 5-fold increments from left to right, and were spotted onto YPD plates and incubated at 25° C. (control; permissive temperature) or 33° C. for 1-2 days. All of the single mutant strains were able to grow at 33° C., whereas all of the double mutant strains exhibited a severe growth defect. Thus, the growth of all single mutants (cdc53-1, cdc34-2, cdc4-1, and skp1-12) was exacerbated by the rri1Δ mutation.

The above result indicates that Nedd8 isopeptidase activity is necessary in cells with compromised SCF pathway activity. However, the RRI1 gene (like the CSN complex in other organisms) also may have a second activity that promotes SCF pathway function. To address this possibility for the cdc34-2 and skp1-12 mutations, doubly-mutated strains (i.e., rri1Δ and SCF pathway deficient) were generated that contained a plasmid encoding GST fusion proteins comprising either the wild-type RRI1 gene or a mutant in which the conserved histidine 179, histidine 181, or aspartate 192 residue is substituted with an alanine residue. The GST-RRI1 fusion construct was expressed from the GAL1 promoter. Transformants were progressively diluted in 5-fold increments, spotted onto YPD (Glucose) or YPG (Galactose) plates, and incubated at 25° C., 33° C. or 34° C. for 1-2 days; the GST-RRI1 fusion is expressed only on galactose-containing medium. The wild-type, but not mutant, RRI1 plasmids restored growth at 33° C. to the rri1Δ cdc34-2 and rri1Δskp1-12 mutant strains. Together, these results demonstrate that inhibition of Nedd8 isopeptidase activity exacerbates the effect of treatments that diminish SCF activity.

To determine whether deneddylation is important for the role of the SCF pathway in promoting protein degradation, the degradation of the cell cycle regulatory protein Sic1 was examined in skp1-12 and skp1-12 rri1Δ cells. Sic1 is targeted for degradation in an SCF/Cdc34-dependent manner (Schwob et al., Cell 79:233-244, 1994). Immunoblot analysis of these strains at various time points after SIC1 transcription was extinguished revealed that the Sic1 polypeptide level declined more rapidly in skp1-12 cells than in skp1-12 rri1 cells. This result demonstrates that deneddylation by CSN is required to maintain optimal activity of the SCF pathway.

In summary, this Example demonstrates that inhibition of the isopeptidase activity of CSN, for example, by introducing mutations that alter the conserved JAMM domain residues of the isopeptidase, synthetically enhance the effect of mutations that diminish SCF activity. This result is in contrast with the result predicted from prior biochemical studies, i.e., that a CSN mutant would suppress an SCF mutant. As such, these results indicate that SCF activity can be reduced or inhibited using an agent that decreases CSN isopeptidase activity, and that such an agent can be used in combination, for example, with a second agent that more directly inhibits SCF activity, thus providing a means to enhance the efficacy of agents that inhibit SCF ubiquitin ligase.

Although the invention has been described with reference to the presently preferred embodiment, it should be understood that various modifications can be made without departing from the spirit of the invention. Accordingly, the invention is limited only by the following claims.

What is claimed is:

1. A method of identifying an agent for modulating COP9 Signalsome (CSN) isopeptidase activity comprising:
   contacting a CSN polypeptide having the amino acid sequence of SEQ ID NO:84 or 85 in the presence of a modifier protein and a target protein, wherein the CSN polypeptide has isopeptidase activity and deconjugates the modifier protein from the target protein under conditions suitable for CSN isopeptidase activity, and wherein the conditions include adenosine tri-phosphate (ATP); and
   determining the CSN isopeptidase activity by measuring cleavage of the modifier protein from the target protein in the presence or absence of the test agent, wherein a difference in the isopeptidase activity in the presence versus the absence of the agent is indicative of an agent that affects the isopeptidase activity of the CSN polypeptide, and wherein the target protein has ubiquitin ligase activity and wherein the modifier protein is a ubiquitin or a ubiquitin-like modifier protein.

2. The method of claim 1, wherein the CSN polypeptide has a JAMM domain comprising the amino acid sequence of H(S/T)HXXXXXXXSXXD (SEQ ID NO:65).

3. The method of claim 1, wherein the CSN polypeptide has a JAMM domain comprises the amino acid sequence of EXHyXHyHy(X)$_n$HXHXXXXXXXXXD (SEQ ID NO:13).

4. The method of claim 1, wherein the test agent decreases deconjugation of the modifier protein from the target protein, thereby identifying an agent that reduces or inhibits the isopeptidase activity of CSN.

5. The method of claim 1, wherein the isopeptidase activity cleaves a peptide bond between a carboxy terminus of the modifier protein and an epsilon amino group of a lysine residue of the target protein.

6. The method of claim 1, wherein the modifier protein is Nedd8, UBL1, SMT3H2, SMT3H1, APG12, FAT10, Fau, UCRP, URM1, or UBL5.

7. The method of claim 1, wherein the target protein comprises a cullin homology domain.

8. The method of claim 1, wherein the target protein is Cul1, Cul2, Cul3, Cul4A, Cul4B, or Cul5.

9. The method of claim 1, wherein the target protein comprises a SCF ubiquitin ligase.

10. The method of claim 1, wherein the target protein or the modifier protein or both comprises a detectable label, and wherein detecting the isopeptidase activity of CSN comprises detecting the detectable label.

11. The method of claim 10, wherein the detectable label comprises a peroxidase, alkaline phosphatase, or luciferase.

12. The method of claim 10, wherein the detectable label comprises a fluorescent protein.

13. The method of claim 10, wherein the fluorescent protein is a green fluorescent protein, yellow fluorescent protein, cyan fluorescent protein, dsRed, or a derivative thereof.

14. The method of claim 10, wherein the each of the target protein and the modifier protein comprises a detectable label of a fluorescence resonance energy transfer (FRET) pair, and wherein detecting the isopeptidase activity of CSN comprises detecting a change in FRET.

15. The method of claim 1, wherein the test agent is a peptide, a peptide derivative, a peptoid, a peptidomimetic, a polynucleotide, a polynucleotide derivative, or a small organic molecule.

16. The method of claim 15, wherein the peptide derivative comprises a peptide hydroxamate or a phosphinic peptide.

17. The method of claim 15, wherein the test agent comprises a library of test agents.

18. The method of claim 17, wherein the library is a combinatorial library.

19. The method of claim 17, wherein the combinatorial library comprises a library of random test agents, biased test agents, or variegated test agents.

20. The method of claim 18, wherein the combinatorial library of test agents comprises a hydroxamate compound library, reverse hydroxamate compound library, carboxylate compound library, thiol compound library, a phosphinic peptide library, or phosphonate compound library.

21. The method of claim 1, which is performed in vitro.

22. The method of claim 1, which is performed in a high throughput format.

* * * * *

SEQUENCE LISTING

<160> NUMBER OF SEQ ID NOS: 83

<210> SEQ ID NO 1
<211> LENGTH: 14

```
<212> TYPE: PRT
<213> ORGANISM: Artificial sequence
<220> FEATURE:
<223> OTHER INFORMATION: JAMM domain
<220> FEATURE:
<221> NAME/KEY: MISC_FEATURE
<222> LOCATION: (1)..(14)
<223> OTHER INFORMATION: Xaa is any amino acid

<400> SEQUENCE: 1

His Xaa His Xaa Xaa Xaa Xaa Xaa Xaa Xaa Xaa Xaa Xaa Asp
 1               5                  10

<210> SEQ ID NO 2
<211> LENGTH: 17
<212> TYPE: PRT
<213> ORGANISM: Artificial sequence
<220> FEATURE:
<223> OTHER INFORMATION: JAMM domain
<220> FEATURE:
<221> NAME/KEY: MISC_FEATURE
<222> LOCATION: (3)..(3)
<223> OTHER INFORMATION: Xaa is Tyr or Ile
<220> FEATURE:
<221> NAME/KEY: MISC_FEATURE
<222> LOCATION: (5)..(5)
<223> OTHER INFORMATION: Xaa is Ser or Thr
<220> FEATURE:
<221> NAME/KEY: MISC_FEATURE
<222> LOCATION: (8)..(16)
<223> OTHER INFORMATION: Xaa is any amino acid

<400> SEQUENCE: 2

Gly Trp Xaa His Xaa His Pro Xaa Xaa Xaa Xaa Xaa Xaa Ser Xaa Xaa
 1               5                  10                  15

Asp

<210> SEQ ID NO 3
<211> LENGTH: 246
<212> TYPE: PRT
<213> ORGANISM: Homo sapiens

<400> SEQUENCE: 3

Thr Met Ile Ile Met Asp Ser Phe Ala Leu Pro Val Glu Gly Thr Glu
 1               5                  10                  15

Thr Arg Val Asn Ala Gln Ala Ala Ala Tyr Glu Tyr Met Ala Ala Tyr
                20                  25                  30

Ile Glu Asn Ala Lys Gln Val Gly Arg Leu Glu Asn Ala Ile Gly Trp
             35                  40                  45

Tyr His Ser His Pro Gly Tyr Gly Cys Trp Leu Ser Gly Ile Asp Val
         50                  55                  60

Ser Thr Gln Met Leu Asn Gln Gln Phe Gln Glu Pro Phe Val Ala Val
 65                  70                  75                  80

Val Ile Asp Pro Thr Arg Thr Ile Ser Ala Gly Lys Val Asn Leu Gly
                 85                  90                  95

Ala Phe Arg Thr Tyr Pro Lys Gly Tyr Lys Pro Pro Asp Glu Gly Pro
            100                 105                 110

Ser Glu Tyr Gln Thr Ile Pro Leu Asn Lys Ile Glu Asp Phe Gly Val
        115                 120                 125

His Cys Lys Gln Tyr Tyr Ala Leu Glu Val Ser Tyr Phe Lys Ser Ser
    130                 135                 140

Leu Asp Arg Lys Leu Leu Glu Leu Leu Trp Asn Lys Tyr Trp Val Asn
145                 150                 155                 160
```

```
Thr Leu Ser Ser Ser Leu Leu Thr Asn Ala Asp Tyr Thr Thr Gly
            165                 170                 175

Gln Val Phe Asp Leu Ser Glu Lys Leu Glu Gln Ser Glu Ala Gln Leu
            180                 185                 190

Gly Arg Gly Ser Phe Met Leu Gly Leu Glu Thr His Asp Arg Lys Ser
            195                 200                 205

Glu Asp Lys Leu Ala Lys Ala Thr Arg Asp Ser Cys Lys Thr Thr Ile
210                 215                 220

Glu Ala Ile His Gly Leu Met Ser Gln Val Ile Lys Asp Lys Leu Phe
225                 230                 235                 240

Asn Gln Ile Asn Ile Ser
            245

<210> SEQ ID NO 4
<211> LENGTH: 245
<212> TYPE: PRT
<213> ORGANISM: Homo sapiens

<400> SEQUENCE: 4

Thr Val Arg Val Ile Asp Val Phe Ala Met Pro Gln Ser Gly Thr Gly
1               5                   10                  15

Val Ser Val Glu Ala Val Asp Pro Val Phe Gln Ala Lys Met Leu Asp
            20                  25                  30

Met Leu Lys Gln Thr Gly Arg Pro Glu Met Val Val Gly Trp Tyr His
            35                  40                  45

Ser His Pro Gly Phe Gly Cys Trp Leu Ser Gly Val Asp Ile Asn Thr
        50                  55                  60

Gln Gln Ser Phe Glu Ala Leu Ser Glu Arg Ala Val Ala Val Val Val
65                  70                  75                  80

Asp Pro Ile Gln Ser Val Lys Gly Lys Val Val Ile Asp Ala Phe Arg
                85                  90                  95

Leu Ile Asn Ala Asn Met Met Val Leu Gly His Glu Pro Arg Gln Thr
                100                 105                 110

Thr Ser Asn Leu Gly His Leu Asn Lys Pro Ser Ile Gln Ala Leu Ile
            115                 120                 125

His Gly Leu Asn Arg His Tyr Tyr Ser Ile Thr Ile Asn Tyr Arg Lys
        130                 135                 140

Asn Glu Leu Glu Gln Lys Met Leu Leu Asn Leu His Lys Lys Ser Trp
145                 150                 155                 160

Met Glu Gly Leu Thr Leu Gln Asp Tyr Ser Glu His Cys Lys His Asn
                165                 170                 175

Glu Ser Val Val Lys Glu Met Leu Glu Leu Ala Lys Asn Tyr Asn Lys
            180                 185                 190

Ala Val Glu Glu Glu Asp Lys Met Thr Pro Glu Gln Leu Ala Ile Lys
        195                 200                 205

Asn Val Gly Lys Gln Asp Pro Lys Arg His Leu Glu Glu His Val Asp
    210                 215                 220

Val Leu Met Thr Ser Asn Ile Val Gln Cys Leu Ala Ala Met Leu Asp
225                 230                 235                 240

Thr Val Val Phe Lys
            245

<210> SEQ ID NO 5
<211> LENGTH: 29
<212> TYPE: PRT
<213> ORGANISM: Homo sapiens
```

```
<400> SEQUENCE: 5

Val Gly Arg Leu Glu Asn Ala Ile Gly Trp Tyr His Ser His Pro Gly
1               5                   10                  15

Tyr Gly Cys Trp Leu Ser Gly Ile Asp Val Ser Thr Gln
            20                  25

<210> SEQ ID NO 6
<211> LENGTH: 29
<212> TYPE: PRT
<213> ORGANISM: Drosophila

<400> SEQUENCE: 6

Val Gly Arg Met Glu His Ala Val Gly Trp Tyr His Ser His Pro Gly
1               5                   10                  15

Tyr Gly Cys Trp Leu Ser Gly Ile Asp Val Ser Thr Gln
            20                  25

<210> SEQ ID NO 7
<211> LENGTH: 29
<212> TYPE: PRT
<213> ORGANISM: Arabidopsis

<400> SEQUENCE: 7

Ala Gly Arg Leu Glu Asn Val Val Gly Trp Tyr His Ser His Pro Gly
1               5                   10                  15

Tyr Gly Cys Trp Leu Ser Gly Ile Asp Val Ser Thr Gln
            20                  25

<210> SEQ ID NO 8
<211> LENGTH: 29
<212> TYPE: PRT
<213> ORGANISM: C. elegans

<400> SEQUENCE: 8

Glu Gly Arg Lys Glu Lys Val Val Gly Trp Tyr His Ser His Pro Gly
1               5                   10                  15

Tyr Gly Cys Trp Leu Ser Gly Ile Asp Val Ser Thr Gln
            20                  25

<210> SEQ ID NO 9
<211> LENGTH: 29
<212> TYPE: PRT
<213> ORGANISM: S. cerevisiae

<400> SEQUENCE: 9

Lys Gly Ala Lys Leu Asn Val Val Gly Trp Phe His Ser His Pro Gly
1               5                   10                  15

Tyr Asp Cys Trp Leu Ser Asn Ile Asp Ile Gln Thr Gln
            20                  25

<210> SEQ ID NO 10
<211> LENGTH: 29
<212> TYPE: PRT
<213> ORGANISM: Artificial sequence
<220> FEATURE:
<223> OTHER INFORMATION: Mutant of JAMM domain

<400> SEQUENCE: 10

Lys Gly Ala Lys Leu Asn Val Val Gly Trp Phe Ala Ser His Pro Gly
1               5                   10                  15

Tyr Asp Cys Trp Leu Ser Asn Ile Asp Ile Gln Thr Gln
```

<210> SEQ ID NO 11
<211> LENGTH: 29
<212> TYPE: PRT
<213> ORGANISM: Artificial sequence
<220> FEATURE:
<223> OTHER INFORMATION: Mutant of JAMM domain

<400> SEQUENCE: 11

Lys Gly Ala Lys Leu Asn Val Val Gly Trp Phe His Ser Ala Pro Gly
1               5                   10                  15

Tyr Asp Cys Trp Leu Ser Asn Ile Asp Ile Gln Thr Gln
            20                  25

<210> SEQ ID NO 12
<211> LENGTH: 29
<212> TYPE: PRT
<213> ORGANISM: Artificial sequence
<220> FEATURE:
<223> OTHER INFORMATION: Mutant of JAMM domain

<400> SEQUENCE: 12

Lys Gly Ala Lys Leu Asn Val Val Gly Trp Phe His Ser His Pro Gly
1               5                   10                  15

Tyr Ala Cys Trp Leu Ser Asn Ile Asn Ile Gln Thr Gln
            20                  25

<210> SEQ ID NO 13
<211> LENGTH: 21
<212> TYPE: PRT
<213> ORGANISM: Artificial sequence
<220> FEATURE:
<223> OTHER INFORMATION: JAMM domain
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is any amino acid
<220> FEATURE:
<221> NAME/KEY: MISC_FEATURE
<222> LOCATION: (11)..(20)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is a hydrophobic amino acid
<220> FEATURE:
<221> NAME/KEY: MISC_FEATURE
<222> LOCATION: (5)..(6)
<223> OTHER INFORMATION: Xaa is a hydrophobic amino acid
<220> FEATURE:
<221> NAME/KEY: MISC_FEATURE
<222> LOCATION: (7)..(7)
<223> OTHER INFORMATION: Xaa indicates about 40 to 83 amino acid
      residues

<400> SEQUENCE: 13

Glu Xaa Xaa Xaa Xaa Xaa Xaa His Xaa His Xaa Xaa Xaa Xaa Xaa Xaa
1               5                   10                  15

Xaa Xaa Xaa Xaa Asp
            20

```
<210> SEQ ID NO 14
<211> LENGTH: 21
<212> TYPE: PRT
<213> ORGANISM: Artificial sequence
<220> FEATURE:
<223> OTHER INFORMATION: JAMM domain
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (11)..(17)
<223> OTHER INFORMATION: Xaa is any amino acid
<220> FEATURE:
<221> NAME/KEY: MISC_FEATURE
<222> LOCATION: (19)..(20)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is a hydrophobic amino acid
<220> FEATURE:
<221> NAME/KEY: MISC_FEATURE
<222> LOCATION: (5)..(6)
<223> OTHER INFORMATION: Xaa is a hydrophobic amino acid
<220> FEATURE:
<221> NAME/KEY: MISC_FEATURE
<222> LOCATION: (7)..(7)
<223> OTHER INFORMATION: Xaa indicates about 40 to 83 amino acid
    residues
<220> FEATURE:
<221> NAME/KEY: MISC_FEATURE
<222> LOCATION: (9)..(9)
<223> OTHER INFORMATION: Xaa is serine or threonine

<400> SEQUENCE: 14

Glu Xaa Xaa Xaa Xaa Xaa Xaa His Xaa His Xaa Xaa Xaa Xaa Xaa Xaa
1               5                   10                  15

Xaa Ser Xaa Xaa Asp
            20

<210> SEQ ID NO 15
<211> LENGTH: 89
<212> TYPE: PRT
<213> ORGANISM: Homo sapiens
<220> FEATURE:
<221> NAME/KEY: MISC_FEATURE
<222> LOCATION: (42)..(42)
<223> OTHER INFORMATION: Xaa indicates 29 amino acid residues

<400> SEQUENCE: 15

Ser Ala Leu Ala Leu Leu Lys Met Val Met His Ala Arg Ser Gly Gly
1               5                   10                  15

Asn Leu Glu Val Met Gly Leu Met Leu Gly Lys Val Asp Gly Glu Thr
            20                  25                  30

Met Ile Ile Met Asp Ser Phe Ala Leu Xaa Gly His Leu Glu Asn Ala
        35                  40                  45

Ile Gly Trp Tyr His Ser His Pro Gly Tyr Gly Cys Trp Leu Ser Gly
    50                  55                  60

Ile Asp Val Ser Thr Gln Met Leu Asn Gln Gln Phe Gln Glu Pro Phe
65                  70                  75                  80

Val Ala Val Val Ile Asp Pro Thr Arg
            85
```

```
<210> SEQ ID NO 16
<211> LENGTH: 89
<212> TYPE: PRT
<213> ORGANISM: Drosophila melanogaster
<220> FEATURE:
<221> NAME/KEY: MISC_FEATURE
<222> LOCATION: (42)..(42)
<223> OTHER INFORMATION: Xaa indicates 29 amino acid residues

<400> SEQUENCE: 16
```

Ser Ala Leu Ala Leu Leu Lys Met Val Met His Ala Arg Ser Gly Gly
1               5                   10                  15

Thr Leu Glu Val Met Gly Leu Met Gly Lys Val Glu Asp Asn Thr
            20                  25                  30

Met Ile Val Met Asp Ala Phe Ala Leu Xaa Gly Arg Met Glu His Ala
        35                  40                  45

Val Gly Trp Tyr His Ser His Pro Gly Tyr Gly Cys Trp Leu Ser Gly
    50                  55                  60

Ile Asp Val Ser Thr Gln Met Leu Asn Gln Thr Tyr Gln Glu Pro Phe
65                  70                  75                  80

Val Ala Ile Val Val Asp Pro Val Arg
                85

```
<210> SEQ ID NO 17
<211> LENGTH: 89
<212> TYPE: PRT
<213> ORGANISM: Caenorhabditis elegans
<220> FEATURE:
<221> NAME/KEY: MISC_FEATURE
<222> LOCATION: (42)..(42)
<223> OTHER INFORMATION: Xaa indicates 29 amino acid residues

<400> SEQUENCE: 17
```

Ser Ala Ile Ala Leu Leu Lys Met Thr Met His Ala Lys Arg Gly Gly
1               5                   10                  15

Asn Leu Glu Ile Met Gly Leu Leu Gln Gly Arg Ile Asp Ala Asn Ser
            20                  25                  30

Phe Ile Ile Leu Asp Val Phe Ala Leu Xaa Gly Arg Lys Glu Lys Val
        35                  40                  45

Val Gly Trp Tyr His Ser His Pro Gly Tyr Gly Cys Trp Leu Ser Gly
    50                  55                  60

Ile Asp Val Ser Thr Gln Thr Leu Asn Gln Lys Phe Gln Glu Pro Trp
65                  70                  75                  80

Val Ala Ile Val Ile Asp Pro Leu Arg
                85

```
<210> SEQ ID NO 18
<211> LENGTH: 89
<212> TYPE: PRT
<213> ORGANISM: Arabidopsis thaliana
<220> FEATURE:
<221> NAME/KEY: MISC_FEATURE
<222> LOCATION: (42)..(42)
<223> OTHER INFORMATION: Xaa indicates 29 amino acid residues

<400> SEQUENCE: 18
```

Ser Ala Leu Ala Leu Leu Lys Met Val Val His Ala Arg Ser Gly Gly
1               5                   10                  15

Thr Ile Glu Ile Met Gly Leu Met Gln Gly Lys Thr Glu Gly Asp Thr
            20                  25                  30

Ile Ile Val Met Asp Ala Phe Ala Leu Xaa Gly Arg Leu Glu Asn Val

```
                        35                  40                  45
Val Gly Trp Tyr His Ser His Pro Gly Tyr Gly Cys Trp Leu Ser Gly
    50                  55                  60

Ile Asp Val Ser Thr Gln Met Leu Asn Gln Gln Tyr Gln Glu Pro Phe
65                  70                  75                  80

Leu Ala Val Val Ile Asp Pro Thr Arg
                85

<210> SEQ ID NO 19
<211> LENGTH: 89
<212> TYPE: PRT
<213> ORGANISM: Saccharomyces cerevisiae
<220> FEATURE:
<221> NAME/KEY: MISC_FEATURE
<222> LOCATION: (42)..(42)
<223> OTHER INFORMATION: Xaa indicates 29 amino acid residues

<400> SEQUENCE: 19

Ser Lys Leu Ser Cys Glu Lys Ile Thr His Tyr Ala Val Arg Gly Gly
1               5                   10                  15

Asn Ile Glu Ile Met Gly Ile Leu Met Gly Phe Thr Leu Lys Asp Asn
            20                  25                  30

Ile Val Val Met Asp Cys Phe Asn Leu Xaa Gly Ala Lys Leu Asn Val
        35                  40                  45

Val Gly Trp Phe His Ser His Pro Gly Tyr Asp Cys Trp Leu Ser Asn
    50                  55                  60

Ile Asp Ile Gln Thr Gln Asp Leu Asn Gln Arg Phe Gln Asp Pro Tyr
65                  70                  75                  80

Val Ala Ile Val Val Asp Pro Leu Lys
                85

<210> SEQ ID NO 20
<211> LENGTH: 89
<212> TYPE: PRT
<213> ORGANISM: Homo sapiens
<220> FEATURE:
<221> NAME/KEY: MISC_FEATURE
<222> LOCATION: (44)..(44)
<223> OTHER INFORMATION: Xaa indicates 22 amino acid residues
<220> FEATURE:
<221> NAME/KEY: MISC_FEATURE
<222> LOCATION: (75)..(75)
<223> OTHER INFORMATION: Xaa indicates 9 amino acid residues

<400> SEQUENCE: 20

Val Ser Ser Asn Val Leu Phe Leu Leu Asp Phe His Ser His Leu Thr
1               5                   10                  15

Arg Ser Glu Val Val Gly Tyr Leu Gly Gly Arg Trp Asp Val Asn Ser
            20                  25                  30

Gln Met Leu Thr Val Leu Arg Ala Phe Pro Cys Xaa Leu Arg Gly Leu
        35                  40                  45

Ser Leu Val Gly Trp Tyr His Ser His Pro His Ser Pro Ala Leu Pro
    50                  55                  60

Ser Leu Gln Asp Ile Asp Ala Gln Met Asp Xaa Asn Gly Phe Gln Pro
65                  70                  75                  80

Cys Leu Ala Leu Leu Cys Ser Pro Tyr
                85

<210> SEQ ID NO 21
<211> LENGTH: 89
<212> TYPE: PRT
```

<213> ORGANISM: Drosophila melanogaster
<220> FEATURE:
<221> NAME/KEY: MISC_FEATURE
<222> LOCATION: (44)..(44)
<223> OTHER INFORMATION: Xaa indicates 22 amino acid residues
<220> FEATURE:
<221> NAME/KEY: MISC_FEATURE
<222> LOCATION: (75)..(75)
<223> OTHER INFORMATION: Xaa indicates 10 amino acid residues

<400> SEQUENCE: 21

Val Asn Ser Ser Ala Leu Leu Leu Ala Asp Phe His Cys His Leu Thr
1               5                   10                  15

Val Arg Glu Val Cys Gly Tyr Leu Gly Gly Thr Trp Asp Met Asn Thr
            20                  25                  30

His Thr Leu Ser Ile Thr Lys Thr Tyr Pro Cys Xaa Gln Asp Gln Leu
        35                  40                  45

Leu Leu Val Gly Trp Tyr His Ser His Pro Lys Phe Gln Ala Glu Pro
    50                  55                  60

Thr Leu Arg Asp Cys Asp Ala Gln Leu Asp Xaa Leu Thr Tyr Thr Pro
65                  70                  75                  80

Cys Val Ser Leu Ile Ile Ser Pro Tyr
                85

<210> SEQ ID NO 22
<211> LENGTH: 89
<212> TYPE: PRT
<213> ORGANISM: Homo sapiens
<220> FEATURE:
<221> NAME/KEY: MISC_FEATURE
<222> LOCATION: (44)..(44)
<223> OTHER INFORMATION: Xaa indicates 22 amino acid residues
<220> FEATURE:
<221> NAME/KEY: MISC_FEATURE
<222> LOCATION: (75)..(75)
<223> OTHER INFORMATION: Xaa indicates 6 amino acid residues

<400> SEQUENCE: 22

Val Ala Ser Glu Ala Leu Leu Ile Met Asp Leu His Ala His Val Ser
1               5                   10                  15

Met Ala Glu Val Ile Gly Leu Leu Gly Gly Arg Tyr Ser Glu Val Asp
            20                  25                  30

Lys Val Val Glu Val Cys Ala Ala Glu Pro Cys Xaa Val Arg Gly Phe
        35                  40                  45

Ser Val Ile Gly Trp Tyr His Ser His Pro Ala Phe Asp Pro Asn Pro
    50                  55                  60

Ser Leu Arg Asp Ile Asp Thr Gln Ala Lys Xaa Arg Gly Ala Lys
65                  70                  75                  80

Phe Ile Gly Met Ile Val Ser Pro Tyr
                85

<210> SEQ ID NO 23
<211> LENGTH: 91
<212> TYPE: PRT
<213> ORGANISM: Homo sapiens
<220> FEATURE:
<221> NAME/KEY: MISC_FEATURE
<222> LOCATION: (33)..(33)
<223> OTHER INFORMATION: Xaa indicates 23 amino acid residues
<220> FEATURE:
<221> NAME/KEY: MISC_FEATURE
<222> LOCATION: (44)..(44)
<223> OTHER INFORMATION: Xaa indicates 32 amino acid residues

<400> SEQUENCE: 23

```
Glu Ser Asp Ala Phe Leu Val Cys Leu Asn His Ala Leu Ser Thr Glu
1               5                   10                  15

Lys Glu Glu Val Met Gly Leu Cys Ile Gly Glu Leu Asn Asp Asp Thr
                20                  25                  30

Xaa Arg Ile Val His Ile His Ser Val Ile Ile Xaa Gly Arg Pro Met
            35                  40                  45

Arg Val Val Gly Trp Tyr His Ser His Pro His Ile Thr Val Trp Pro
        50                  55                  60

Ser His Val Asp Val Arg Thr Gln Ala Met Tyr Gln Met Met Asp Gln
65                  70                  75                  80

Gly Phe Val Gly Leu Ile Phe Ser Cys Phe Ile
                85                  90
```

<210> SEQ ID NO 24
<211> LENGTH: 90
<212> TYPE: PRT
<213> ORGANISM: Arabidopsis thaliana
<220> FEATURE:
<221> NAME/KEY: MISC_FEATURE
<222> LOCATION: (43)..(43)
<223> OTHER INFORMATION: Xaa indicates 39 amino acid residues

<400> SEQUENCE: 24

```
Ser Glu Asp Val Trp Leu Thr Cys Leu Thr His Ala Leu Ser Thr Glu
1               5                   10                  15

Thr Glu Glu Ile Met Gly Leu Leu Leu Gly Asp Ile Glu Tyr Ser Lys
                20                  25                  30

Asn Gly Glu Ser Ala Thr Ala Met Ile Trp Xaa Gly Arg Thr Thr Arg
            35                  40                  45

Val Ile Gly Trp Tyr His Ser His Pro His Ile Thr Val Leu Pro Ser
        50                  55                  60

His Val Asp Val Arg Thr Gln Ala Met Tyr Gln Leu Leu Asp Ser Gly
65                  70                  75                  80

Phe Ile Gly Leu Ile Phe Ser Cys Phe Ser
                85                  90
```

<210> SEQ ID NO 25
<211> LENGTH: 88
<212> TYPE: PRT
<213> ORGANISM: Homo sapiens
<220> FEATURE:
<221> NAME/KEY: MISC_FEATURE
<222> LOCATION: (41)..(41)
<223> OTHER INFORMATION: Xaa indicates 24 amino acid residues

<400> SEQUENCE: 25

```
Asp Leu Cys His Lys Phe Leu Gln Leu Ala Glu Ser Asn Thr Val Arg
1               5                   10                  15

Gly Ile Glu Thr Cys Gly Ile Leu Cys Gly Lys Leu Thr His Asn Glu
                20                  25                  30

Phe Thr Ile Thr His Val Ile Xaa Gln His Asp Leu Leu Thr Leu
            35                  40                  45

Gly Trp Ile His Thr His Pro Thr Gln Thr Ala Phe Leu Ser Ser Val
        50                  55                  60

Asp Leu His Thr His Cys Ser Tyr Gln Leu Met Leu Pro Glu Ala Ile
65                  70                  75                  80

Ala Ile Val Cys Ser Pro Lys His
                85
```

```
<210> SEQ ID NO 26
<211> LENGTH: 88
<212> TYPE: PRT
<213> ORGANISM: Homo sapiens
<220> FEATURE:
<221> NAME/KEY: MISC_FEATURE
<222> LOCATION: (41)..(41)
<223> OTHER INFORMATION: Xaa indicates 24 amino acid residues

<400> SEQUENCE: 26

Arg Leu Cys Pro Gln Phe Leu Gln Leu Ala Ser Ala Asn Thr Ala Arg
1               5                   10                  15

Gly Val Glu Thr Cys Gly Ile Leu Cys Gly Lys Leu Met Arg Asn Glu
            20                  25                  30

Phe Thr Ile Thr His Val Leu Ile Xaa Gln Gln Gly Leu Ile Thr Leu
        35                  40                  45

Gly Trp Ile His Thr His Pro Thr Gln Thr Ala Phe Leu Ser Ser Val
    50                  55                  60

Asp Leu His Thr His Cys Ser Tyr Gln Met Met Leu Pro Glu Ser Val
65                  70                  75                  80

Ala Ile Val Cys Ser Pro Lys Phe
                85

<210> SEQ ID NO 27
<211> LENGTH: 88
<212> TYPE: PRT
<213> ORGANISM: Drosophila melanogaster
<220> FEATURE:
<221> NAME/KEY: MISC_FEATURE
<222> LOCATION: (41)..(41)
<223> OTHER INFORMATION: Xaa indicates 24 amino acid residues

<400> SEQUENCE: 27

Asp Thr Met Glu Val Phe Leu Lys Leu Ala Leu Ala Asn Thr Ser Lys
1               5                   10                  15

Asn Ile Glu Thr Cys Gly Val Leu Ala Gly His Leu Ser Gln Asn Gln
            20                  25                  30

Leu Tyr Ile Thr His Ile Ile Thr Xaa Gln Met Gln Leu Ile Thr Leu
        35                  40                  45

Gly Trp Ile His Thr His Pro Thr Gln Thr Ala Phe Leu Ser Ser Val
    50                  55                  60

Asp Leu His Thr His Cys Ser Tyr Gln Ile Met Pro Glu Ala Leu
65                  70                  75                  80

Ala Ile Val Cys Ala Pro Lys Tyr
                85

<210> SEQ ID NO 28
<211> LENGTH: 85
<212> TYPE: PRT
<213> ORGANISM: Archaeoglobus fulgidus
<220> FEATURE:
<221> NAME/KEY: MISC_FEATURE
<222> LOCATION: (42)..(42)
<223> OTHER INFORMATION: Xaa indicates 16 amino acid residues

<400> SEQUENCE: 28

Ser Arg Gly Leu Leu Lys Thr Ile Leu Glu Ala Ala Lys Ser Ala His
1               5                   10                  15

Pro Asp Glu Phe Ile Ala Leu Leu Ser Gly Ser Lys Asp Val Met Asp
            20                  25                  30

Glu Leu Ile Phe Leu Pro Phe Val Ser Xaa Pro Ile Gly Met Lys Val
```

-continued

```
                35                  40                  45
Phe Gly Thr Val His Ser His Pro Ser Pro Ser Cys Arg Pro Ser Glu
    50                  55                  60

Glu Asp Leu Ser Leu Phe Thr Arg Phe Gly Lys Tyr His Ile Ile Val
65                  70                  75                  80

Cys Tyr Pro Tyr Asp
                85

<210> SEQ ID NO 29
<211> LENGTH: 85
<212> TYPE: PRT
<213> ORGANISM: Methanopyrus kandleri
<220> FEATURE:
<221> NAME/KEY: MISC_FEATURE
<222> LOCATION: (42)..(42)
<223> OTHER INFORMATION: Xaa indicates 15 amino acid residues

<400> SEQUENCE: 29

Asp Ala Arg Leu Leu Asp Ser Leu Leu Glu Ala Ser Asp Lys Asn His
1               5                   10                  15

Pro Asp Glu Phe Phe Ala Met Leu Gly Gly Ser Ile Asp Ala Glu Thr
                20                  25                  30

Ile Thr Ile Asp Ser Leu Ile Val Val Xaa Val His Thr Cys Asp Val
            35                  40                  45

Ile Gly Thr Phe His Ser His Pro Tyr Gly Asp Pro Val Pro Ser Glu
    50                  55                  60

Asp Asp Leu Met Leu Phe Lys Arg Leu Gly Ala Val His Ala Ile Ala
65                  70                  75                  80

Ala Tyr Pro Tyr Thr
                85

<210> SEQ ID NO 30
<211> LENGTH: 88
<212> TYPE: PRT
<213> ORGANISM: Methanosarcina acetivorans
<220> FEATURE:
<221> NAME/KEY: MISC_FEATURE
<222> LOCATION: (45)..(45)
<223> OTHER INFORMATION: Xaa indicates 15 amino acid residues

<400> SEQUENCE: 30

Leu Leu Tyr Met Gln Ile Lys Gly Ile Ala Arg Asp Thr Leu Asp Phe
1               5                   10                  15

Ile Leu Glu Ala Ser Lys Ser Met Ala Pro Glu Glu Phe Ala Gly Leu
                20                  25                  30

Leu Gln Asp Gly Ile Ile Thr Glu Val Leu Ile Leu Xaa Met Pro Asn
            35                  40                  45

Val Lys Ala Val Gly Ser Val His Ser His Pro Gly Ala Asn Arg Arg
    50                  55                  60

Pro Ser Lys Ala Asp Leu Arg Leu Phe Ser Lys Thr Gly Asn Cys His
65                  70                  75                  80

Ile Ile Ala Gly Arg Pro Tyr Gly
                85

<210> SEQ ID NO 31
<211> LENGTH: 88
<212> TYPE: PRT
<213> ORGANISM: Methanothermobacter thermautotrophicus
<220> FEATURE:
<221> NAME/KEY: MISC_FEATURE
<222> LOCATION: (45)..(45)
```

<223> OTHER INFORMATION: Xaa indicates 16 amino acid residues

<400> SEQUENCE: 31

```
Phe Lys Pro Val Arg Val Val Asp Ser Glu Val Met Asp Glu
1               5                   10                  15

Val Leu Glu Ile Ala Arg Arg Ser His Pro His Glu Phe Ala Ala Leu
            20                  25                  30

Leu Glu Val Leu His Val Thr Gly Leu Ile Phe Leu Xaa Pro Pro Phe
        35                  40                  45

Thr Gly Ala Val Gly Ser Val His Ser His Pro Gly Pro Val Asn Leu
    50                  55                  60

Pro Ser Ala Ala Asp Leu His Phe Phe Ser Lys Asn Gly Leu Phe His
65                  70                  75                  80

Leu Ile Ile Ala His Pro Tyr Thr
                85
```

<210> SEQ ID NO 32
<211> LENGTH: 83
<212> TYPE: PRT
<213> ORGANISM: Pyrococcus horikoshii
<220> FEATURE:
<221> NAME/KEY: MISC_FEATURE
<222> LOCATION: (40)..(40)
<223> OTHER INFORMATION: Xaa indicates 25 amino acid residues

<400> SEQUENCE: 32

```
Leu Pro Lys Asn Ile Ile Glu Glu Ile Ile Thr Arg Ser Arg Glu Ser
1               5                   10                  15

Lys Ile Glu Ile Cys Gly Phe Ile Phe Gly Thr Lys Asn Gly Glu Arg
            20                  25                  30

Phe Ile Gly Lys Glu Val Phe Xaa Arg Lys Gly Leu Glu Val Val Thr
        35                  40                  45

Ile Phe His Ser His Leu Asn Cys Pro Pro Tyr Pro Ser Lys Lys Asp
    50                  55                  60

Ile Lys Gly Met Glu Asn Trp Arg Ile Pro Trp Leu Ile Val Ser Leu
65                  70                  75                  80

Lys Gly Asp
```

<210> SEQ ID NO 33
<211> LENGTH: 86
<212> TYPE: PRT
<213> ORGANISM: Pyrococcus horikoshii
<220> FEATURE:
<221> NAME/KEY: MISC_FEATURE
<222> LOCATION: (43)..(43)
<223> OTHER INFORMATION: Xaa indicates 12 amino acid residues

<400> SEQUENCE: 33

```
Arg Arg Glu Leu Leu Glu Tyr Leu Leu Glu Leu Ala Lys Ser Phe Tyr
1               5                   10                  15

Pro Arg Glu Val Ala Gly Phe Leu Arg Met Lys Asp Gly Val Phe Glu
            20                  25                  30

Glu Val Leu Ile Val Pro Lys Gly Phe Phe Xaa Pro His Asp Glu Ser
        35                  40                  45

Ile Lys Gly Thr Phe His Ser His Pro Ser Pro Phe Pro Tyr Pro Ser
    50                  55                  60

Glu Gly Asp Leu Met Phe Phe Ser Lys Phe Gly Gly Ile His Ile Ile
65                  70                  75                  80

Ala Ala Phe Pro Tyr Asp
```

85

<210> SEQ ID NO 34
<211> LENGTH: 83
<212> TYPE: PRT
<213> ORGANISM: Halobacterium sp.
<220> FEATURE:
<221> NAME/KEY: MISC_FEATURE
<222> LOCATION: (42)..(42)
<223> OTHER INFORMATION: Xaa indicates 26 amino acid residues

<400> SEQUENCE: 34

Thr Arg Glu Gly Tyr Asp Ser Val Leu Asp His Ala Gln Ala Asp Thr
1               5                   10                  15

Pro Arg Glu Ala Cys Gly Val Phe Val Gly Glu Arg Asp Gly Asp Leu
            20                  25                  30

Arg Arg Val Thr Ala Val Arg Val Xaa Ala Val Gly Arg Glu Val
        35                  40                  45

Val Gly Phe Tyr His Ser His Pro Val Gly Pro Gly Arg Pro Ser Ala
    50                  55                  60

Thr Asp Arg Glu His Ala Gln Trp Pro Asp Arg Val Tyr Val Val Ala
65                  70                  75                  80

Ser Leu Ala

<210> SEQ ID NO 35
<211> LENGTH: 86
<212> TYPE: PRT
<213> ORGANISM: Halobacterium sp.
<220> FEATURE:
<221> NAME/KEY: MISC_FEATURE
<222> LOCATION: (44)..(44)
<223> OTHER INFORMATION: Xaa indicates 17 amino acid residues

<400> SEQUENCE: 35

Gly Gly Arg Pro Ser Val Leu Gly Ile Ala Glu Asp Ala Leu Glu Phe
1               5                   10                  15

Ala Arg Glu Ala Ala Gln Asp Ser His Pro Asp Glu Tyr Leu Gly Leu
            20                  25                  30

Asp Gly Tyr Val Val Thr Asp Val Leu Val Ile Xaa Pro Asn Asp Met
        35                  40                  45

Arg Asn Val Gly Ser Ile His Ser His Pro Asn Gly Val Leu Ala Pro
    50                  55                  60

Ser Asp Ala Asp Arg Ser Met Phe Gly Lys Gly Gln Leu His Ile Ile
65                  70                  75                  80

Leu Gly His Pro Tyr Gly
                85

<210> SEQ ID NO 36
<211> LENGTH: 83
<212> TYPE: PRT
<213> ORGANISM: Sulfolobus solfataricus
<220> FEATURE:
<221> NAME/KEY: MISC_FEATURE
<222> LOCATION: (40)..(40)
<223> OTHER INFORMATION: Xaa indicates 15 amino acid residues

<400> SEQUENCE: 36

Asn Arg Tyr Phe Lys Ile Asn Cys Trp Ser Arg Arg Phe Met Asp Asn
1               5                   10                  15

Leu Lys Glu Lys Cys Gly Ile Ile Cys Asn Asn Thr Phe Tyr Glu Leu
            20                  25                  30

```
Lys Asn Ile Ser Arg Thr Glu Xaa Lys Cys Ser Asp Asp Ile Gln Ala
            35                  40                  45

Ile Val His Thr His Glu Glu Ser Cys Glu Pro Ser Tyr Lys Asp Ile
    50                  55                  60

Met Ser Met Lys Ile Trp Asn Ile Pro Trp Ile Ile Ser Lys Lys
65                  70                  75                  80

Cys Ile Lys

<210> SEQ ID NO 37
<211> LENGTH: 85
<212> TYPE: PRT
<213> ORGANISM: Aeropyrum pernix
<220> FEATURE:
<221> NAME/KEY: MISC_FEATURE
<222> LOCATION: (43)..(43)
<223> OTHER INFORMATION: Xaa indicates 24 amino acid residues

<400> SEQUENCE: 37

Ala Ser Ile Gly Pro Leu Arg Gln Val Leu Lys Leu Met Ala Leu Ala
1               5                   10                  15

His Asn Glu Glu Ala Gly Leu Val Ile Gly Ala Arg Arg Gly Asp Thr
            20                  25                  30

Val Tyr Ala Tyr Ile Leu Tyr Arg Thr Asp Xaa Lys Leu Gly Leu Glu
        35                  40                  45

Val Val Gly Val Tyr His Thr His Thr Thr Cys Pro Pro Ser Pro Ser
    50                  55                  60

Gly Lys Asp Val Glu Gly Met Lys Arg Trp Pro Gly Val Trp Leu Ile
65                  70                  75                  80

Ala Cys Pro Gly Glu
                85

<210> SEQ ID NO 38
<211> LENGTH: 82
<212> TYPE: PRT
<213> ORGANISM: Pyrobaculum aerophilum
<220> FEATURE:
<221> NAME/KEY: MISC_FEATURE
<222> LOCATION: (42)..(42)
<223> OTHER INFORMATION: Xaa indicates 20 amino acid residues

<400> SEQUENCE: 38

Met Pro Lys Ala Phe Leu Glu Glu Ala Arg Lys Lys Cys Ala Pro Glu
1               5                   10                  15

Ala Glu Cys Val Ala Leu Ile Phe Gly Ile Ser Asp Thr Ala Leu Ser
            20                  25                  30

Trp Arg Trp Met Lys Asn Val Ala Ala Xaa Glu Arg Gly Glu Glu Leu
        35                  40                  45

Leu Ala Ile Phe His Thr His Pro Gly Pro Thr Pro Ser Trp Glu
    50                  55                  60

Asp Val Arg His Met Arg Leu Trp Pro Val Thr Trp Ile Ile Ala Asn
65                  70                  75                  80

Val Phe

<210> SEQ ID NO 39
<211> LENGTH: 81
<212> TYPE: PRT
<213> ORGANISM: Aquifex aeolicus
<220> FEATURE:
<221> NAME/KEY: MISC_FEATURE
<222> LOCATION: (41)..(41)
<223> OTHER INFORMATION: Xaa indicates 28 amino acid residues
```

```
<400> SEQUENCE: 39

Lys Lys Glu Val Leu Glu Lys Met Ile Lys Gln Ala Glu Arg Asp Tyr
1               5                   10                  15

Pro Tyr Glu Thr Cys Gly Leu Leu Ile Gly Lys Ser Glu Gly Gly Ile
                20                  25                  30

Arg Ile Ala Tyr Glu Ala Phe Glu Xaa Ser Lys Gly Met Glu Ile Val
            35                  40                  45

Gly Val Tyr His Ser His Pro Asp His Pro Asp Arg Pro Ser Gln Phe
        50                  55                  60

Asp Leu Gln Arg Ala Phe Pro Asp Leu Ser Tyr Ile Ile Phe Ser Val
65                  70                  75                  80

Gln

<210> SEQ ID NO 40
<211> LENGTH: 85
<212> TYPE: PRT
<213> ORGANISM: Synechocystis sp.
<220> FEATURE:
<221> NAME/KEY: MISC_FEATURE
<222> LOCATION: (45)..(45)
<223> OTHER INFORMATION: Xaa indicates 39 amino acid residues

<400> SEQUENCE: 40

Ser Gln Val His Gln Asp Gln Ile Tyr Arg His Gly Glu Arg Cys Tyr
1               5                   10                  15

Pro Glu Glu Cys Cys Gly Leu Leu Leu Gly Lys Ile Leu Ile Gly Glu
                20                  25                  30

His Arg His Trp Gln Val Val Glu Val Gln Pro Thr Xaa Gln Lys Gly
            35                  40                  45

Leu Ser Ile Ile Gly Ile Phe His Ser His Pro His Gly Gln Pro Ile
        50                  55                  60

Pro Ser Glu Phe Asp Arg Ala Ile Ala Trp Pro Glu Tyr Ile Tyr Leu
65                  70                  75                  80

Ile Ala Ser Gly Glu
                85

<210> SEQ ID NO 41
<211> LENGTH: 85
<212> TYPE: PRT
<213> ORGANISM: Nostoc sp.
<220> FEATURE:
<221> NAME/KEY: MISC_FEATURE
<222> LOCATION: (45)..(45)
<223> OTHER INFORMATION: Xaa indicates 16 amino acid residues

<400> SEQUENCE: 41

Ile Ala Asn Gly Val Lys Thr Val Val Glu Val Ile Pro Thr Ala Asn
1               5                   10                  15

Ala Trp Glu Thr Glu Ala Asp Asn Phe Thr Gln Glu Ile Asn Lys Thr
                20                  25                  30

Asn Ile Thr Ser Pro Thr Ser Ser Leu Lys Arg Arg Xaa Asp Lys Ser
            35                  40                  45

Leu Asn Ile Ile Gly Ile Tyr His Ser His Pro Asp His Pro Ala Ile
        50                  55                  60

Pro Ser Glu Cys Asp Arg Leu Tyr Ala Trp Ala Gly Tyr Ser Tyr Ile
65                  70                  75                  80

Ile Val Ser Val Gln
                85
```

```
<210> SEQ ID NO 42
<211> LENGTH: 83
<212> TYPE: PRT
<213> ORGANISM: Deinococcus radiodurans
<220> FEATURE:
<221> NAME/KEY: MISC_FEATURE
<222> LOCATION: (42)..(42)
<223> OTHER INFORMATION: Xaa indicates 27 amino acid residues

<400> SEQUENCE: 42
```

Pro Ala Pro Leu Arg Arg Ala Leu Trp Ala Gln Val Arg Arg Glu Leu
1               5                   10                  15

Pro Arg Glu Cys Val Gly Ala Leu Gly Gly Trp Val Arg Gly Glu Gln
            20                  25                  30

Val Gln Ala His Ala Leu Tyr Pro Leu Xaa Arg Glu Gly Leu Asp Leu
        35                  40                  45

Val Ala Leu Tyr His Ser His Pro His Gly Pro Ala Ala Pro Ser Ala
    50                  55                  60

Ser Asp Arg Arg Leu Ala Ala Tyr Pro Val Pro Tyr Leu Ile Ala Asp
65                  70                  75                  80

Pro Ala Ala

```
<210> SEQ ID NO 43
<211> LENGTH: 84
<212> TYPE: PRT
<213> ORGANISM: Streptomyces coelicolor
<220> FEATURE:
<221> NAME/KEY: MISC_FEATURE
<222> LOCATION: (43)..(43)
<223> OTHER INFORMATION: Xaa indicates 32 amino acid residues

<400> SEQUENCE: 43
```

Thr Gln Ala Leu Tyr Asp Gln Ile Val Ala His Ala Arg Glu Asp His
1               5                   10                  15

Pro Asp Glu Ala Cys Gly Val Val Ala Gly Pro Ala Gly Glu Gly Arg
            20                  25                  30

Pro Glu Arg Phe Ile Pro Met Leu Asn Ala Xaa Asp Arg Asp Glu Glu
        35                  40                  45

Pro Val Val Ile Tyr His Ser His Thr Ala Thr Glu Ala His Pro Ser
    50                  55                  60

Arg Thr Asp Val Thr Tyr Ala Asn Glu Pro Gly Ala His Tyr Val Leu
65                  70                  75                  80

Val Ser Thr Ala

```
<210> SEQ ID NO 44
<211> LENGTH: 85
<212> TYPE: PRT
<213> ORGANISM: Mycobacterium tuberculosis
<220> FEATURE:
<221> NAME/KEY: MISC_FEATURE
<222> LOCATION: (40)..(40)
<223> OTHER INFORMATION: Xaa indicates 25 amino acid residues

<400> SEQUENCE: 44
```

Arg Ala Asp Leu Val Asn Ala Met Val Ala His Ala Arg Arg Asp His
1               5                   10                  15

Pro Asp Glu Ala Cys Gly Val Leu Ala Gly Pro Glu Gly Ser Asp Arg
            20                  25                  30

Pro Glu Arg His Ile Pro Met Xaa Asp Ala Asp Glu Val Pro Val Val
        35                  40                  45

Ile Tyr His Ser His Thr Ala Thr Glu Ala Tyr Pro Ser Arg Thr Asp
        50                      55                      60

Val Lys Leu Ala Thr Glu Pro Asp Ala His Tyr Val Leu Val Ser Thr
65                      70                      75                      80

Arg Asp Pro His Arg
                 85

<210> SEQ ID NO 45
<211> LENGTH: 78
<212> TYPE: PRT
<213> ORGANISM: Yersinia pestis
<220> FEATURE:
<221> NAME/KEY: MISC_FEATURE
<222> LOCATION: (35)..(35)
<223> OTHER INFORMATION: Xaa indicates 20 amino acid residues

<400> SEQUENCE: 45

Met Gln Glu Ile Tyr Leu Thr Ala Ile Lys Arg Tyr Pro Asn Glu Ala
1 5 10 15

Cys Gly Phe Leu Val Arg Thr Thr Gly Glu Lys Tyr Arg Phe Met Glu
20 25 30

Ala Arg Xaa Glu Asp Ala Gly Asp Val Val Ala Ile Trp His Ser His
35 40 45

Thr Asp Glu Ser Ala Asp Ala Ser Asp Ala Asp Arg Ala Gly Cys Glu
50 55 60

Ala Thr Glu Val Pro Trp Leu Ile Leu Ala Val Arg Lys Asn
65 70 75

<210> SEQ ID NO 46
<211> LENGTH: 83
<212> TYPE: PRT
<213> ORGANISM: Pseudomonas aeruginosa
<220> FEATURE:
<221> NAME/KEY: MISC_FEATURE
<222> LOCATION: (40)..(40)
<223> OTHER INFORMATION: Xaa indicates 18 amino acid residues

<400> SEQUENCE: 46

Ser Arg Ser Leu Gln Arg Ala Ile Ala Ala His Ala Ala Arg Glu His
1 5 10 15

Pro Arg Glu Cys Cys Gly Leu Ile Val Arg Gly Val Arg Gln Arg Arg
20 25 30

Tyr Val Ala Cys Arg Asn Ala Xaa Glu Asp Gln Gly Glu Val Leu Ala
35 40 45

Ile Val His Ser His Pro Asp Val Pro Ala Thr Pro Ser Met Ala Asp
50 55 60

Arg Val Ser Cys Glu Leu His Gly Leu Pro Trp Val Ile Leu Ser Trp
65 70 75 80

Pro Glu Gly

<210> SEQ ID NO 47
<211> LENGTH: 90
<212> TYPE: PRT
<213> ORGANISM: Pseudomonas aeruginosa
<220> FEATURE:
<221> NAME/KEY: MISC_FEATURE
<222> LOCATION: (43)..(43)
<223> OTHER INFORMATION: Xaa indicates 28 amino acid residues

<400> SEQUENCE: 47

Thr Glu His Ala Leu Ser Val Ile Tyr Arg His Ala Cys Arg Thr Tyr

-continued

```
1               5                   10                  15

Pro Arg Glu Cys Cys Gly Phe Val Leu Ala Asp Ala Lys Val Lys Glu
            20                  25                  30

Gly Thr Asn Ile Gln Asp Glu Leu His Met Xaa Lys Thr Cys Ser Pro
        35                  40                  45

Val Ser Val Ile Tyr His Ser His Pro Asp Val Gly Ala Tyr Phe Ser
    50                  55                  60

Arg Glu Asp Ile Asp Lys Ala Leu Tyr Ala Gly Glu Pro Met Leu Pro
65                  70                  75                  80

Val Asp Tyr Leu Val Val Asp Val Ala Ala
                85                  90

<210> SEQ ID NO 48
<211> LENGTH: 83
<212> TYPE: PRT
<213> ORGANISM: Ralstonia solanacearum
<220> FEATURE:
<221> NAME/KEY: MISC_FEATURE
<222> LOCATION: (40)..(40)
<223> OTHER INFORMATION: Xaa indicates 17 amino acid residues

<400> SEQUENCE: 48

Gln Glu Thr Thr Leu Asp Ala Ala Arg Arg His Ala Ala Arg Glu His
1               5                   10                  15

Pro Arg Glu Ala Cys Gly Leu Val Val Val Val Arg Gly Arg Glu Arg
            20                  25                  30

Tyr Met Ala Cys Arg Asn Val Xaa Glu Asp Leu Gly Glu Val Leu Ala
        35                  40                  45

Val Val His Ser His Pro Asn Ala Ser Ala Glu Pro Ser Glu Ala Asp
    50                  55                  60

Arg Val Ala Cys Glu Ala Ser Gly Leu Pro Trp His Ile Ile Ala Trp
65                  70                  75                  80

Pro Ala Asp

<210> SEQ ID NO 49
<211> LENGTH: 89
<212> TYPE: PRT
<213> ORGANISM: Vibrio cholerae
<220> FEATURE:
<221> NAME/KEY: MISC_FEATURE
<222> LOCATION: (42)..(42)
<223> OTHER INFORMATION: Xaa indicates 29 amino acid residues

<400> SEQUENCE: 49

Gly His Val Val Thr Arg Leu Leu Ser Tyr Arg Gln Leu His His Leu
1               5                   10                  15

Thr Pro Glu Ser Ala Gly Val Leu Ile Gly Glu Arg Arg Gly Gln His
            20                  25                  30

Leu Val Val Cys Asp Ile Ser Glu Pro Xaa Ala Gly Thr His Leu Tyr
        35                  40                  45

Leu Gly Glu Trp His Thr His Pro Glu Asp Arg Pro Phe Pro Ser Ala
    50                  55                  60

Thr Asp Arg His Ser Trp Arg Arg Asn Ile Val Ser Asp Glu Ser Met
65                  70                  75                  80

Leu Leu Leu Ile Val Gly Arg Lys Asp
                85

<210> SEQ ID NO 50
<211> LENGTH: 89
```

```
<212> TYPE: PRT
<213> ORGANISM: Rhizobium sp.
<220> FEATURE:
<221> NAME/KEY: MISC_FEATURE
<222> LOCATION: (43)..(43)
<223> OTHER INFORMATION: Xaa indicates 29 amino acid residues

<400> SEQUENCE: 50

Pro Glu Ser Val Val Glu Ala Met Leu Lys Asp Ala Ser Arg Trp His
1               5                   10                  15

Asp Leu Glu Thr Gly Gly Thr Phe Met Gly Tyr Trp Ser Asp Ala Asn
            20                  25                  30

Val Ala Val Ile Thr Lys Met Ile Asp Gly Xaa Gly Arg Val Asp Thr
        35                  40                  45

Tyr Ile Gly Asp Trp His Thr His Pro Asn Ala Gln Ser Glu Pro Ser
    50                  55                  60

Trp Thr Asp Arg Arg Cys Leu Arg Thr Ile Ile Arg Ser Pro Glu Val
65                  70                  75                  80

Met Ile Leu Leu Cys Gly Gly Pro Glu
                85

<210> SEQ ID NO 51
<211> LENGTH: 84
<212> TYPE: PRT
<213> ORGANISM: Ralstonia solanacearum
<220> FEATURE:
<221> NAME/KEY: MISC_FEATURE
<222> LOCATION: (41)..(41)
<223> OTHER INFORMATION: Xaa indicates 24 amino acid residues

<400> SEQUENCE: 51

Asp Leu Ala Phe Glu Arg Leu Gly Ala Thr Phe Pro Met Val Arg Ala
1               5                   10                  15

Phe Ile Glu Ala Ala Arg Lys Ala Ala Pro Asn Glu His Ala Ala Trp
            20                  25                  30

Val Val Trp Asp Ser Arg Thr Gly Xaa Glu Asp His Glu Ser Leu Val
        35                  40                  45

Val Asp Met His Ser His Gly Ala Leu Ala Ala Phe Phe Ser Glu Gln
    50                  55                  60

Asp Asn Arg Asp Asp Ala Gly Glu Val Lys Ile Ser Cys Val Val Gly
65                  70                  75                  80

Asp Leu Ala Asp

<210> SEQ ID NO 52
<211> LENGTH: 84
<212> TYPE: PRT
<213> ORGANISM: Nostoc sp.
<220> FEATURE:
<221> NAME/KEY: MISC_FEATURE
<222> LOCATION: (41)..(41)
<223> OTHER INFORMATION: Xaa indicates 25 amino acid residues

<400> SEQUENCE: 52

Leu Glu Pro Tyr Phe Arg Leu Lys Val Pro Lys Val Pro Cys Gln Ala
1               5                   10                  15

Ile Ala Glu Ile Ile Asn Ala Ala Ser Ile Asn Pro Gln Gln Glu Ile
            20                  25                  30

Leu Phe Tyr Leu Gly Val Thr Asn Xaa Lys Ser Tyr Thr Asp Gly Leu
        35                  40                  45

Val Glu Met His Ser His Gly Thr Leu Ala Ala Tyr Pro Ser Ser Ala
    50                  55                  60
```

```
Asp Asn Gln Glu Glu Lys Gly Lys Phe Arg Val Phe Ala Ile Ile Gly
65                  70                  75                  80

Thr Leu Asn Asn

<210> SEQ ID NO 53
<211> LENGTH: 84
<212> TYPE: PRT
<213> ORGANISM: Escherichia coli
<220> FEATURE:
<221> NAME/KEY: MISC_FEATURE
<222> LOCATION: (41)..(41)
<223> OTHER INFORMATION: Xaa indicates 18 amino acid residues

<400> SEQUENCE: 53

Ser Pro Glu Met Thr Arg Glu Phe Leu Gln Ser Gln Leu Thr Gly Glu
1               5                   10                  15

Glu Arg Glu Ile Phe Met Val Ile Phe Leu Asp Ser Gln His Arg Val
                20                  25                  30

Ile Thr His Arg Arg Leu Phe Ser Xaa Lys Ile Asn Ala Ser Ala Leu
            35                  40                  45

Ile Leu Ala His Asn His Pro Ser Gly Cys Ala Glu Pro Ser Lys Ala
        50                  55                  60

Asp Lys Leu Ile Thr Glu Arg Ile Ile Lys Ser Cys Gln Phe Met Asp
65                  70                  75                  80

Leu Arg Val Leu

<210> SEQ ID NO 54
<211> LENGTH: 84
<212> TYPE: PRT
<213> ORGANISM: Bacillus subtilis
<220> FEATURE:
<221> NAME/KEY: MISC_FEATURE
<222> LOCATION: (41)..(41)
<223> OTHER INFORMATION: Xaa indicates 18 amino acid residues

<400> SEQUENCE: 54

Ser Pro Glu Asp Gly Ala Asn Leu Val Met Glu Asp Met Arg Phe Leu
1               5                   10                  15

Thr Gln Glu His Phe Val Cys Leu Tyr Leu Asn Thr Lys Asn Gln Val
                20                  25                  30

Ile His Lys Arg Thr Val Phe Ile Xaa Lys Arg Ser Ala Ala Ser Phe
            35                  40                  45

Ile Cys Val His Asn His Pro Ser Gly Asp Pro Thr Pro Ser Arg Glu
        50                  55                  60

Asp Ile Glu Val Thr Arg Arg Leu Phe Glu Cys Gly Asn Leu Ile Gly
65                  70                  75                  80

Ile Glu Leu Leu

<210> SEQ ID NO 55
<211> LENGTH: 84
<212> TYPE: PRT
<213> ORGANISM: Methanosarcina acetivorans
<220> FEATURE:
<221> NAME/KEY: MISC_FEATURE
<222> LOCATION: (41)..(41)
<223> OTHER INFORMATION: Xaa indicates 18 amino acid residues

<400> SEQUENCE: 55

Ser Pro Lys Asp Val Tyr Ala Leu Met Tyr Pro Arg Met Arg Glu Gln
1               5                   10                  15
```

-continued

```
Lys Lys Glu Lys Phe Ile Thr Leu Tyr Leu Asp Thr Lys Asn Gln Ile
         20                  25                  30

Leu Lys Glu Glu Val Val Ser Ile Xaa Leu Glu Ser Ser Ala Ser Val
         35                  40                  45

Ile Met Val His Asn His Pro Ser Gly Asp Pro Ser Pro Ser Arg Glu
         50                  55                  60

Asp Ile Met Val Thr Glu Lys Leu Val Glu Gly Gly Lys Leu Leu Gly
65                   70                  75                  80

Ile Asp Ile Leu
```

<210> SEQ ID NO 56
<211> LENGTH: 84
<212> TYPE: PRT
<213> ORGANISM: Sinorhizobium meliloti
<220> FEATURE:
<221> NAME/KEY: MISC_FEATURE
<222> LOCATION: (41)..(41)
<223> OTHER INFORMATION: Xaa indicates 18 amino acid residues

<400> SEQUENCE: 56

```
Ser Trp Ser Ala Val Ile Asp Tyr Cys His Ala Ala Met Ala His Glu
1               5                   10                  15

Thr Lys Glu Gln Phe Arg Ile Leu Phe Leu Asp Lys Arg Asn Thr Leu
         20                  25                  30

Ile Ala Asp Glu Val Gln Gln Xaa Glu Leu Ser Ala Thr Ala Leu
         35                  40                  45

Ile Leu Val His Asn His Pro Ser Gly Asp Pro Thr Pro Ser Arg Ala
         50                  55                  60

Asp Ile Asp Met Thr Lys Leu Ile Ala Glu Ala Ala Lys Pro Leu Gly
65                   70                  75                  80

Ile Ala Leu His
```

<210> SEQ ID NO 57
<211> LENGTH: 84
<212> TYPE: PRT
<213> ORGANISM: Ralstonia solanacearum
<220> FEATURE:
<221> NAME/KEY: MISC_FEATURE
<222> LOCATION: (41)..(41)
<223> OTHER INFORMATION: Xaa indicates 18 amino acid residues

<400> SEQUENCE: 57

```
Ser Pro Gln Ser Val Lys Asp Phe Leu Arg Leu Thr Leu Gly His Arg
1               5                   10                  15

Pro Gln Glu Val Phe Ala Cys Leu Phe Leu Asp Val Arg His Arg Leu
         20                  25                  30

Ile Ala Trp Glu Glu Leu Phe Gln Xaa His His Asn Ala Ser Ala Leu
         35                  40                  45

Ile Leu Ser His Asn His Pro Thr Gly His Val Glu Pro Ser Glu Ser
         50                  55                  60

Asp Leu Val Leu Thr Arg Glu Leu Cys Arg Ala Leu Ala Leu Leu Asp
65                   70                  75                  80

Val Arg Val Leu
```

<210> SEQ ID NO 58
<211> LENGTH: 84
<212> TYPE: PRT
<213> ORGANISM: Agrobacterium tumefaciens str.
<220> FEATURE:
<221> NAME/KEY: MISC_FEATURE

```
<222> LOCATION: (41)..(41)
<223> OTHER INFORMATION: Xaa indicates 18 amino acid residues

<400> SEQUENCE: 58

Ser Trp Ser Ser Val Ile Asp Tyr Cys His Ala Met Ala His Glu
1               5                   10                  15

Thr Arg Glu Gln Phe Arg Ile Leu Phe Leu Asp Lys Arg Asn Val Leu
            20                  25                  30

Ile Ala Asp Glu Val Gln Gly Gln Xaa Glu Leu Ser Ser Thr Ala Leu
        35                  40                  45

Ile Leu Ile His Asn His Pro Ser Gly Asp Pro Thr Pro Ser Arg Ala
    50                  55                  60

Asp Ile Glu Met Thr Lys Thr Ile Ile Asp Thr Ala Lys Pro Leu Gly
65                  70                  75                  80

Ile Thr Val His

<210> SEQ ID NO 59
<211> LENGTH: 84
<212> TYPE: PRT
<213> ORGANISM: Synechocystis sp.
<220> FEATURE:
<221> NAME/KEY: MISC_FEATURE
<222> LOCATION: (41)..(41)
<223> OTHER INFORMATION: Xaa indicates 18 amino acid residues

<400> SEQUENCE: 59

Ser Pro Glu Ala Ala Ile Ala Leu Ser Gln Asp Leu Met Trp Gln
1               5                   10                  15

Thr Gln Glu His Phe Ala Ile Val Met Leu Asp Val Lys Asn Arg Leu
            20                  25                  30

Leu Ala Thr Lys Val Ile Thr Ile Xaa Lys Gln Gly Ala Thr Arg Leu
        35                  40                  45

Ile Val Ala His Asn His Pro Ser Gly Gly Leu Glu Pro Ser Pro Glu
    50                  55                  60

Asp Ile Arg Leu Thr Glu Phe Leu Leu Gln Gly Ala Gln Tyr Leu Gln
65                  70                  75                  80

Ile Pro Val Leu

<210> SEQ ID NO 60
<211> LENGTH: 84
<212> TYPE: PRT
<213> ORGANISM: Clostridium acetobutylicum
<220> FEATURE:
<221> NAME/KEY: MISC_FEATURE
<222> LOCATION: (41)..(41)
<223> OTHER INFORMATION: Xaa indicates 18 amino acid residues

<400> SEQUENCE: 60

Ser Pro Lys Glu Ala Ala Asn Leu Val Met Glu Gln Leu Arg Ser Phe
1               5                   10                  15

Asn Lys Glu His Leu Tyr Val Ile Met Leu Asn Thr Lys Asn Ile Val
            20                  25                  30

Ile Lys Ile Ser Asp Val Ser Val Xaa Leu Lys His Ala Ala Ser Ile
        35                  40                  45

Ile Leu Cys His Asn His Pro Ser Gly Asp Pro Lys Pro Ser Asn Glu
    50                  55                  60

Asp Leu Asn Ile Thr Lys Arg Leu Tyr Glu Cys Ser Lys Phe Ile Gly
65                  70                  75                  80

Ile Glu Leu Leu
```

<210> SEQ ID NO 61
<211> LENGTH: 84
<212> TYPE: PRT
<213> ORGANISM: Aquifex aeolicus
<220> FEATURE:
<221> NAME/KEY: MISC_FEATURE
<222> LOCATION: (41)..(41)
<223> OTHER INFORMATION: Xaa indicates 18 amino acid residues

<400> SEQUENCE: 61

Arg Asn Pro Gln Glu Ala Phe Glu Phe Leu Lys Asp Lys Phe Asp Glu
1               5                   10                  15

Arg Arg Glu Ser Leu Ile Ala Leu Tyr Leu Asp Leu Ser Asn Arg Leu
            20                  25                  30

Leu Asp Trp Glu Val Val Ala Ile Xaa Lys Leu Ser Ala Asn Gly Ile
        35                  40                  45

Ile Ile Ala His Asn His Pro Gln Gly Glu Pro Ser Pro Ser Asn Glu
    50                  55                  60

Asp Leu Asn Phe Thr Glu Arg Leu Lys Lys Ala Cys Glu Leu Leu Gly
65                  70                  75                  80

Phe Glu Leu Leu

<210> SEQ ID NO 62
<211> LENGTH: 84
<212> TYPE: PRT
<213> ORGANISM: Escherichia coli
<220> FEATURE:
<221> NAME/KEY: MISC_FEATURE
<222> LOCATION: (38)..(38)
<223> OTHER INFORMATION: Xaa is any amino acid
<220> FEATURE:
<221> NAME/KEY: MISC_FEATURE
<222> LOCATION: (41)..(41)
<223> OTHER INFORMATION: Xaa indicates 18 amino acid residues

<400> SEQUENCE: 62

Ser Thr Arg Ala Ala Arg Glu Trp Leu Ile Leu Asn Met Ala Gly Leu
1               5                   10                  15

Glu Arg Glu Glu Phe Arg Val Leu Tyr Leu Asn Asn Gln Asn Gln Leu
            20                  25                  30

Ile Ala Gly Glu Thr Xaa Phe Thr Xaa Tyr His Asn Ala Ala Ala Val
        35                  40                  45

Val Leu Ala His Asn His Pro Ser Gly Glu Val Thr Pro Ser Lys Ala
    50                  55                  60

Asp Arg Leu Ile Thr Glu Arg Leu Val Gln Ala Leu Gly Leu Val Asp
65                  70                  75                  80

Ile Arg Val Pro

<210> SEQ ID NO 63
<211> LENGTH: 84
<212> TYPE: PRT
<213> ORGANISM: Ralstonia solanacearum
<220> FEATURE:
<221> NAME/KEY: MISC_FEATURE
<222> LOCATION: (41)..(41)
<223> OTHER INFORMATION: Xaa indicates 18 amino acid residues

<400> SEQUENCE: 63

Ser Pro Ala Ala Val Lys Glu Tyr Leu Arg Ala Lys Leu Ala Gly Phe
1               5                   10                  15

Glu His Glu Val Phe Ala Val Leu Phe Met Asp Thr Gln His Arg Leu

```
                    20                  25                  30
Ile Glu Tyr Ala Glu Met Phe Arg Xaa Arg Leu Asn Ala Ala Val
            35                  40                  45

Ile Val Ser His Asn His Pro Ser Gly Asn Pro Glu Pro Ser Gly Ala
            50                  55                  60

Asp Arg Ala Leu Thr Gln Arg Leu Lys Glu Ala Leu Gly Leu Val Asp
 65                  70                  75                  80

Val Arg Val Leu

<210> SEQ ID NO 64
<211> LENGTH: 84
<212> TYPE: PRT
<213> ORGANISM: Vibrio cholerae
<220> FEATURE:
<221> NAME/KEY: MISC_FEATURE
<222> LOCATION: (41)..(41)
<223> OTHER INFORMATION: Xaa indicates 18 amino acid residues

<400> SEQUENCE: 64

Arg Thr Glu Asn Thr Thr Glu Tyr Leu Arg Cys Lys Leu Ala Gly Tyr
 1               5                  10                  15

Glu His Glu Ile Phe Ala Val Leu Phe Leu Asp Asn Gln His Arg Leu
            20                  25                  30

Ile Glu Phe Lys Glu Leu Phe Arg Xaa Asn Val Asn Ala Ala Val
            35                  40                  45

Ile Phe Ala His Asn His Pro Ser Gly Asp Pro Glu Pro Ser Gln Ala
            50                  55                  60

Asp Arg Arg Ile Thr Gln Arg Leu Lys Asp Ala Leu Ser Leu Val Asp
 65                  70                  75                  80

Ile Arg Val Leu

<210> SEQ ID NO 65
<211> LENGTH: 14
<212> TYPE: PRT
<213> ORGANISM: Artificial sequence
<220> FEATURE:
<223> OTHER INFORMATION: JAMM domain
<220> FEATURE:
<221> NAME/KEY: MISC_FEATURE
<222> LOCATION: (2)..(2)
<223> OTHER INFORMATION: Xaa is serine or threonine
<220> FEATURE:
<221> NAME/KEY: MISC_FEATURE
<222> LOCATION: (4)..(10)
<223> OTHER INFORMATION: Xaa is any amino acid
<220> FEATURE:
<221> NAME/KEY: MISC_FEATURE
<222> LOCATION: (12)..(13)
<223> OTHER INFORMATION: Xaa is any amino acid

<400> SEQUENCE: 65

His Xaa His Xaa Xaa Xaa Xaa Xaa Xaa Xaa Ser Xaa Xaa Asp
 1               5                  10

<210> SEQ ID NO 66
<211> LENGTH: 424
<212> TYPE: PRT
<213> ORGANISM: Homo sapiens

<400> SEQUENCE: 66

Met Ser Asp His Gly Asp Val Ser Leu Pro Pro Glu Asp Arg Val Arg
 1               5                  10                  15

Ala Leu Ser Gln Leu Gly Ser Ala Val Glu Val Asn Glu Asp Ile Pro
```

-continued

```
                    20                  25                  30
Pro Arg Arg Tyr Phe Arg Ser Gly Val Glu Ile Ile Arg Met Ala Ser
            35                  40                  45
Ile Tyr Ser Glu Glu Gly Asn Ile Glu His Ala Phe Ile Leu Tyr Asn
 50                  55                  60
Lys Tyr Ile Thr Leu Phe Ile Glu Lys Leu Pro Lys His Arg Asp Tyr
 65                  70                  75                  80
Lys Ser Ala Val Ile Pro Glu Lys Lys Asp Thr Val Lys Lys Leu Lys
                    85                  90                  95
Glu Ile Ala Phe Pro Lys Ala Glu Leu Lys Ala Glu Leu Leu Lys
                100                 105                 110
Arg Tyr Thr Lys Glu Tyr Thr Glu Tyr Asn Glu Glu Lys Lys Lys Glu
                115                 120                 125
Ala Glu Glu Leu Ala Arg Asn Met Ala Ile Gln Gln Glu Leu Glu Lys
                130                 135                 140
Glu Lys Gln Arg Val Ala Gln Gln Lys Gln Gln Gln Leu Glu Gln Glu
145                 150                 155                 160
Gln Phe His Ala Phe Glu Glu Met Ile Arg Asn Gln Glu Leu Glu Lys
                    165                 170                 175
Glu Arg Leu Lys Ile Val Gln Glu Phe Gly Lys Val Asp Pro Gly Leu
                180                 185                 190
Gly Gly Pro Leu Val Pro Asp Leu Glu Lys Pro Ser Leu Asp Val Phe
                195                 200                 205
Pro Thr Leu Thr Val Ser Ile Gln Pro Ser Asp Cys His Thr Thr
                210                 215                 220
Val Arg Pro Ala Lys Pro Val Val Asp Arg Ser Leu Lys Pro Gly
225                 230                 235                 240
Ala Leu Ser Asn Ser Glu Ser Ile Pro Thr Ile Asp Gly Leu Arg His
                    245                 250                 255
Val Val Val Pro Gly Arg Leu Cys Pro Gln Phe Leu Gln Leu Ala Ser
                260                 265                 270
Ala Asn Thr Ala Arg Gly Val Glu Thr Cys Gly Ile Leu Cys Gly Lys
                275                 280                 285
Leu Met Arg Asn Glu Phe Thr Ile Thr His Val Leu Ile Pro Lys Gln
290                 295                 300
Ser Ala Gly Ser Asp Tyr Cys Asn Thr Glu Asn Glu Glu Leu Phe
305                 310                 315                 320
Leu Ile Gln Asp Gln Gln Gly Leu Ile Thr Leu Gly Trp Ile His Thr
                325                 330                 335
His Pro Thr Gln Thr Ala Phe Leu Ser Ser Val Asp Leu His Thr His
                340                 345                 350
Cys Ser Tyr Gln Met Met Leu Pro Glu Ser Val Ala Ile Val Cys Ser
                355                 360                 365
Pro Lys Phe Gln Glu Thr Gly Phe Phe Lys Leu Thr Asp His Gly Leu
                370                 375                 380
Glu Glu Ile Ser Ser Cys Arg Gln Lys Gly Phe His Pro His Ser Lys
385                 390                 395                 400
Asp Pro Pro Leu Phe Cys Ser Cys Ser His Val Thr Val Val Asp Arg
                405                 410                 415
Ala Val Thr Ile Thr Asp Leu Arg
                420

<210> SEQ ID NO 67
```

```
<211> LENGTH: 421
<212> TYPE: PRT
<213> ORGANISM: Homo sapiens

<400> SEQUENCE: 67

Met Pro Asp His Thr Asp Val Ser Leu Ser Pro Glu Glu Arg Val Arg
1               5                   10                  15

Ala Leu Ser Lys Leu Gly Cys Asn Ile Thr Ile Ser Glu Asp Ile Thr
            20                  25                  30

Pro Arg Arg Tyr Phe Arg Ser Gly Val Glu Met Glu Arg Met Ala Ser
        35                  40                  45

Val Tyr Leu Glu Glu Gly Asn Leu Glu Asn Ala Phe Val Leu Tyr Asn
    50                  55                  60

Lys Phe Ile Thr Leu Phe Val Glu Lys Leu Pro Asn His Arg Asp Tyr
65                  70                  75                  80

Gln Gln Cys Ala Val Pro Glu Lys Gln Asp Ile Met Lys Lys Leu Lys
                85                  90                  95

Glu Ile Ala Phe Pro Arg Thr Asp Glu Leu Lys Asn Asp Leu Leu Lys
            100                 105                 110

Lys Tyr Asn Val Glu Tyr Gln Glu Tyr Leu Gln Ser Lys Asn Lys Tyr
        115                 120                 125

Lys Ala Glu Ile Leu Lys Lys Leu Glu His Gln Arg Leu Ile Glu Ala
    130                 135                 140

Glu Arg Lys Arg Ile Ala Gln Met Arg Gln Gln Leu Glu Ser Glu
145                 150                 155                 160

Gln Phe Leu Phe Phe Glu Asp Gln Leu Lys Lys Gln Glu Leu Ala Arg
                165                 170                 175

Gly Gln Met Arg Ser Gln Gln Thr Ser Gly Leu Ser Glu Gln Ile Asp
            180                 185                 190

Gly Ser Ala Leu Ser Cys Phe Ser Thr His Gln Asn Asn Ser Leu Leu
        195                 200                 205

Asn Val Phe Ala Asp Gln Pro Asn Lys Ser Asp Ala Thr Asn Tyr Ala
    210                 215                 220

Ser His Ser Pro Pro Val Asn Arg Ala Leu Thr Pro Ala Ala Thr Leu
225                 230                 235                 240

Ser Ala Val Gln Asn Leu Val Val Glu Gly Leu Arg Cys Val Val Leu
                245                 250                 255

Pro Glu Asp Leu Cys His Lys Phe Leu Gln Leu Ala Glu Ser Asn Thr
            260                 265                 270

Val Arg Gly Ile Glu Thr Cys Gly Ile Leu Cys Gly Lys Leu Thr His
        275                 280                 285

Asn Glu Phe Thr Ile Thr His Val Ile Val Pro Lys Gln Ser Ala Gly
    290                 295                 300

Pro Asp Tyr Cys Asp Met Glu Asn Val Glu Glu Leu Phe Asn Val Gln
305                 310                 315                 320

Asp Gln His Asp Leu Leu Thr Leu Gly Trp Ile His Thr His Pro Thr
                325                 330                 335

Gln Thr Ala Phe Leu Ser Ser Val Asp Leu His Thr His Cys Ser Tyr
            340                 345                 350

Gln Leu Met Leu Pro Glu Ala Ile Ala Ile Val Cys Ser Pro Lys His
        355                 360                 365

Lys Asp Thr Gly Ile Phe Arg Leu Thr Asn Ala Gly Met Leu Glu Val
    370                 375                 380

Ser Ala Cys Lys Lys Lys Gly Phe His Pro His Thr Lys Glu Pro Arg
```

```
                385                 390                 395                 400
Leu Phe Ser Ile Cys Lys His Val Leu Val Lys Asp Ile Lys Ile Ile
                405                 410                 415

Val Leu Asp Leu Arg
            420

<210> SEQ ID NO 68
<211> LENGTH: 461
<212> TYPE: PRT
<213> ORGANISM: Homo sapiens

<400> SEQUENCE: 68

Met Asp Gln Pro Phe Thr Val Asn Ser Leu Lys Lys Leu Ala Ala Met
1               5                   10                  15

Pro Asp His Thr Asp Val Ser Leu Ser Pro Glu Glu Arg Val Arg Ala
            20                  25                  30

Leu Ser Lys Leu Gly Cys Asn Ile Thr Ile Ser Glu Asp Ile Thr Pro
        35                  40                  45

Arg Arg Tyr Phe Arg Ser Gly Val Glu Met Glu Arg Met Ala Ser Val
    50                  55                  60

Tyr Leu Glu Glu Gly Asn Leu Glu Asn Ala Phe Val Leu Tyr Asn Lys
65                  70                  75                  80

Phe Ile Thr Leu Phe Val Glu Lys Leu Pro Asn His Arg Asp Tyr Gln
                85                  90                  95

Gln Cys Ala Val Pro Glu Lys Gln Asp Ile Met Lys Lys Leu Lys Glu
            100                 105                 110

Ile Ala Phe Pro Arg Thr Asp Glu Leu Lys Asn Asp Leu Leu Lys Lys
        115                 120                 125

Tyr Asn Val Glu Tyr Gln Glu Tyr Leu Gln Ser Lys Asn Lys Tyr Lys
    130                 135                 140

Ala Glu Ile Leu Lys Lys Leu Glu His Gln Arg Leu Ile Glu Ala Glu
145                 150                 155                 160

Arg Lys Arg Ile Ala Gln Met Arg Gln Gln Leu Glu Ser Glu Gln
                165                 170                 175

Phe Leu Phe Phe Glu Asp Gln Leu Lys Lys Gln Glu Leu Ala Arg Gly
            180                 185                 190

Gln Met Arg Ser Gln Gln Thr Ser Gly Leu Ser Glu Gln Ile Asp Gly
        195                 200                 205

Ser Ala Leu Ser Cys Phe Ser Thr His Gln Asn Asn Ser Leu Leu Asn
    210                 215                 220

Val Phe Ala Asp Gln Pro Asn Lys Ser Asp Ala Thr Asn Tyr Ala Ser
225                 230                 235                 240

His Ser Pro Pro Val Asn Arg Ala Leu Thr Pro Ala Ala Thr Leu Ser
                245                 250                 255

Ala Val Gln Asn Leu Val Val Glu Gly Leu Arg Cys Val Val Leu Pro
            260                 265                 270

Glu Asp Leu Cys His Lys Phe Leu Gln Leu Ala Glu Ser Asn Thr Val
        275                 280                 285

Arg Gly Ile Glu Thr Cys Gly Ile Leu Cys Gly Lys Leu Thr His Asn
    290                 295                 300

Glu Phe Thr Ile Thr His Val Ile Val Pro Lys Gln Ser Ala Gly Pro
305                 310                 315                 320

Asp Tyr Cys Asp Met Glu Asn Val Glu Glu Leu Phe Asn Val Gln Asp
                325                 330                 335
```

```
Gln His Asp Leu Leu Thr Leu Gly Trp Ile His Thr His Pro Thr Gln
            340                 345                 350

Thr Ala Phe Leu Ser Ser Val Asp Leu His Thr His Cys Ser Tyr Gln
        355                 360                 365

Leu Met Leu Pro Glu Ala Ile Ala Ile Val Cys Ser Pro Lys His Lys
    370                 375                 380

Asp Thr Gly Ile Phe Arg Leu Thr Asn Ala Gly Met Leu Glu Val Ser
385                 390                 395                 400

Ala Cys Lys Lys Lys Gly Phe His Pro His Thr Lys Glu Pro Arg Leu
                405                 410                 415

Phe Ser Ile Gln Lys Phe Leu Ser Gly Ile Ile Ser Gly Thr Ala Leu
            420                 425                 430

Glu Met Glu Pro Leu Lys Ile Gly Tyr Gly Pro Asn Gly Phe Pro Leu
        435                 440                 445

Leu Gly Ile Ser Arg Ser Ser Ser Pro Ser Glu Gln Leu
    450                 455                 460

<210> SEQ ID NO 69
<211> LENGTH: 58
<212> TYPE: PRT
<213> ORGANISM: Homo sapiens

<400> SEQUENCE: 69

Val Gly Arg Leu Glu Asn Ala Ile Gly Trp Tyr His Ser His Pro Gly
1               5                   10                  15

Tyr Gly Cys Trp Leu Ser Gly Ile Asp Val Ser Thr Gln Met Leu Asn
            20                  25                  30

Gln Gln Phe Gln Glu Pro Phe Val Ala Val Ile Asp Pro Thr Arg
        35                  40                  45

Thr Ile Ser Ala Gly Lys Val Asn Leu Gly
    50                  55

<210> SEQ ID NO 70
<211> LENGTH: 58
<212> TYPE: PRT
<213> ORGANISM: Drosophila melanogaster

<400> SEQUENCE: 70

Val Gly Arg Met Glu His Ala Val Gly Trp Tyr His Ser His Pro Gly
1               5                   10                  15

Tyr Gly Cys Trp Leu Ser Gly Ile Asn Val Ser Thr Gln Met Leu Asn
            20                  25                  30

Gln Thr Tyr Gln Glu Pro Phe Val Ala Ile Val Val Asp Pro Val Arg
        35                  40                  45

Thr Val Ser Ala Gly Lys Val Cys Leu Gly
    50                  55

<210> SEQ ID NO 71
<211> LENGTH: 58
<212> TYPE: PRT
<213> ORGANISM: Arabidopsis thaliana

<400> SEQUENCE: 71

Ala Gly Arg Leu Glu Asn Val Val Gly Trp Tyr His Ser His Pro Gly
1               5                   10                  15

Tyr Gly Cys Trp Leu Ser Gly Ile Asp Val Ser Thr Gln Arg Leu Asn
            20                  25                  30

Gln Gln His Gln Glu Pro Phe Leu Ala Val Val Ile Asp Pro Thr Arg
```

```
                35                  40                  45

Thr Val Ser Ala Gly Lys Val Glu Ile Gly
        50                  55

<210> SEQ ID NO 72
<211> LENGTH: 58
<212> TYPE: PRT
<213> ORGANISM: Caenorhabditis elegans

<400> SEQUENCE: 72

Glu Gly Arg Lys Glu Lys Val Val Gly Trp Tyr His Ser His Pro Gly
1               5                   10                  15

Tyr Gly Cys Trp Leu Ser Gly Ile Asp Val Ser Thr Gln Thr Leu Asn
            20                  25                  30

Gln Lys Phe Gln Glu Pro Trp Val Ala Ile Val Ile Asp Pro Leu Arg
        35                  40                  45

Thr Met Ser Ala Gly Lys Val Asp Ile Gly
        50                  55

<210> SEQ ID NO 73
<211> LENGTH: 58
<212> TYPE: PRT
<213> ORGANISM: Archaeoglobus fulgidus

<400> SEQUENCE: 73

Leu Pro Ile Gly Met Lys Val Phe Gly Thr Val His Ser His Pro Ser
1               5                   10                  15

Pro Ser Cys Arg Pro Ser Glu Glu Asp Leu Ser Leu Phe Thr Arg Phe
            20                  25                  30

Gly Lys Tyr His Ile Ile Val Cys Tyr Pro Tyr Asp Glu Asn Ser Trp
        35                  40                  45

Lys Cys Tyr Asn Arg Lys Gly Glu Glu Val
        50                  55

<210> SEQ ID NO 74
<211> LENGTH: 58
<212> TYPE: PRT
<213> ORGANISM: Pyrococcus horikoshii

<400> SEQUENCE: 74

Met Pro His Asp Glu Ser Ile Lys Gly Thr Phe His Ser His Pro Ser
1               5                   10                  15

Pro Phe Pro Tyr Pro Ser Glu Gly Asp Leu Met Phe Phe Ser Lys Phe
            20                  25                  30

Gly Gly Ile His Ile Ile Ala Ala Phe Pro Tyr Asp Glu Asp Ser Val
        35                  40                  45

Lys Ala Phe Asp Ser Glu Gly Arg Glu Val
        50                  55

<210> SEQ ID NO 75
<211> LENGTH: 58
<212> TYPE: PRT
<213> ORGANISM: Thermoplasma volcanium

<400> SEQUENCE: 75

Lys Pro Ile Asp Phe Ser Leu Val Gly Ser Val His Ser His Pro Ser
1               5                   10                  15

Gly Ile Thr Lys Pro Ser Asp Glu Asp Leu Arg Met Phe Ser Leu Thr
            20                  25                  30
```

-continued

Gly Lys Ile His Ile Ile Val Gly Tyr Pro Tyr Asn Leu Lys Asp Tyr
            35                  40                  45

Ser Ala Tyr Asp Arg Ser Gly Asn Lys Val
    50                  55

<210> SEQ ID NO 76
<211> LENGTH: 58
<212> TYPE: PRT
<213> ORGANISM: Methanobacterium thermoautotrophicum

<400> SEQUENCE: 76

Leu Pro Pro Phe Thr Gly Ala Val Gly Ser Val His Ser His Pro Gly
1               5                   10                  15

Pro Val Asn Leu Pro Ser Ala Ala Asp Leu His Phe Phe Ser Lys Asn
            20                  25                  30

Gly Leu Phe His Leu Ile Ile Ala His Pro Tyr Thr Met Glu Thr Val
            35                  40                  45

Ala Ala Tyr Thr Arg Asn Gly Asp Pro Val
    50                  55

<210> SEQ ID NO 77
<211> LENGTH: 58
<212> TYPE: PRT
<213> ORGANISM: Aquifex aeolicus

<400> SEQUENCE: 77

Ile Ser Lys Gly Met Glu Ile Val Gly Val Tyr His Ser His Pro Asp
1               5                   10                  15

His Pro Asp Arg Pro Ser Gln Phe Asp Leu Gln Arg Ala Phe Pro Asp
            20                  25                  30

Leu Ser Tyr Ile Ile Phe Ser Val Gln Lys Gly Lys Val Ala Ser Tyr
            35                  40                  45

Arg Ser Trp Glu Leu Lys Gly Asp Lys Phe
    50                  55

<210> SEQ ID NO 78
<211> LENGTH: 60
<212> TYPE: PRT
<213> ORGANISM: Mycobacterium tuberculosis

<400> SEQUENCE: 78

Glu Asp Ala Asp Glu Val Pro Val Val Ile Tyr His Ser His Thr Ala
1               5                   10                  15

Thr Glu Ala Tyr Pro Ser Arg Thr Asp Val Lys Leu Ala Thr Glu Pro
            20                  25                  30

Asp Ala His Tyr Val Leu Val Ser Thr Arg Asp Pro His Arg His Glu
            35                  40                  45

Leu Arg Ser Tyr Arg Ile Val Asp Gly Ala Val Thr
    50                  55                  60

<210> SEQ ID NO 79
<211> LENGTH: 58
<212> TYPE: PRT
<213> ORGANISM: Escherichia coli

<400> SEQUENCE: 79

Ile Lys Ile Asn Ala Ser Ala Leu Ile Leu Ala His Asn His Pro Ser
1               5                   10                  15

Gly Cys Ala Glu Pro Ser Lys Ala Asp Lys Leu Ile Thr Glu Arg Ile
            20                  25                  30

-continued

Ile Lys Ser Cys Gln Phe Met Asp Leu Arg Val Leu Asp His Ile Val
         35                  40                  45

Ile Gly Arg Gly Glu Tyr Val Ser Phe Ala
 50                  55

<210> SEQ ID NO 80
<211> LENGTH: 57
<212> TYPE: PRT
<213> ORGANISM: Drosophila melanogaster

<400> SEQUENCE: 80

Thr Gly Arg Pro Glu Met Val Val Gly Trp Tyr His Ser His Pro Gly
 1               5                  10                  15

Phe Gly Cys Trp Leu Ser Gly Val Asp Ile Asn Thr Gln Gln Ser Phe
             20                  25                  30

Glu Ala Leu Ser Glu Arg Ala Val Ala Val Val Asp Pro Ile Gln
         35                  40                  45

Ser Val Lys Gly Lys Val Val Ile Asp
 50                  55

<210> SEQ ID NO 81
<211> LENGTH: 57
<212> TYPE: PRT
<213> ORGANISM: Homo sapiens

<400> SEQUENCE: 81

Thr Gly Arg Pro Glu Met Val Val Gly Trp Tyr His Ser His Pro Gly
 1               5                  10                  15

Phe Gly Cys Trp Leu Ser Gly Val Asp Ile Asn Thr Gln Gln Ser Phe
             20                  25                  30

Glu Ala Leu Ser Glu Arg Ala Val Ala Val Val Asp Pro Ile Gln
         35                  40                  45

Ser Val Lys Gly Lys Val Val Ile Asp
 50                  55

<210> SEQ ID NO 82
<211> LENGTH: 57
<212> TYPE: PRT
<213> ORGANISM: Dictyostelium discoideum

<400> SEQUENCE: 82

Thr Gly Arg Asp Glu Ile Val Ile Gly Trp Tyr His Ser His Pro Gly
 1               5                  10                  15

Phe Gly Cys Trp Leu Ser Ser Val Asp Val Asn Thr Gln Gln Ser Phe
             20                  25                  30

Glu Gln Leu Gln Ser Arg Ala Val Ala Val Val Asp Pro Leu Gln
         35                  40                  45

Ser Val Arg Gly Lys Val Val Ile Asp
 50                  55

<210> SEQ ID NO 83
<211> LENGTH: 57
<212> TYPE: PRT
<213> ORGANISM: Saccharomyces cerevisiae

<400> SEQUENCE: 83

Thr Gly Arg Asp Gln Met Val Val Gly Trp Tyr His Ser His Pro Gly
 1               5                  10                  15

Phe Gly Cys Trp Leu Ser Ser Val Asp Val Asn Thr Gln Lys Ser Phe

-continued

```
                20                  25                  30
Glu Gln Leu Asn Ser Arg Ala Val Ala Val Val Val Asp Pro Ile Gln
            35                  40                  45

Ser Val Lys Gly Lys Val Val Ile Asp
    50                  55
```